US010478407B2

(12) United States Patent
Roy

(10) Patent No.: US 10,478,407 B2
(45) Date of Patent: Nov. 19, 2019

(54) PHARMACEUTICAL COMPOSITION FOR VIRAL INFECTIONS

(71) Applicant: The Administrators of the Tulane Educational Fund, New Orleans, LA (US)

(72) Inventor: Chad Roy, Madisonville, LA (US)

(73) Assignee: THE ADMINISTRATORS OF THE TULANE EDUCATIONAL FUND, New Orleans, LA (US)

(*) Notice: Subject to any disclaimer, the term of this patent is extended or adjusted under 35 U.S.C. 154(b) by 0 days.

(21) Appl. No.: 16/283,683

(22) Filed: Feb. 22, 2019

(65) Prior Publication Data
US 2019/0262286 A1  Aug. 29, 2019

Related U.S. Application Data

(60) Provisional application No. 62/784,185, filed on Dec. 21, 2018, provisional application No. 62/634,633, filed on Feb. 23, 2018.

(51) Int. Cl.
*A61K 31/14*  (2006.01)
*A61P 31/22*  (2006.01)
*A61P 31/14*  (2006.01)
*A61P 31/18*  (2006.01)
*A61P 31/20*  (2006.01)

(52) U.S. Cl.
CPC .............. *A61K 31/14* (2013.01); *A61P 31/14* (2018.01); *A61P 31/18* (2018.01); *A61P 31/20* (2018.01); *A61P 31/22* (2018.01)

(58) Field of Classification Search
CPC ..................................................... A61K 31/14
See application file for complete search history.

(56) References Cited

U.S. PATENT DOCUMENTS

| | | |
|---|---|---|
| 4,760,079 A | 7/1988 | Baldone et al. |
| 5,686,448 A | 11/1997 | Baldone et al. |
| 6,355,684 B1 | 3/2002 | Squires et al. |
| 6,414,032 B1 | 7/2002 | Johnson et al. |
| 6,420,431 B1 | 7/2002 | Johnson et al. |
| 6,423,750 B1 | 7/2002 | Johnson et al. |
| 6,559,189 B2 | 5/2003 | Baker, Jr. et al. |
| 6,689,814 B1 | 2/2004 | Argy et al. |
| 6,946,490 B2 | 9/2005 | Squires et al. |
| 8,846,725 B2 | 9/2014 | Johnson et al. |
| 9,662,360 B2 | 5/2017 | Squires et al. |
| 2002/0061926 A1 | 5/2002 | Phillips |

(Continued)

FOREIGN PATENT DOCUMENTS

WO    WO-9300114 A1    1/1993

OTHER PUBLICATIONS

PCT/US2019/09301 International Search Report and Written Opinion dated May 14, 2019.

*Primary Examiner* — San Ming R Hui
(74) *Attorney, Agent, or Firm* — Wilson Sonsini Goodrich & Rosati

(57) ABSTRACT

Disclosed herein are topical compositions comprising a quaternary ammonium salt and optionally ammonium chloride and/or stabilized chlorine dioxide. Also disclosed herein are methods of reducing the severity and/or duration of a dermal and or mucosal infection such as herpes or shingles. Also disclosed herein are methods of preventing the spread of a viral infection such as HIV. Also disclosed herein are methods of treating a viral infection such as keratoconjunctivitis.

19 Claims, 21 Drawing Sheets

(56) References Cited

U.S. PATENT DOCUMENTS

2010/0075914 A1   3/2010  Flack et al.
2013/0052235 A1   2/2013  Fattom et al.
2017/0065738 A1   3/2017  Roy et al.

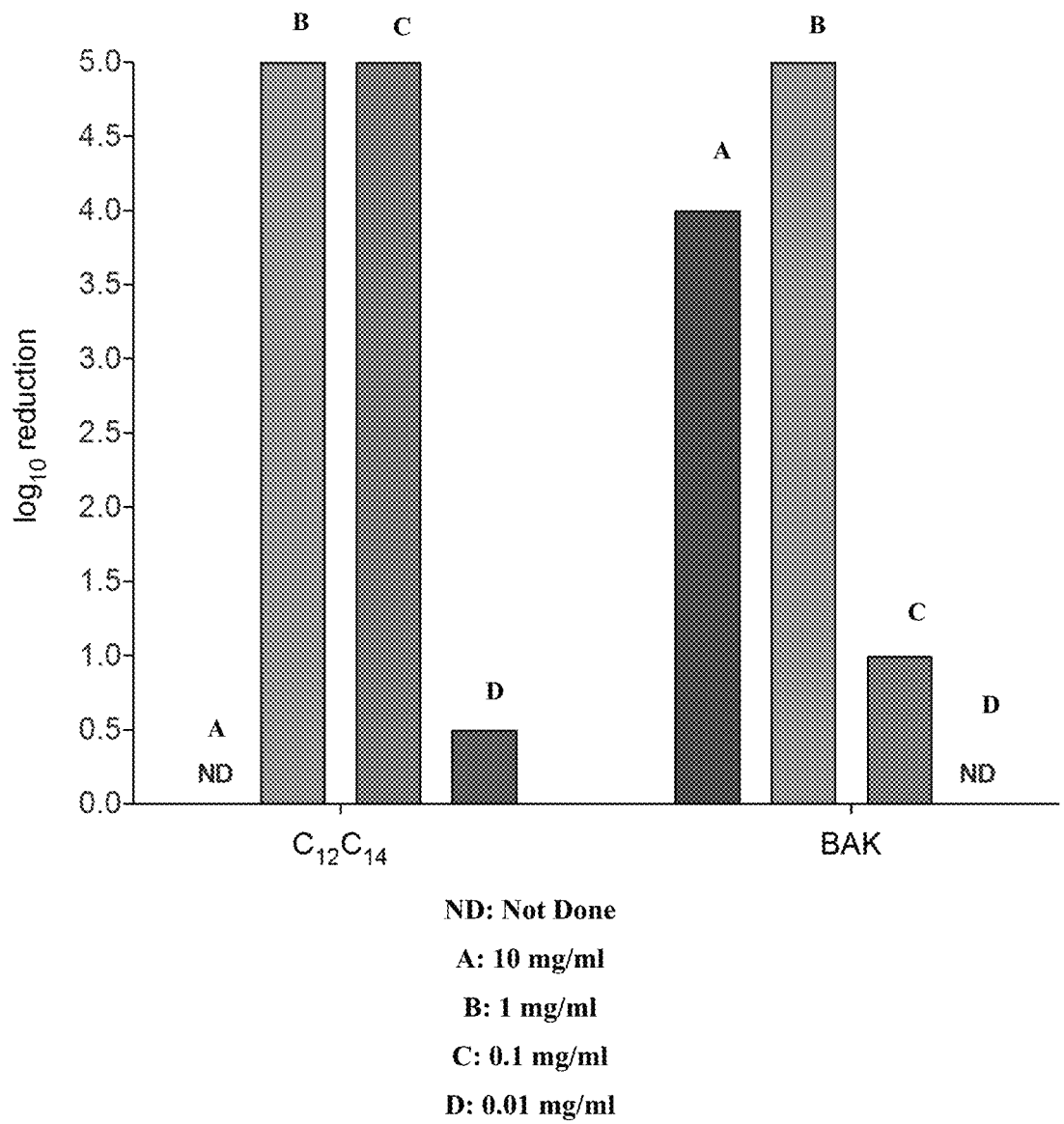

* No reduction
ND: Not Done
A: 10 mg/ml
B: 1 mg/ml
C: 0.1 mg/ml
D: 0.01 mg/ml

* No Reduction
A: 0.2 mg/ml
B: 0.1 mg/ml
C: 0.07 mg/ml
D: 0.05 mg/ml
E: 0.04 mg/ml A: 0.2 mg/ml
B: 0.1 mg/ml
C: 0.07 mg/ml
D: 0.05 mg/ml
E: 0.04 mg/ml

* statistically significant

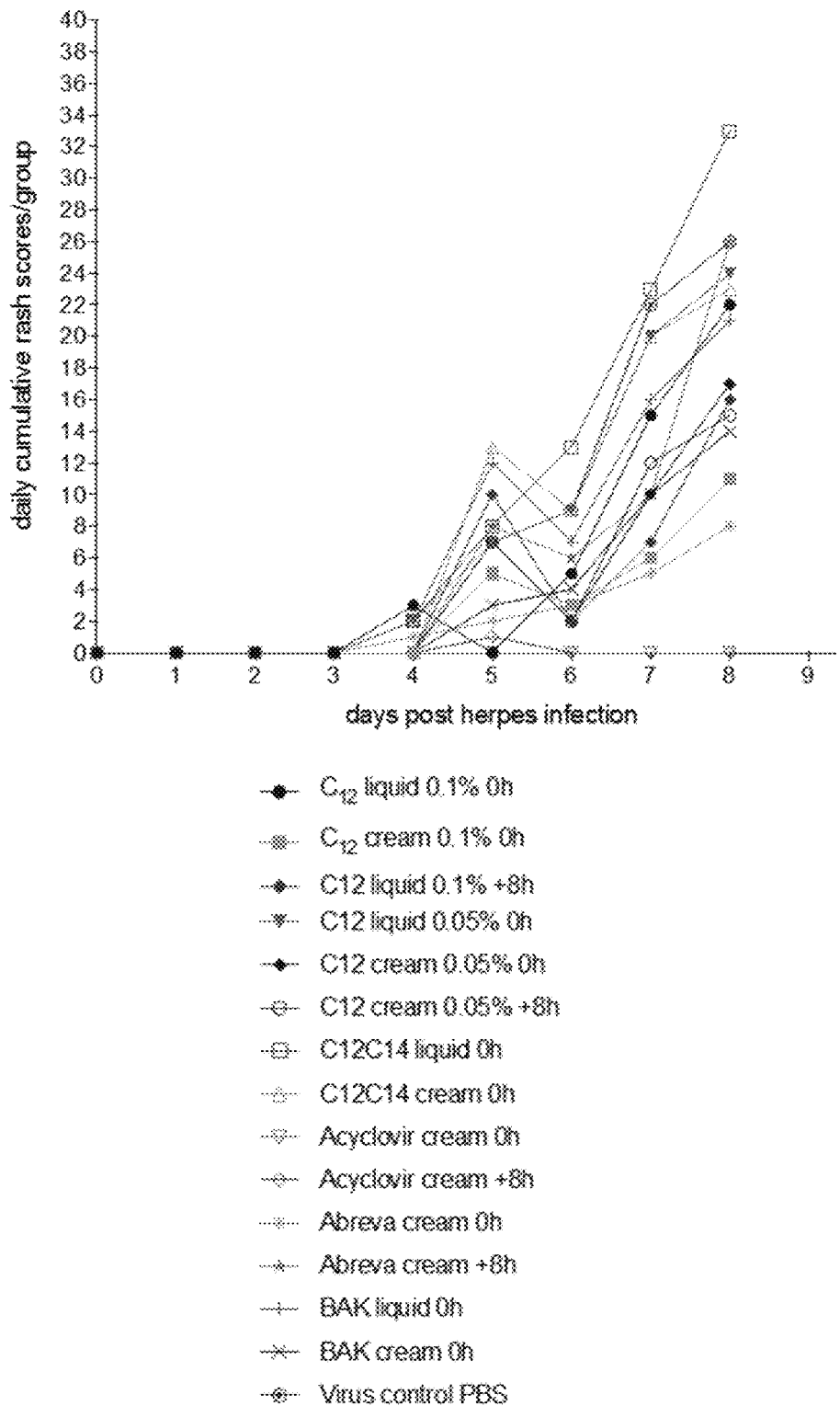

PHARMACEUTICAL COMPOSITION FOR VIRAL INFECTIONS

CROSS-REFERENCE

This patent application claims the benefit of U.S. Provisional Application No. 62/634,633, filed Feb. 23, 2018, and U.S. Provisional Application No. 62/784,185, filed Dec. 21, 2018, which are incorporated herein by reference in their entirety.

BACKGROUND

The present disclosure generally relates to the treatment or prevention of viral infections such as herpes virus infections, HIV infections, and adenovirus infections such as epidemic keratoconjunctivitis.

BRIEF SUMMARY OF THE INVENTION

Disclosed herein is a method of reducing the severity or the duration of the symptoms of an infection in a subject in need thereof, the method comprising administering to the subject in need thereof a pharmaceutical composition comprising C12-C14-alkyl(ethylbenzyl)dimethylammonium chloride.

In some embodiments of a method of reducing the severity or the duration of the symptoms of an infection, the viral infection is caused by the herpes simplex virus.

In some embodiments of a method of reducing the severity or the duration of the symptoms of an infection, the herpes simplex virus is herpes simplex virus type 1 (HSV-1), herpes simplex virus type 2 (HSV-2), or varicella zoster virus (VZV).

In some embodiments of a method of reducing the severity or the duration of the symptoms of an infection, the symptoms of the infection are selected from lesions, pain, fever, swollen lymph nodes, and any combinations thereof.

In some embodiments of a method of reducing the severity or the duration of the symptoms of an infection, the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

In some embodiments of a method of reducing the severity or the duration of the symptoms of an infection, the C12-C14-alkyl(ethylbenzyl)dimethylammonium chloride is C12-alkyl(ethylbenzyl)dimethylammonium chloride.

In some embodiments of a method of reducing the severity or the duration of the symptoms of an infection, the pharmaceutical composition is essentially free of alkyl(ethylbenzyl)dimethyl ammonium salt having an alkyl of less than 12 carbons or more than 14 carbons.

In some embodiments of a method of reducing the severity or the duration of the symptoms of an infection, the pharmaceutical composition is essentially free of benzalkonium chloride.

In some embodiments of a method of reducing the severity or the duration of the symptoms of an infection, the C12-C14-alkyl(ethylbenzyl)dimethylammonium chloride is present in an amount ranging from about 0.0001% to about 10% w/w.

In some embodiments of a method of reducing the severity or the duration of the symptoms of an infection, the C12-C14-alkyl(ethylbenzyl)dimethylammonium chloride is present in an amount ranging from about 0.001% to about 1% w/w.

In some embodiments of a method of reducing the severity or the duration of the symptoms of an infection, the pharmaceutical composition is in the form of an aerosol, a solution, a lotion, a gel, an ointment, a cream, a foam, a paste, or any combinations thereof.

In some embodiments of a method of reducing the severity or the duration of the symptoms of an infection, the subject in need thereof is immuno-compromised.

Also disclosed herein is a method of preventing the spread of a viral infection in a subject in need thereof, the method comprising administering to the subject in need thereof a pharmaceutical composition comprising C12-C14-alkyl(ethylbenzyl)dimethylammonium chloride.

In some embodiments of a method of preventing the spread of a viral infection in a subject in need thereof, the viral infection is caused by the influenza virus, the herpes simplex virus, the human immunodeficiency virus (HIV), the hepatitis B virus, the hepatitis C virus, the human papillomavirus (HPV), the ebolavirus, or an adenovirus.

In some embodiments of a method of preventing the spread of a viral infection in a subject in need thereof, the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

In some embodiments of a method of preventing the spread of a viral infection in a subject in need thereof, the C12-C14-alkyl(ethylbenzyl)dimethylammonium chloride is C12-alkyl(ethylbenzyl)dimethylammonium chloride.

In some embodiments of a method of preventing the spread of a viral infection in a subject in need thereof, the pharmaceutical composition is essentially free of alkyl(ethylbenzyl)dimethyl ammonium salt having an alkyl of less than 12 carbons or more than 14 carbons.

In some embodiments of a method of preventing the spread of a viral infection in a subject in need thereof, the pharmaceutical composition is essentially free of benzalkonium chloride.

In some embodiments of a method of preventing the spread of a viral infection in a subject in need thereof, the C12-C14-alkyl(ethylbenzyl)dimethylammonium chloride is present in an amount ranging from about 0.0001% to about 10% w/w.

In some embodiments of a method of preventing the spread of a viral infection in a subject in need thereof, the C12-C14-alkyl(ethylbenzyl)dimethylammonium chloride is present in an amount ranging from about 0.001% to about 1% w/w.

In some embodiments of a method of preventing the spread of a viral infection in a subject in need thereof, the subject in need thereof is immuno-compromised.

Also disclosed herein is a method of treating an infection in a subject in need thereof, the method comprising administering to the subject in need thereof a pharmaceutical composition comprising C12-C14-alkyl(ethylbenzyl)dimethylammonium chloride.

In some embodiments of a method of treating an infection in a subject in need thereof, the infection is caused by the human adenovirus or epidemic keratoconjunctivitis (EKC).

In some embodiments of a method of treating an infection in a subject in need thereof, the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

In some embodiments of a method of treating an infection in a subject in need thereof, the C12-C14-alkyl(ethylbenzyl) dimethylammonium chloride is C12-alkyl(ethylbenzyl)dimethylammonium chloride.

In some embodiments of a method of treating an infection in a subject in need thereof, the pharmaceutical composition is essentially free of alkyl(ethylbenzyl)dimethyl ammonium salt having an alkyl of less than 12 carbons or more than 14 carbons.

In some embodiments of a method of treating an infection in a subject in need thereof, the pharmaceutical composition is essentially free of benzalkonium chloride.

In some embodiments of a method of treating an infection in a subject in need thereof, the C12-C14-alkyl(ethylbenzyl) dimethylammonium chloride is present in an amount ranging from about 0.0001% to about 10% w/w.

In some embodiments of a method of treating an infection in a subject in need thereof, the C12-C14-alkyl(ethylbenzyl) dimethylammonium chloride is present in an amount ranging from about 0.001% to about 1% w/w.

In some embodiments of a method of treating an infection in a subject in need thereof, the subject in need thereof is immuno-compromised.

BRIEF DESCRIPTION OF THE DRAWINGS

The following drawings form part of the present specification and are included to further demonstrate certain aspects of the present disclosure. The disclosure may be better understood by reference to one or more of these drawings in combination with the description of specific embodiments presented herein.

FIG. 4A shows a graphical representation of the antiviral properties against HSV-1 strain of A-17 and B-17 at 15 minutes exposure.

FIG. 8 shows the daily rash scores, +8 d Post-Infection, all data.

Figure 1A:
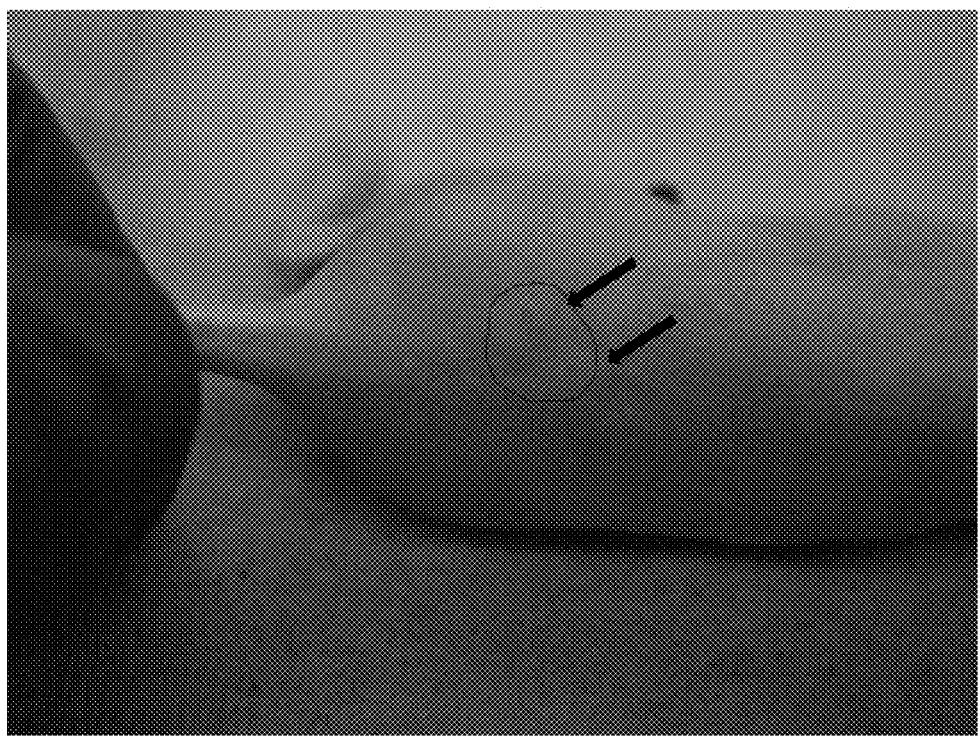
FIG. 1A shows a mouse topically inoculated with $10^5$ PFU of HSV-1 (control). Arrow: herpetic lesions.

DETAILED DESCRIPTION

The present disclosure generally relates to the treatment or prevention of viral infections such as herpes virus infections, HIV infections, and adenovirus infections such as epidemic keratoconjunctivitis.

Herpes simplex virus is composed of a double-stranded DNA nucleoprotein core surrounded by an icosahedral protein capsid, which in turn is enclosed in a lipid and glycoprotein outer envelope. It is a member of a family of eight known related human herpes viruses, including herpes simplex virus types 1 (HSV-1) and 2 (HSV-2), varicella-zoster virus (VZV), Epstein-Barr virus (EBV), cytomegalovirus (CMV), human herpes virus 6 (HHV-6), human herpes virus 7 (HHV-7,) and human herpes virus 8 (HHV-8). Many herpes viruses are capable of establishing latency in certain cell types, resulting in persistent infection.

Herpes simplex lesions generally occur as a result of a primary (initial) infection or as a result of a recurrence (reactivation) at the same site. During acute primary infection, the herpes simplex virus may establish latent infection in the nerve root ganglia that corresponds to the cutaneous or mucous membrane site of inoculation. Herpes simplex skin infections are usually located in the orolabial, genital, or anorectal areas. Orolabial HSV infection is typically HSV-1 and genital is typically HSV-2; however, each site may be infected with the other HSV type. Following orolabial infection, HSV becomes latent in the trigeminal ganglia and after genital or anorectal infection, HSV becomes latent in the sacral ganglia. A variety of stimuli, such as ultraviolet light, fever, menstruation, stress, local skin trauma, or trauma to the sensory nerve, can reactivate latent HSV.

In most cases the HSV infection is diagnosed by the morphological characteristics of the clinical symptoms including small, grouped vesicles on erythematous bases which then pustulate, ulcerate, and later form a crust. In some cases, systemic symptoms occur (e.g., fever, headache, myalgia, and malaise), but are more commonly associated with primary infection, especially genital herpes.

A primary infection with the herpes virus varicella zoster virus (VZV) results in the human disease varicella, also known as chicken pox. Primary infection leads to latent infection of dorsal root ganglia cells, giving rise to a reservoir of virus which can be reactivated. Reactivation of latent VZV gives rise to a condition referred to as herpes zoster or shingles. Both primary and reactivated VZV infections give rise to cutaneous lesions, although varicella symptoms can include mucosal lesions as well.

The present disclosure recognizes that there is no known treatment to kill the herpes virus at this time. Therefore there is a need for treatments that accelerate the healing of the lesions and the associated symptoms.

Sexually transmitted infections, and particularly HIV, pose a significant public health threat. At present, individuals wishing to protect themselves against such infections must rely upon mechanical measures (such as condoms) that prevent them from coming into contact with bodily fluids, which may contain HIV. These mechanical measures are non-optimal because some individuals are reluctant to use them. More recently, the use of orally administered antiretrovirals (e.g. tenofovir) has been postulated as pre-exposure prophylactic treatment. While oral prophylaxis is effective, it suffers from significant disadvantages. Oral prophylaxis must be used consistently for a prolonged period and its effectiveness is reduced or even eliminated if the patient is not fully compliant. Other oral medications can adversely affect the efficacy of oral prophylaxis. And, the effectiveness of an orally administered drug can be seriously compromised if a patient suffers from nausea or from diarrhea.

It would be advantageous to provide prophylaxis against sexually transmitted infections, and more particularly against HIV, that did not require the use of mechanical measures such as condoms and that did not need to be administered orally or by injection.

Epidemic keratoconjunctivitis (EKC) is a serious and contagious eye infection affecting both the conjunctiva and cornea and is caused by adenoviruses of type D, predominantly of serotypes 8, 19, 37. More than 50 serotypes of adenovirus have been isolated, and at least 19 documented serotypes cause eye infection. The most commonly associated serotypes that cause EKC include adenovirus 8, 19, and 37, and less frequently and in less severe forms, serotypes 2-5, 7, 9, 10, 11, 14, 16, 21, and 29.

EKC still lacks an effective treatment; hence there is a large unmet medical need. Povidone-iodine eye drops seem to have only limited efficacy and at the same time cause an additional stinging sensation in the inflamed eyes and sometimes even discoloration of the conjunctiva. A more compatible pharmaceutical composition that could be used for the treatment of EKC and for the prevention of its spread would thus be highly desirable for patients suffering from the disease, as well as for individuals that come into contact with such patients.

Detailed descriptions of one or more embodiments are provided herein. It is to be understood, however, that the present disclosure is embodied in various forms. Therefore, specific details disclosed herein are not to be interpreted as limiting, but rather as a basis for the claims and as a representative basis for teaching one skilled in the art to employ the present disclosure in any appropriate manner.

Wherever the phrase "for example," "such as," "including," and the like are used herein, the phrase "and without limitation" is understood to follow unless explicitly stated otherwise. Similarly "an example," "exemplary," and the like are understood to be non-limiting.

The term "substantially" allows for deviations from the descriptor that don't negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The term "about" is used to indicate that a value includes the standard level of error for the device or method being employed to determine the value. In some embodiments, the level of error is 10%. In some embodiments, the level of error is 9%. In some embodiments, the level of error is 8%. In some embodiments, the level of error is 7%. In some embodiments, the level of error is 6%. In some embodiments, the level of error is 5%.

The terms "comprising," "including," "having," "involving" (and similarly "comprises," "includes," "has," and "involves"), and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b, and c. Wherever the terms "a" or "an" are used, "one or more" is understood, unless such interpretation is nonsensical in context.

"Accelerated conditions" as used herein include temperature and/or relative humidity (RH) that are at or above ambient levels (e.g. 25±5° C.; 55±10% RH). In some instances, an accelerated condition is at about 25° C., about 30° C., about 35° C., about 40° C., about 45° C., about 50° C., about 55° C. or about 60° C. In other instances, an accelerated condition is above 55% RH, about 65% RH, about 70% RH, about 75% RH, or about 80% RH. In further instances, an accelerated condition is about 40° C. or 60° C. at ambient humidity. In yet further instances, an accelerated condition is about 40° C. at 75±5% RH humidity.

"Refrigerated condition" as used herein refer to 5±3° C. In some embodiments, refrigerated condition is about 2° C., about 2.1° C., about 2.2° C., about 2.3° C., about 2.4° C., about 2.5° C., about 2.6° C., about 2.7° C., about 2.8° C., about 2.9° C., about 3° C., about 3.1° C., about 3.2° C., about 3.3° C., about 3.4° C., about 3.5° C., about 3.6° C., about 3.7° C., about 3.8° C., about 3.9° C., about 4° C., about 4.1° C., about 4.2° C., about 4.3° C., about 4.4° C., about 4.5° C., about 4.6° C., about 4.7° C., about 4.8° C., about 4.9° C., about 5° C., about 5.1° C., about 5.2° C., about 5.3° C., about 5.4° C., about 5.5° C., about 5.6° C., about 5.7° C., about 5.8° C., about 5.9° C., about 6° C., about 6.1° C., about 6.2° C., about 6.3° C., about 6.4° C., about 6.5° C., about 6.6° C., about 6.7° C., about 6.8° C., about 6.9° C., about 7° C., about 7.1° C., about 7.2° C., about 7.3° C., about 7.4° C., about 7.5° C., about 7.6° C., about 7.7° C., about 7.8° C., about 7.9° C., or about 8° C.

Pharmaceutical Compositions

Disclosed herein are pharmaceutical compositions comprising a quaternary ammonium salt. In some embodiments, the quaternary ammonium salt is C10-C16-alkyl(ethylbenzyl)dimethylammonium chloride. In some embodiments, the pharmaceutical composition further comprises ammonium chloride. In some embodiments, the pharmaceutical composition further comprises a chlorite salt. In some embodiments, the pharmaceutical composition further comprises a pharmaceutically acceptable carrier. In some embodiments, the pharmaceutical composition further comprises a pharmaceutically acceptable excipient. In some embodiments, the pharmaceutically acceptable excipient is selected from buffers, viscosity agents, permeation enhancers, surfactants, stabilizers, emulsifiers, preservatives, thickening agents, and any combinations thereof. Exemplary pharmaceutically acceptable excipients of the disclosure include those found in Remington: The Science and Practice of Pharmacy, Twenty Second Ed. (London, UK: Pharmaceutical Press, 2013) incorporated herein by reference for such disclosure.

In some embodiments, the pharmaceutical composition comprises about 0.0001% to about 10% w/w of a quaternary ammonium salt. In some embodiments, the quaternary ammonium salt is C10-C16-alkyl(ethylbenzyl)dimethylammonium chloride. In some embodiments, the the pharmaceutical composition comprises about 0.0001% to about 10% w/w of ammonium chloride. In some embodiments, the pharmaceutical composition further comprises about 0.0001% to about 10% w/w of a chlorite salt.

In some embodiments, the pharmaceutical composition comprises about 0.0001% to about 5% w/w of a quaternary ammonium salt. In some embodiments, the quaternary ammonium salt is C10-C16-alkyl(ethylbenzyl)dimethylammonium chloride. In some embodiments, the the pharmaceutical composition comprises about 0.0001% to about 5% w/w of ammonium chloride. In some embodiments, the pharmaceutical composition further comprises about 0.0001% to about 5% w/w of a chlorite salt.

In some embodiments, the pharmaceutical composition comprises about 0.0001% to about 0.5% w/w of a quaternary ammonium salt. In some embodiments, the quaternary ammonium salt is C10-C16-alkyl(ethylbenzyl)dimethylammonium chloride. In some embodiments, the the pharmaceutical composition comprises about 0.0001% to about 0.5% w/w of ammonium chloride. In some embodiments, the pharmaceutical composition further comprises about 0.0001% to about 0.5% w/w of a chlorite salt.

In some embodiments, the pharmaceutical composition comprises about 0.015% w/w of a quaternary ammonium salt. In some embodiments, the quaternary ammonium salt is C10-C16-alkyl(ethylbenzyl)dimethylammonium chloride. In some embodiments, the the pharmaceutical composition comprises about 0.02% w/w of ammonium chloride. In some embodiments, the pharmaceutical composition further comprises about 0.0006% w/w of a chlorite salt.

Quaternary Ammonium Salt

In some aspects, the pharmaceutical composition comprises a quaternary ammonium salt. In some embodiments, the quaternary ammonium salt is a salt of a quaternary ammonium cation. As used herein "quaternary ammonium cations" also known as quats, refer to positively charged polyatomic ions of the structure $NR_4^+$, R being an optionally substituted alkyl group or an optionally substituted aryl group. Unlike the ammonium ion ($NH_4^+$) and the primary, secondary, or tertiary ammonium cations, the quaternary ammonium cations are permanently charged, independent of the pH of their solution. In some embodiments, the quaternary ammonium salt is not a polymeric quaternary ammonium salt. In some embodiments, the quaternary ammonium salt comprises a C10 or C16 alkyl chain. In some embodiments, the quaternary ammonium salt comprises a C12 or C14 alkyl chain. In some embodiments, the quaternary ammonium salt is not benzalkonium chloride. In some embodiments, the quaternary ammonium salt is C10-C16-alkyl(ethylbenzyl)dimethylammonium chloride. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the quaternary ammonium salt is substantially pure C12-alkyl(ethylbenzyl)dimethylammonium chloride that is separated from a mixture of C12-C14-alkyl(ethylbenzyl)dimethylammonium chloride. In some embodiments, the quaternary ammonium salt is C12-alkyl(ethylbenzyl)dimethylammonium chloride that is separated from a mixture of C12-C14-alkyl(ethylbenzyl)dimethylammonium chloride and contains less than about 1%, about 2%, about 3%, about 4%, about 5%, about 6%, about 7%, about 8%, about 9%, or about 10% of C14-alkyl(ethylbenzyl)dimethylammonium chloride. In some embodiments, the quaternary ammonium salt, e.g., C12-alkyl(ethylbenzyl)dimethylammonium chloride, does not have any toxicity.

In some embodiments, the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

In some embodiments, the pharmaceutical composition is essentially free of alkyl(ethylbenzyl)dimethyl ammonium salt having an alkyl of less than 12 carbons or more than 14 carbons.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01 mg/ml to about 10 mg/ml. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 0.01 mg/ml, about 0.05 mg/ml, about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, about 1.5 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml, about 7 mg/ml, about 7.5 mg/ml, about 8 mg/ml, about 8.5 mg/ml, about 9 mg/ml, about 9.5 mg/ml, or about 10 mg/ml.

In some embodiments, the pharmaceutical composition described herein is substantially free of benzalkonium chloride. In some embodiments, the amount of quaternary ammonium salt is lower than the amount of known quaternary ammonium salts, for example benzalkonium chloride, by about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.5% w/w. In some embodiments, the quaternary ammonium salt, e.g., C12-C14-alkyl(ethylbenzyl)dimethylammonium chloride or C12-alkyl(ethylbenzyl)dimethylammonium chloride is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.01% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.002% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0005% to about 0.002% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0005% to about 0.0012% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 0.001% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 0.0008% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.005%, about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, or about 10% w/w.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount between about 10% w/w and about 20% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount between about 10% w/w and about 15% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount between about 15% w/w and about 20% w/w.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 10% w/w, about 10.1% w/w, about 10.2% w/w, about 10.3% w/w, about 10.4% w/w, about 10.5% w/w, about 10.6% w/w, about 10.7% w/w, about 10.8% w/w, about 10.9% w/w, about 11% w/w, about 11.1% w/w, about 11.2% w/w, about 11.3% w/w, about 11.4% w/w, about 11.5% w/w, about 11.6% w/w, about 11.7% w/w, about 11.8% w/w, about 11.9% w/w, about 12% w/w, about 12.1% w/w, about 12.2% w/w, about 12.3% w/w, about 12.4% w/w, about 12.5% w/w, about 12.6% w/w, about 12.7% w/w, about 12.8% w/w, about 12.9% w/w, about 13% w/w, about 13.1% w/w, about 13.2% w/w, about 13.3% w/w, about 13.4% w/w, about 13.5% w/w, about 13.6% w/w, about 13.7% w/w, about 13.8% w/w, about 13.9% w/w, about 14% w/w, about 14.1% w/w, about 14.2% w/w, about 14.3% w/w, about 14.4% w/w, about 14.5% w/w, about 14.6% w/w, about 14.7% w/w, about 14.8% w/w, about 14.9% w/w, about 15% w/w, about 15.1% w/w, about 15.2% w/w, about 15.3% w/w, about 15.4% w/w, about 15.5% w/w, about 15.6% w/w, about 15.7% w/w, about 15.8% w/w, about 15.9% w/w, about 16% w/w, about 16.1% w/w, about 16.2% w/w, about 16.3% w/w, about 16.4% w/w, about 16.5% w/w, about 16.6% w/w, about 16.7% w/w, about 16.8% w/w, about 16.9% w/w, about 17% w/w, about 17.1% w/w, about 17.2% w/w, about 17.3% w/w, about 17.4% w/w, about 17.5% w/w, about 17.6% w/w, about 17.7% w/w, about 17.8% w/w, about 17.9% w/w, about 18% w/w, about 18.1% w/w, about 18.2% w/w, about 18.3% w/w, about 18.4% w/w, about 18.5% w/w, about 18.6% w/w, about 18.7% w/w, about 18.8% w/w, about 18.9% w/w, about 19% w/w, about 19.1% w/w, about 19.2% w/w, about 19.3% w/w, about 19.4% w/w, about 19.5% w/w, about 19.6% w/w, about 19.7% w/w, about 19.8% w/w, about 19.9% w/w, or about 20% w/w.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.01% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.001% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 0.01% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 2% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 3% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 4% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 2% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 3% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 2% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 1% w/w. In some embodiments, the quaternary ammonium salt destroys phospholipids within the microbial cell wall, prompting autolysis and microbial cell entry for the oxychlorine-based component in the formulation (e.g. sodium chlorite, stabilized chlorine dioxide, or chlorine dioxide).

Ammonium Chloride

In some aspects, the pharmaceutical composition further comprises ammonium chloride. As used herein "ammonium chloride" refers to $NH_4Cl$. In some embodiments, the ammonium chloride is present in the pharmaceutical composition in an amount ranging from about 0.001% to about 2% w/w. In some embodiments, the ammonium chloride is present in the pharmaceutical composition in an amount of about 0.001%, about 0.005%, about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2% w/w. In some embodiments, the ammonium chloride is present in the pharmaceutical composition in an amount ranging from about 0.001% to about 1% w/w. In some embodiments, the ammonium chloride is present in the pharmaceutical composition in an amount ranging from about 0.01% to about 1% w/w. In some embodiments, the ammonium chloride is present in the pharmaceutical composition in an amount ranging from about 0.1% to about 1% w/w. In some embodiments, the ammonium chloride is present in the pharmaceutical composition in an amount ranging from about 0.01% to about 0.3% w/w. In some embodiments, the ammonium chloride is present in the pharmaceutical composition in an amount ranging from about 0.1% to about 0.3% w/w. In some embodiments, the ammonium chloride is present in the pharmaceutical composition in an amount of about 0.2% w/w. In some embodiments, the ammonium chloride is present in the pharmaceutical composition in an amount ranging from about 0.0001% to about 10% w/w. In some embodiments, the ammonium chloride is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.005%, about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, or about 10% w/w. In some embodiments, the ammonium chloride is present in the pharmaceutical composition in an amount ranging from about 0.0001% to about 5% w/w. In some embodiments, the ammonium chloride is present in the pharmaceutical composition in an amount ranging from about 0.0001% to about 4% w/w. In some embodiments, the ammonium chloride is present in the pharmaceutical composition in an amount ranging from about 0.0001% to about 3% w/w. In some embodiments, the ammonium chloride is present in the pharmaceutical composition in an amount ranging from about 0.0001% to about 2% w/w. In some embodiments, the ammonium chloride is present in the pharmaceutical composition in an amount ranging from about 0.0001% to about 1% w/w. In some embodiments, the ammonium chloride is present in the pharmaceutical composition in an amount ranging from about 0.0001% to about 0.1% w/w. In some embodiments, the ammonium chloride is present in the pharmaceutical composition in an amount ranging from about 0.0001% to about 0.01% w/w. In some embodiments, the ammonium chloride is present in the pharmaceutical composition in an amount ranging from about 0.0001% to about 0.001% w/w. In some embodiments, the ammonium chloride is present in the pharmaceutical composition in an amount ranging from about 0.001% to about 5% w/w. In some embodiments, the ammonium chloride is present in the pharmaceutical composition in an amount ranging from about 0.001% to about 4% w/w. In some embodiments, the ammonium chloride is present in the pharmaceutical composition in an amount ranging from about 0.001% to about 3% w/w. In some embodiments, the ammonium chloride is present in the pharmaceutical composition in an amount ranging from about 0.001% to about 2% w/w. In some embodiments, the ammonium chloride is present in the pharmaceutical composition in an amount ranging from about 0.001% to about 1% w/w. In some embodiments, the ammonium chloride is present in the pharmaceutical composition in an amount ranging from about 0.001% to about 0.1% w/w. In some embodiments, the ammonium chloride is present in the pharmaceutical composition in an amount ranging from about 0.001% to about 0.01% w/w. In some embodiments, the ammonium chloride is present in the pharmaceutical composition in an amount ranging from about 0.01% to about 5% w/w. In some embodiments, the ammonium chloride is present in the pharmaceutical composition in an amount ranging from about 0.01% to about 4% w/w. In some embodiments, the ammonium chloride is present in the pharmaceutical composition in an amount ranging from about 0.01% to about 3% w/w. In some embodiments, the ammonium chloride is present in the pharmaceutical composition in an amount ranging from about 0.01% to about 2% w/w. In some embodiments, the ammonium chloride is present in the pharmaceutical composition in an amount ranging from about 0.01% to about 1% w/w. In some embodiments, the ammonium chloride is present in the pharmaceutical composition in an amount ranging from about 0.01% to about 0.1% w/w. In some embodiments, the ammonium chloride is present in the pharmaceutical composition in an amount ranging from about 0.001% to about 5% w/w. In some embodiments, the ammonium chloride is present in the pharmaceutical composition in an amount ranging from about 0.01% to about 5% w/w. In some embodiments, the ammonium chloride is present in the pharmaceutical composition in an amount ranging from about 0.1% to about 5% w/w. In some embodiments, the ammonium chloride is present in the pharmaceutical composition in an amount ranging from about 1% to about 5% w/w. In some embodiments, the ammonium chloride is present in the pharmaceutical composition in an amount ranging from about 2% to about 5% w/w. In some embodiments, the ammonium chloride is present in the pharmaceutical composition in an amount ranging from about 3% to about 5% w/w. In some embodiments, the ammonium chloride is present in the pharmaceutical composition in an amount ranging from about 4% to about 5% w/w. In some embodiments, the ammonium chloride is present in the pharmaceutical composition in an amount ranging from about 0.001% to about 4% w/w. In some embodiments, the ammonium chloride is present in the pharmaceutical composition in an amount ranging from about 0.01% to about 4% w/w. In some embodiments, the ammonium chloride is present in the pharmaceutical composition in an amount ranging from about 0.1% to about 4% w/w. In some embodiments, the ammonium chloride is present in the pharmaceutical composition in an amount ranging from about 1% to about 4% w/w. In some embodiments, the ammonium chloride is present in the pharmaceutical composition in an amount ranging from about 2% to about 4% w/w. In some embodiments, the ammonium chloride is present in the pharmaceutical composition in an amount ranging from about 3% to about 4% w/w. In some embodiments, the ammonium chloride is present in the pharmaceutical composition in an amount ranging from about 0.001% to about 3% w/w. In some embodiments, the ammonium chloride is present in the pharmaceutical composition in an amount ranging from about 0.01% to about 3% w/w. In some embodiments, the ammonium chloride is present in the pharmaceutical composition in an amount ranging from about 0.1% to about 3% w/w. In some embodiments, the ammonium chloride is present in the pharmaceutical composition in an amount ranging from about 1% to about 3% w/w. In some embodiments, the ammonium chloride is present in the pharmaceutical composition in an amount ranging from about 2% to about 3% w/w. In some embodiments, the ammonium chloride is present in the pharmaceutical composition in an amount ranging from about 0.001% to about 2% w/w. In some embodiments, the ammonium chloride is present in the pharmaceutical composition in an amount ranging from about 0.01% to about 2% w/w. In some embodiments, the ammonium chloride is present in the pharmaceutical composition in an amount ranging from about 0.1% to about 2% w/w. In some embodiments, the ammonium chloride is present in the pharmaceutical composition in an amount ranging from about 1% to about 2% w/w. In some embodiments, the ammonium chloride is present in the pharmaceutical composition in an amount ranging from about 0.001% to about 1% w/w. In some embodiments, the ammonium chloride is present in the pharmaceutical composition in an amount ranging from about 0.01% to about 1% w/w. In some embodiments, the ammonium chloride is present in the pharmaceutical composition in an amount ranging from about 0.1% to about 1% w/w.

Chlorite Salt

In some aspects, the pharmaceutical composition further comprises a chlorite salt. In some embodiments, the chlorite salt is an alkaline earth metal chlorite salt. In some embodiments, the chlorite salt is an alkali metal chlorite salt. In some embodiments, the chlorite salt is sodium chlorite. In some embodiments, the chlorite salt, e.g., sodium chlorite, is present in the pharmaceutical composition in an amount ranging from about 0.0001% to about 1% w/w. In some embodiments, the chlorite salt, e.g., sodium chlorite, is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.005%, about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% w/w. In some embodiments, the chlorite salt, e.g., sodium chlorite, is present in the pharmaceutical composition in an amount ranging from about 0.0001% to about 0.1% w/w. In some embodiments, the chlorite salt, e.g., sodium chlorite, is present in the pharmaceutical composition in an amount ranging from about 0.0001% to about 0.01% w/w. In some embodiments, the chlorite salt, e.g., sodium chlorite, is present in the pharmaceutical composition in an amount ranging from about 0.0001% to about 0.005% w/w. In some embodiments, the chlorite salt, e.g., sodium chlorite, is present in the pharmaceutical composition in an amount ranging from about 0.0001% to about 0.001% w/w. In some embodiments, the chlorite salt, e.g., sodium chlorite, is present in the pharmaceutical composition in an amount ranging from about 0.0001% to about 0.0005% w/w. In some embodiments, the chlorite salt, e.g., sodium chlorite, is present in the pharmaceutical composition in an amount of about 0.0003% w/w. In some embodiments, the chlorite salt, e.g., sodium chlorite, is present in the pharmaceutical composition in an amount of about 0.0006% w/w.

In some embodiments, the chlorite salt, e.g., sodium chlorite, is present in the pharmaceutical composition in an amount ranging from about 0.0001% to about 10% w/w. In some embodiments, the chlorite salt, e.g., sodium chlorite, is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.005%, about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, or about 10% w/w. In some embodiments, the chlorite salt, e.g., sodium chlorite, is present in the pharmaceutical composition in an amount ranging from about 0.0001% to about 5% w/w. In some embodiments, the chlorite salt, e.g., sodium chlorite, is present in the pharmaceutical composition in an amount ranging from about 0.0001% to about 4% w/w. In some embodiments, the chlorite salt, e.g., sodium chlorite, is present in the pharmaceutical composition in an amount ranging from about 0.0001% to about 3% w/w. In some embodiments, the chlorite salt, e.g., sodium chlorite, is present in the pharmaceutical composition in an amount ranging from about 0.0001% to about 2% w/w. In some embodiments, the chlorite salt, e.g., sodium chlorite, is present in the pharmaceutical composition in an amount ranging from about 0.0001% to about 1% w/w. In some embodiments, the chlorite salt, e.g., sodium chlorite, is present in the pharmaceutical composition in an amount ranging from about 0.0001% to about 0.1% w/w. In some embodiments, the chlorite salt, e.g., sodium chlorite, is present in the pharmaceutical composition in an amount ranging from about 0.0001% to about 0.01% w/w. In some embodiments, the chlorite salt, e.g., sodium chlorite, is present in the pharmaceutical composition in an amount ranging from about 0.0001% to about 0.001% w/w. In some embodiments, the chlorite salt, e.g., sodium chlorite, is present in the pharmaceutical composition in an amount ranging from about 0.001% to about 5% w/w. In some embodiments, the chlorite salt, e.g., sodium chlorite, is present in the pharmaceutical composition in an amount ranging from about 0.001% to about 4% w/w. In some embodiments, the chlorite salt, e.g., sodium chlorite, is present in the pharmaceutical composition in an amount ranging from about 0.001% to about 3% w/w. In some embodiments, the chlorite salt, e.g., sodium chlorite, is present in the pharmaceutical composition in an amount ranging from about 0.001% to about 2% w/w. In some embodiments, the chlorite salt, e.g., sodium chlorite, is present in the pharmaceutical composition in an amount ranging from about 0.001% to about 1% w/w. In some embodiments, the chlorite salt, e.g., sodium chlorite, is present in the pharmaceutical composition in an amount ranging from about 0.001% to about 0.1% w/w. In some embodiments, the chlorite salt, e.g., sodium chlorite, is present in the pharmaceutical composition in an amount ranging from about 0.001% to about 0.01% w/w. In some embodiments, the chlorite salt, e.g., sodium chlorite, is present in the pharmaceutical composition in an amount ranging from about 0.01% to about 5% w/w. In some embodiments, the chlorite salt, e.g., sodium chlorite, is present in the pharmaceutical composition in an amount ranging from about 0.01% to about 4% w/w. In some embodiments, the chlorite salt, e.g., sodium chlorite, is present in the pharmaceutical composition in an amount ranging from about 0.01% to about 3% w/w. In some embodiments, the chlorite salt, e.g., sodium chlorite, is present in the pharmaceutical composition in an amount ranging from about 0.01% to about 2% w/w. In some embodiments, the chlorite salt, e.g., sodium chlorite, is present in the pharmaceutical composition in an amount ranging from about 0.01% to about 1% w/w. In some embodiments, the chlorite salt, e.g., sodium chlorite, is present in the pharmaceutical composition in an amount ranging from about 0.01% to about 0.1% w/w. In some embodiments, the chlorite salt, e.g., sodium chlorite, is present in the pharmaceutical composition in an amount ranging from about 0.001% to about 5% w/w. In some embodiments, the chlorite salt, e.g., sodium chlorite, is present in the pharmaceutical composition in an amount ranging from about 0.01% to about 5% w/w. In some embodiments, the chlorite salt, e.g., sodium chlorite, is present in the pharmaceutical composition in an amount ranging from about 0.1% to about 5% w/w. In some embodiments, the chlorite salt, e.g., sodium chlorite, is present in the pharmaceutical composition in an amount ranging from about 1% to about 5% w/w. In some embodiments, the chlorite salt, e.g., sodium chlorite, is present in the pharmaceutical composition in an amount ranging from about 2% to about 5% w/w. In some embodiments, the chlorite salt, e.g., sodium chlorite, is present in the pharmaceutical composition in an amount ranging from about 3% to about 5% w/w. In some embodiments, the chlorite salt, e.g., sodium chlorite, is present in the pharmaceutical composition in an amount ranging from about 4% to about 5% w/w. In some embodiments, the chlorite salt, e.g., sodium chlorite, is present in the pharmaceutical composition in an amount ranging from about 0.001% to about 4% w/w. In some embodiments, the chlorite salt, e.g., sodium chlorite, is present in the pharmaceutical composition in an amount ranging from about 0.01% to about 4% w/w. In some embodiments, the chlorite salt, e.g., sodium chlorite, is present in the pharmaceutical composition in an amount ranging from about 0.1% to about 4% w/w. In some embodiments, the chlorite salt, e.g., sodium chlorite, is present in the pharmaceutical composition in an amount ranging from about 1% to about 4% w/w. In some embodiments, the chlorite salt, e.g., sodium chlorite, is present in the pharmaceutical composition in an amount ranging from about 2% to about 4% w/w. In some embodiments, the chlorite salt, e.g., sodium chlorite, is present in the pharmaceutical composition in an amount ranging from about 3% to about 4% w/w. In some embodiments, the chlorite salt, e.g., sodium chlorite, is present in the pharmaceutical composition in an amount ranging from about 0.001% to about 3% w/w. In some embodiments, the chlorite salt, e.g., sodium chlorite, is present in the pharmaceutical composition in an amount ranging from about 0.01% to about 3% w/w. In some embodiments, the chlorite salt, e.g., sodium chlorite, is present in the pharmaceutical composition in an amount ranging from about 0.1% to about 3% w/w. In some embodiments, the chlorite salt, e.g., sodium chlorite, is present in the pharmaceutical composition in an amount ranging from about 1% to about 3% w/w. In some embodiments, the chlorite salt, e.g., sodium chlorite, is present in the pharmaceutical composition in an amount ranging from about 2% to about 3% w/w. In some embodiments, the chlorite salt, e.g., sodium chlorite, is present in the pharmaceutical composition in an amount ranging from about 0.001% to about 2% w/w. In some embodiments, the chlorite salt, e.g., sodium chlorite, is present in the pharmaceutical composition in an amount ranging from about 0.01% to about 2% w/w. In some embodiments, the chlorite salt, e.g., sodium chlorite, is present in the pharmaceutical composition in an amount ranging from about 0.1% to about 2% w/w. In some embodiments, the chlorite salt, e.g., sodium chlorite, is present in the pharmaceutical composition in an amount ranging from about 1% to about 2% w/w. In some embodiments, the chlorite salt, e.g., sodium chlorite, is present in the pharmaceutical composition in an amount ranging from about 0.001% to about 1% w/w. In some embodiments, the chlorite salt, e.g., sodium chlorite, is present in the pharmaceutical composition in an amount ranging from about 0.01% to about 1% w/w. In some embodiments, the chlorite salt, e.g., sodium chlorite, is present in the pharmaceutical composition in an amount ranging from about 0.1% to about 1% w/w.

In some aspects, the pharmaceutical composition described herein comprises stabilized chlorine dioxide as a source of sodium chlorite. As used herein "stabilized chlorine dioxide" refers to an aqueous sodium chlorite ($NaClO_2$) solution. In some embodiments, stabilized chlorine dioxide is prepared by buffering sodium chlorite with a carbonate or a phosphate, and hydrogen peroxide. In some embodiments, stabilized chlorine dioxide further comprises sodium chlorate ($NaClO_3$). In some embodiments, stabilized chlorine dioxide further comprises sodium chloride (NaCl). In some embodiments, stabilized chlorine dioxide is commercially available and comprises from about 2% to about 4% sodium chlorite. In some embodiments, stabilized chlorine dioxide is commercially available and comprises about 3% sodium chlorite. In some embodiments and under the right pH conditions, stabilized chlorine dioxide further comprises chlorine dioxide ($ClO_2$). In some embodiments, the oxychlorine-based component of the composition described herein (e.g. sodium chlorite, stabilized chlorine dioxide, or chlorine dioxide) inhibits the cellular protein synthesis. In some embodiments, the oxychlorine-based component of the composition described herein (e.g. sodium chlorite, stabilized chlorine dioxide, or chlorine dioxide) inhibits the destruction of disulfide bonds. In some embodiments, the stabilized chlorine dioxide is present in the pharmaceutical composition in an amount ranging from about 0.005% to about 1% w/w. In some embodiments, the stabilized chlorine dioxide is present in the pharmaceutical composition in an amount of about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% w/w. In some embodiments, the stabilized chlorine dioxide is present in the pharmaceutical composition in an amount ranging from about 0.005% to about 0.1% w/w. In some embodiments, the stabilized chlorine dioxide is present in the pharmaceutical composition in an amount ranging from about 0.01% to about 0.1% w/w. In some embodiments, the stabilized chlorine dioxide is present in the pharmaceutical composition in an amount ranging from about 0.005% to about 0.01% w/w. In some embodiments, the stabilized chlorine dioxide is present in the pharmaceutical composition in an amount ranging from about 0.009% to about 0.011% w/w. In some embodiments, the stabilized chlorine dioxide is present in the pharmaceutical composition in an amount of about 0.01% w/w. In some embodiments, the stabilized chlorine dioxide is present in the pharmaceutical composition in an amount of about 0.02% w/w.

In some embodiments, the stabilized chlorine dioxide is present in the pharmaceutical composition in an amount ranging from about 0.0001% to about 10% w/w. In some embodiments, the stabilized chlorine dioxide is present in the pharmaceutical composition in an amount ranging from about 0.0001%, about 0.0002%, about 0.0003%, about 0.0004%, about 0.0005%, about 0.0006%, about 0.0007%, about 0.0008%, about 0.0009%, about 0.001%, about 0.005%, about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, or about 10% w/w. In some embodiments, the stabilized chlorine dioxide is present in the pharmaceutical composition in an amount ranging from about 0.0001% to about 5% w/w. In some embodiments, the stabilized chlorine dioxide is present in the pharmaceutical composition in an amount ranging from about 0.0001% to about 4% w/w. In some embodiments, the stabilized chlorine dioxide is present in the pharmaceutical composition in an amount ranging from about 0.0001% to about 3% w/w. In some embodiments, the stabilized chlorine dioxide is present in the pharmaceutical composition in an amount ranging from about 0.0001% to about 2% w/w. In some embodiments, the stabilized chlorine dioxide is present in the pharmaceutical composition in an amount ranging from about 0.0001% to about 1% w/w. In some embodiments, the stabilized chlorine dioxide is present in the pharmaceutical composition in an amount ranging from about 0.0001% to about 0.1% w/w. In some embodiments, the stabilized chlorine dioxide is present in the pharmaceutical composition in an amount ranging from about 0.0001% to about 0.01% w/w. In some embodiments, the stabilized chlorine dioxide is present in the pharmaceutical composition in an amount ranging from about 0.0001% to about 0.001% w/w. In some embodiments, the stabilized chlorine dioxide is present in the pharmaceutical composition in an amount ranging from about 0.001% to about 5% w/w. In some embodiments, the stabilized chlorine dioxide is present in the pharmaceutical composition in an amount ranging from about 0.001% to about 4% w/w. In some embodiments, the stabilized chlorine dioxide is present in the pharmaceutical composition in an amount ranging from about 0.001% to about 3% w/w. In some embodiments, the stabilized chlorine dioxide is present in the pharmaceutical composition in an amount ranging from about 0.001% to about 2% w/w. In some embodiments, the stabilized chlorine dioxide is present in the pharmaceutical composition in an amount ranging from about 0.001% to about 1% w/w. In some embodiments, the stabilized chlorine dioxide is present in the pharmaceutical composition in an amount ranging from about 0.001% to about 0.1% w/w. In some embodiments, the stabilized chlorine dioxide is present in the pharmaceutical composition in an amount ranging from about 0.001% to about 0.01% w/w. In some embodiments, the stabilized chlorine dioxide is present in the pharmaceutical composition in an amount ranging from about 0.01% to about 5% w/w. In some embodiments, the stabilized chlorine dioxide is present in the pharmaceutical composition in an amount ranging from about 0.01% to about 4% w/w. In some embodiments, the stabilized chlorine dioxide is present in the pharmaceutical composition in an amount ranging from about 0.01% to about 3% w/w. In some embodiments, the stabilized chlorine dioxide is present in the pharmaceutical composition in an amount ranging from about 0.01% to about 2% w/w. In some embodiments, the stabilized chlorine dioxide is present in the pharmaceutical composition in an amount ranging from about 0.01% to about 1% w/w. In some embodiments, the stabilized chlorine dioxide is present in the pharmaceutical composition in an amount ranging from about 0.01% to about 0.1% w/w. In some embodiments, the stabilized chlorine dioxide is present in the pharmaceutical composition in an amount ranging from about 0.001% to about 5% w/w. In some embodiments, the stabilized chlorine dioxide is present in the pharmaceutical composition in an amount ranging from about 0.01% to about 5% w/w. In some embodiments, the stabilized chlorine dioxide is present in the pharmaceutical composition in an amount ranging from about 0.1% to about 5% w/w. In some embodiments, the stabilized chlorine dioxide is present in the pharmaceutical composition in an amount ranging from about 1% to about 5% w/w. In some embodiments, the stabilized chlorine dioxide is present in the pharmaceutical composition in an amount ranging from about 2% to about 5% w/w. In some embodiments, the stabilized chlorine dioxide is present in the pharmaceutical composition in an amount ranging from about 3% to about 5% w/w. In some embodiments, the stabilized chlorine dioxide is present in the pharmaceutical composition in an amount ranging from about 4% to about 5% w/w. In some embodiments, the stabilized chlorine dioxide is present in the pharmaceutical composition in an amount ranging from about 0.001% to about 4% w/w. In some embodiments, the stabilized chlorine dioxide is present in the pharmaceutical composition in an amount ranging from about 0.01% to about 4% w/w. In some embodiments, the stabilized chlorine dioxide is present in the pharmaceutical composition in an amount ranging from about 0.1% to about 4% w/w. In some embodiments, the stabilized chlorine dioxide is present in the pharmaceutical composition in an amount ranging from about 1% to about 4% w/w. In some embodiments, the stabilized chlorine dioxide is present in the pharmaceutical composition in an amount ranging from about 2% to about 4% w/w. In some embodiments, the stabilized chlorine dioxide is present in the pharmaceutical composition in an amount ranging from about 3% to about 4% w/w. In some embodiments, the stabilized chlorine dioxide is present in the pharmaceutical composition in an amount ranging from about 0.001% to about 3% w/w. In some embodiments, the stabilized chlorine dioxide is present in the pharmaceutical composition in an amount ranging from about 0.01% to about 3% w/w. In some embodiments, the stabilized chlorine dioxide is present in the pharmaceutical composition in an amount ranging from about 0.1% to about 3% w/w. In some embodiments, the stabilized chlorine dioxide is present in the pharmaceutical composition in an amount ranging from about 1% to about 3% w/w. In some embodiments, the stabilized chlorine dioxide is present in the pharmaceutical composition in an amount ranging from about 2% to about 3% w/w. In some embodiments, the stabilized chlorine dioxide is present in the pharmaceutical composition in an amount ranging from about 0.001% to about 2% w/w. In some embodiments, the stabilized chlorine dioxide is present in the pharmaceutical composition in an amount ranging from about 0.01% to about 2% w/w. In some embodiments, the stabilized chlorine dioxide is present in the pharmaceutical composition in an amount ranging from about 0.1% to about 2% w/w. In some embodiments, the stabilized chlorine dioxide is present in the pharmaceutical composition in an amount ranging from about 1% to about 2% w/w. In some embodiments, the stabilized chlorine dioxide is present in the pharmaceutical composition in an amount ranging from about 0.001% to about 1% w/w. In some embodiments, the stabilized chlorine dioxide is present in the pharmaceutical composition in an amount ranging from about 0.01% to about 1% w/w. In some embodiments, the stabilized chlorine dioxide is present in the pharmaceutical composition in an amount ranging from about 0.1% to about 1% w/w.

Dosage Forms

Disclosed herein are dosage forms that are applied topically. In some embodiments, the pharmaceutical composition is applied topically to the skin or a mucous membrane. In some embodiments, the mucous membrane comprises the lips, the nostrils, the urethra, the vagina, the foreskin, or the anus. In some embodiments, the pharmaceutical composition is applied directly to the lesions associated with the infection.

In some aspects, the pharmaceutical composition is in the form of an aerosol, a solution, a lotion, a gel, an ointment, a cream, a foam, a paste, or any combinations thereof. In some embodiments, the pharmaceutical composition is in the form of irrigation for nasal and sinus passages. In some embodiments, the pharmaceutical composition is in the form of an inhalation. In some embodiments, the pharmaceutical composition is in the form of an ophthalmic composition for administration into the eye. In some embodiments, the pharmaceutical composition in the form of a coated strip or an impregnated bandage. Exemplary dosage forms of the disclosure include those found in Remington: The Science and Practice of Pharmacy, Twenty Second Ed. (London, UK: Pharmaceutical Press, 2013) incorporated herein by reference for such disclosure.

In some embodiments, the pharmaceutical composition in the form of a solution, a gel, an ointment, a cream, a foam, a paste, or any combinations thereof, further comprises pharmaceutically acceptable excipients including, viscosity agents, gelling agents, preservatives, oils, penetration enhancers, surfactants, stabilizers, moisturizers, tonicity agents, extended release agents, water, and any combinations thereof thereof.

Penetration enhancers include vitamin E TPGS (Eastman Chemical Company, Kingsport, Tenn.), and other vitamin E derivatives as described in U.S. Pat. No. 6,193,985; and glyceryl monocaprylate/caprate (Cornwell et al. 1998, Int. J. Pharmaceutics, 171(2): 243-255). In some embodiments, additional penetration enhancers are described in Smith and Maibach (eds.), Percutaneous Penetration Enhancers, CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, I. L. (1997).

In some embodiments, the oils and/or waxy compounds in the pharmaceutical composition are those traditionally employed in the dermatological arts. In some embodiments, the optional oils and/or waxy compounds constitute from 0.5% to 99.9% of the total weight of the composition. The amount of oil and/or wax depends on the actual form or physical state of the composition. Exemplary of such oils are mineral oils (petrolatum); vegetable oils (sweet almond, macadamia, blackcurrant-pip oil); synthetic oils such as perhydrosqualene, fatty alcohols, acids or esters (octyl palmitate, isopropyl lanolate, triglycerides including those of capric/caprylic acids), oxyethylenated or oxypropylenated fatty esters and ethers; and silicone oils (cyclomethicone, polydimethylsiloxanes or PDMS) or fluorinated oils. Exemplary waxy compounds include jojoba oil, paraffin, carnauba wax and beeswax.

Exemplary surfactants (emulsifying and coemulsifying) present in the pharmaceutical composition include the esters of fatty acids and polyethylene glycol (PEG), esters of fatty acids and glycerol (glyceryl stearate) or esters of fatty acids and sugar (sorbitan stearate), as well as the polyoxyethylenated or polyoxypropylenated derivatives thereof, cyclomethicones and dimethicone copolyols, and also anionic surfactants (K or Na alkyl phosphate). In some embodiments, the surfactant is a cationic surfactant. In some embodiments, the surfactant is a zwitterionic surfactant. In some embodiments, the surfactant is a nonionic surfactant. In some embodiments, the surfactant is selected from sodium lauryl sulfate, docusate sodium, polyoxyalkyl ethers, polyoxylalkyl phenyl ethers, polyoxyl castor oils, polyoxyl hydrogenated castor oils, polyoxyl 40 stearates, polyoxy sorbitan esters, sorbitan esters, polysorbates, sorbitan monolaureates, poloxamines, poloxamers, sucrose stearate, sucrose distearate, and any combinations thereof. In some embodiments, the surfactant is a polyoxyethylene-polyoxypropylene block copolymer. In some embodiments, the surfactant is a poloxamer. In some embodiments, the surfactant is a poloxamine. In some embodiments, the surfactant is Tetronic® 908. The surfactant, when used, is typically present in an amount from about 0.01 to 5 weight percent of the composition.

Exemplary stabilizer includes glycol stearate or PEG-150 distearate. The stabilizer, when used, is typically present in an amount from about 0.1 to 5 weight percent of the composition.

Exemplary moisturizers include wheat protein (e.g., laurdimonium hydroxypropyl hydrolyzed wheat protein), hair keratin amino acids, sodium peroxylinecarbolic acid, panthenol, tocopherol (Vitamin E), dimethicone, and the like, and mixtures thereof. Sodium chloride may also be present, particularly when hair keratin amino acids are included as a moisturizer. Moisturizers, when used, are typically present in an amount from about 0.01 to 2 weight percent of the pharmaceutical composition.

Exemplary preservatives include benzyl alcohol, benzalkonium chloride, tetrasodium ethylene-diamine tetraacetic acid (EDTA), methylparaben, propylparaben, benzophenone-4, methylchloroisothiazolinone, methylisothiazolinone, benzethonium chloride, chlorobutanol, phenylmercuric acetate, phenylmercuric nitrate, thimerosal, and any combinations thereof. In some embodiments, the preservative used does not cause patient sensitivity or is not incompatible with the other ingredients in the pharmaceutical composition. Preservatives, when used, are typically present in an amount from about 0.01% to about 10% by weight of the pharmaceutical composition.

Exemplary tonicity agents include sodium chloride, potassium chloride, propylene glycol, dextrose, glycerin, and mannitol.

In some embodiments, the pharmaceutical composition further comprises benzyl alcohol, mineral oil, propylene glycol, sucrose stearate, and sucrose distearate.

In some embodiments, the pharmaceutical composition further comprises cyclomethicone, polyethylene glycol 600, dimethicone, silica, petrolatum, phenyl trimethicone, PEG/PPG-19/20 dimethicone, mica, PEG 12 dimethicone, titanium dioxide, polyurethane-40, menthol, and tin oxide.

Gel Compositions

In some embodiments, the pharmaceutical composition described herein is formulated as a gel. Gels have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a non-limiting example of a hydrophobic gel includes liquid paraffin with polyethylene or fatty oils gelled with colloidal silica, or aluminum or zinc soaps. The base of a non-limiting example of a hydrophilic gel includes water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions disclosed herein is pseudo plastic, plastic, thixotropic, or dilatant.

In some embodiments, the pharmaceutical composition disclosed herein is a gel and comprises water and at least one viscosity-enhancing agent. In some embodiment the gel composition described herein is a semi-solid or is in a gelled state before it is topically administered (e.g. at room temperature). In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, and any combinations thereof. In some embodiments, suitable viscosity-enhancing agents include by way of example only, gelling agents and suspending agents. In some embodiments, the enhanced viscosity formulation includes a pharmaceutically acceptable buffer. Sodium chloride or other tonicity agents are optionally used to adjust tonicity, if necessary.

By way of example only, the viscosity-enhancing agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity-enhancing agents include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methylcellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In some embodiments, the viscosity-enhancing excipient is a combination of MCC and CMC. In another embodiment, the viscosity-enhancing agent is a combination of carboxymethylated chitosan, chitin, and alginate. In some embodiments, the viscosity-enhancing agent is a cellulose-based polymer selected from cellulose gum, alkylcellulose, hydroxyl-alkyl cellulose, hydroxyl-alkyl alkylcellulose, carboxy-alkyl cellulose, or combinations thereof. In some embodiments, the viscosity-enhancing agent is hydroxyl-alkyl alkylcellulose. In some embodiment, the viscosity-enhancing agent is hydroxypropyl methylcellulose.

In one embodiment, the pharmaceutically acceptable enhanced viscosity acceptable formulation comprises at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In some other embodiments, methylcellulose is utilized as the gelling agent. In certain embodiments, the viscosity enhancing agents described herein are also utilized as the gelling agent for the gel formulations presented herein.

In some embodiments, other gel formulations are useful depending upon the pharmaceutical agents or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the pharmaceutical compositions described herein. In some embodiments, acceptable gels include, but are not limited to, alginate hydrogels SAF®-Gel (ConvaTec, Princeton, N.J.), Duoderm® Hydroactive Gel (ConvaTec), Nu-gel®(Johnson & Johnson Medical, Arlington, Tex.); Carrasyn®(V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in the pharmaceutical compositions described herein.

In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. Included within the definition of body temperature is the body temperature of a healthy individual, or an unhealthy individual, including an individual with a fever (up to ~42° C.). In some embodiments, the pharmaceutical compositions described herein are liquids at about room temperature and are administered at or about room temperature.

Copolymers polyoxypropylene and polyoxyethylene (e.g. polyoxyethylene-polyoxypropylene triblock copolymers) form thermosetting gels when incorporated into aqueous solutions. These polymers have the ability to change from the liquid state to the gel state at temperatures close to body temperature, therefore allowing useful formulations that are applied to the targeted site. The liquid state-to-gel state phase transition is dependent on the polymer concentration and the ingredients in the solution.

In some embodiments, the amount of thermosetting polymer in any formulation described herein is about 10%, about 15%, about 20%, about 25%, about 30%, about 35% or about 40% of the total weight of the formulation. In some embodiments, the amount of thermosetting polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermosetting polymer (e.g., Poloxamer 407) in any formulation described herein is about 7.5% of the total weight of the formulation. In some embodiments, the amount of thermosetting polymer (e.g., Poloxamer 407) in any formulation described herein is about 10% of the total weight of the formulation. In some embodiments, the amount of thermosetting polymer (e.g., Poloxamer 407) in any formulation described herein is about 11% of the total weight of the formulation. In some embodiments, the amount of thermosetting polymer (e.g., Poloxamer 407) in any formulation described herein is about 12% of the total weight of the formulation. In some embodiments, the amount of thermosetting polymer (e.g., Poloxamer 407) in any formulation described herein is about 13% of the total weight of the formulation. In some embodiments, the amount of thermosetting polymer (e.g., Poloxamer 407) in any formulation described herein is about 14% of the total weight of the formulation. In some embodiments, the amount of thermosetting polymer (e.g., Poloxamer 407) in any formulation described herein is about 15% of the total weight of the formulation. In some embodiments, the amount of thermosetting polymer (e.g., Poloxamer 407) in any formulation described herein is about 16% of the total weight of the formulation. In some embodiments, the amount of thermosetting polymer (e.g., Poloxamer 407) in any formulation described herein is about 17% of the total weight of the formulation. In some embodiments, the amount of thermosetting polymer (e.g., Poloxamer 407) in any formulation described herein is about 18% of the total weight of the formulation. In some embodiments, the amount of thermosetting polymer (e.g., Poloxamer 407) in any formulation described herein is about 19% of the total weight of the formulation. In some embodiments, the amount of thermosetting polymer (e.g., Poloxamer 407) in any formulation described herein is about 20% of the total weight of the formulation. In some embodiments, the amount of thermosetting polymer (e.g., Poloxamer 407) in any formulation described herein is about 21% of the total weight of the formulation. In some embodiments, the amount of thermosetting polymer (e.g., Poloxamer 407) in any formulation described herein is about 23% of the total weight of the formulation. In some embodiments, the amount of thermosetting polymer (e.g., Poloxamer 407) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PLGA copolymer of 50:50 poly(DL-lactide-co-glycolide) and is 10% w/w of PEG and has a molecular weight of about 6000.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermosetting gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermosetting gel polymer. The active agents and various additives such as buffers, salts, and preservatives are subsequently added and dissolved. In some instances the pharmaceutically agent is suspended if it is insoluble in water. The pH is modulated by the addition of appropriate buffering agents.

Ointment Compositions

In some embodiments, the pharmaceutical composition described herein is formulated as an ointment. An ointment is a homogeneous, viscous, semi-solid preparation, most commonly a greasy, thick oil (e.g. oil 80%-water 20%) with a high viscosity, intended for topical application to the skin or mucous membranes. Ointments have a Water number that defines the maximum amount of water that it can contain. They are used as emollients or for the application of active ingredients to the skin for protective, therapeutic, or prophylactic purposes and where a degree of occlusion is desired. Ointments are used topically on a variety of body surfaces. These include the skin and the mucous membranes.

The vehicle of an ointment is known as the ointment base. The choice of a base depends upon the clinical indication for the ointment. The different types of ointment bases are: hydrocarbon bases, e.g. hard paraffin, soft paraffin, microcrystalline wax and ceresine; absorption bases, e.g. wool fat, beeswax; water soluble bases, e.g. macrogols 200, 300, 400; emulsifying bases, e.g. emulsifying wax, cetrimide; vegetable oils, e.g. olive oil, coconut oil, sesame oil, almond oil and peanut oil.

Ointments are formulated using hydrophobic, hydrophilic, or water-emulsifying bases to provide preparations that are immiscible, miscible, or emulsifiable with skin secretions. They can also be derived from hydrocarbon (fatty), absorption, water-removable, or water-soluble bases. The active agents are dispersed in the base, and later they get divided after the drug penetration into the target sites (e.g. mucous membranes, skins, etc.).

The present disclosure recognizes that it is sometimes difficult to incorporate into the ointment a drug of low concentration with sufficient dose-to-dose uniformity for effectively treating a disorder or disease. In some embodiments, poly(ethylene-glycols), polyethoxylated castor oils (Cremophor®EL), alcohols having 12 to 20 carbon atoms or a mixture of two or more of said components are effective excipients for dispersing and/or dissolving effective amounts of active agents, in an ointment base, in particular in an ointment base substantially comprising oleaginous and hydrocarbon components, and that the resulting ointments are excellently tolerated by the skin.

In some embodiments, the ointment bases include pharmaceutically acceptable oil and fat bases, such as natural wax e.g. white and yellow bees wax, carnauba wax, wool wax (wool fat), purified lanolin, anhydrous lanolin; petroleum wax e.g. hard paraffin, microcrystalline wax; hydrocarbons e.g. liquid paraffin, white and yellow soft paraffin, white petrolatum, yellow petrolatum; or combinations thereof.

The above mentioned oil and fat bases are described in more detail, for instance, in the British Pharmacopoeia, Edition 2001, or the European Pharmacopoeia, 3rd Edition.

In some embodiments, the ointment base is present in amounts of about 50% to about 95%, preferably of about 70% to about 90% by weight based on the total weight of the composition.

Alcohols having 12 to 20 carbon atoms include particularly stearyl alcohol ($C_{18}H_{37}OH$), cetyl alcohol ($C_{16}H_{33}OH$) and mixtures thereof. Preferred are so-called cetostearyl alcohols, mixtures of solid alcohols substantially consisting of stearyl and cetyl alcohol and preferably comprising not less than 40 percent by weight of stearyl alcohol and a sum of stearyl alcohol and cetyl alcohol amounting to at least 90 percent by weight, and compositions comprising not less than 80 percent by weight of cetylstearyl alcohol and an emulsifier, in particular sodium cetostearyl sulfate and/or sodium lauryl sulfate, preferably in amounts not less than 7% by weight of emulsifier.

Polyethoxylated castor oils are reaction products of natural or hydrogenated castor oils and ethylene glycol. Such products may be obtained in known manner, e.g. by reaction of a natural or hydrogenated castor oil or fractions thereof with ethylene oxide, e.g. in a molar ratio of from about 1:30 to about 1:60. Especially suitable and preferred is a product commercially available under the trade name Cremophor®EL having a molecular weight (by steam osmometry)=ca. 1630, a saponification no.=ca. 65-70, an acid no.=ca. 2, an iodine no.=ca. 28-32 and an nD 25=ca.1.471. Also suitable for use in this category is, for instance, Nikkol®HCO-60, a reaction product of hydrogenated castor oil and ethylene oxide exhibiting the following characteristics: acid no.=ca. 0.3; saponification no.=ca. 47.4; hydroxy value=ca. 42.5. pH (5%)=ca. 4.6; Color APHA=ca. 40; m.p.=ca. 36.0° C.; Freezing point=ca. 32.4° C.; $H_2O$ content (%, KF)=ca. 0.03.

Poly(ethylene-glycols) are used in some embodiments as the agent for dispersing and/or dissolving the active agents in the ointment base according to the present invention. Suitable poly(ethylene-glycol)s are typically mixtures of polymeric compounds of the general formula H—($OCH_2$—$CH_2$)nOH, wherein the index n may typically range from 4 to 230 and the mean molecular weight from about 200 to about 10000. Preferably n is a number from about 6 to about 22 and the mean molecular weight between about 300 and about 1000, more preferably n ranges from about 6 to about 13 and the mean molecular weight from about 300 to about 600, most preferably n has a value of about 8.5 to about 9 and the relative molecular weight is about 400. Suitable poly(ethylene-glycols) are readily available commercially, for example poly(ethylene-glycols) having a mean molecular weight of about 200, 300, 400, 600, 1000, 1500, 2000, 3000, 4000, 6000, 8000 and 10000.

The poly(ethylene-glycols), in particular the preferred types described in the foregoing paragraph, are preferably used in amounts of 1 to 10, more preferably 1 to 5 percent by weight of the entire semisolid composition.

An especially preferred embodiment of the compositions according to the instant invention comprises an agent for dispersing and/or dissolving of the drug in the ointment base which is selected from a poly(ethylene-glycol), a polyethoxylated castor oil and preferably a mixture of said components.

Viscosity

In some embodiments, the pharmaceutical composition disclosed herein has a Brookfield RVDV viscosity of from about 10,000 to about 300,000 cps at about 20° C. and sheer rate of 1 $s^{-1}$. In some embodiments, the pharmaceutical composition disclosed herein has a Brookfield RVDV viscosity of from about 15,000 to about 200,000 cps at about 20° C. and sheer rate of 1 $s^1$. In some embodiments, the pharmaceutical composition disclosed herein has a Brookfield RVDV viscosity of from about 50,000 to about 150,000 cps at about 20° C. and sheer rate of 1 $s^{-1}$. In some embodiments, the pharmaceutical composition disclosed herein has a Brookfield RVDV viscosity of from about 70,000 to about 130,000 cps at about 20° C. and sheer rate of 1 s$^{-1}$. In some embodiments, the pharmaceutical composition disclosed herein has a Brookfield RVDV viscosity of from about 90,000 to about 110,000 cps at about 20° C. and sheer rate of 1 s$^1$.

In some embodiments, the pharmaceutical composition disclosed herein contains a viscosity enhancing agent sufficient to provide a viscosity between about 500 and about 1,000,000 centipoise, between about 750 and about 1,000,000 centipoise; between about 1000 and about 1,000,000 centipoise; between about 1000 and about 400,000 centipoise; between about 2000 and about 100,000 centipoise; between about 3000 and about 50,000 centipoise; between about 4000 and about 25,000 centipoise; between about about 5000 and about 20,000 centipoise; or between about 6000 and about 15,000 centipoise. In some embodiments, the pharmaceutical composition disclosed herein contains a viscosity enhancing agent sufficient to provide a viscosity of between about 50,0000 and about 1,000,000 centipoise.

In some embodiments, a viscous composition described herein provides an apparent viscosity of from about 100,000 cP to about 1,000,000 cP. In some embodiments, a viscous composition described herein provides an apparent viscosity from about 150,000 cP to about 500,000 cP. In some embodiments, a viscous composition described herein provides an apparent viscosity from about 250,000 cP to about 500,000 cP.

In some embodiments, the viscosity of the pharmaceutical composition disclosed herein is measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

Stability

Disclosed herein are stable pharmaceutical compositions. The pharmaceutical compositions described herein are stable in various storage conditions including refrigerated, ambient, and accelerated conditions.

In some embodiments, stable as used herein refers to a pharmaceutical composition having about 5% w/w or less total impurities at the end of a given storage period. Stability is assessed by HPLC or any other known testing method. In some embodiments, the stable pharmaceutical composition has about 5% w/w, about 4% w/w, about 3% w/w, about 2.5% w/w, about 2% w/w, about 1.5% w/w, about 1% w/w, or about 0.5% w/w total impurities at the end of a given storage period. In other embodiments, the pharmaceutical composition has about 5% w/w total impurities. In yet other embodiments, the pharmaceutical composition has about 4% w/w total impurities. In yet other embodiments, pharmaceutical composition has about 3% w/w total impurities. In yet other embodiments, the pharmaceutical composition has about 2% w/w total impurities. In yet other embodiments, the pharmaceutical composition has about 1% w/w total impurities. In yet other embodiments, the pharmaceutical composition has about 0.9% w/w total impurities. In yet other embodiments, the pharmaceutical composition has about 0.8% w/w total impurities. In yet other embodiments, the pharmaceutical composition has about 0.7% w/w total impurities. In yet other embodiments, the pharmaceutical composition has about 0.6% w/w total impurities. In yet other embodiments, the pharmaceutical composition has about 0.5% w/w total impurities. In yet other embodiments, the pharmaceutical composition has about 0.4% w/w total impurities. In yet other embodiments, the pharmaceutical composition has about 0.3% w/w total impurities. In yet other embodiments, the pharmaceutical composition has about 0.2% w/w total impurities. In yet other embodiments, the pharmaceutical composition has about 0.1% w/w total impurities. In yet other embodiments, the pharmaceutical composition has about 0.09% w/w total impurities. In yet other embodiments, the pharmaceutical composition has about 0.08% w/w total impurities. In yet other embodiments, the pharmaceutical composition has about 0.07% w/w total impurities. In yet other embodiments, the pharmaceutical composition has about 0.06% w/w total impurities. In yet other embodiments, the pharmaceutical composition has about 0.05% w/w total impurities. In yet other embodiments, the pharmaceutical composition has about 0.04% w/w total impurities. In yet other embodiments, the pharmaceutical composition has about 0.03% w/w total impurities. In yet other embodiments, the pharmaceutical composition has about 0.02% w/w total impurities. In yet other embodiments, the pharmaceutical composition has about 0.01% w/w total impurities. In some embodiments, at refrigerated condition, the pharmaceutical compositions described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, at accelerated conditions, the pharmaceutical compositions described herein are stable for at least 1 month, at least 2 months, at least 3 months, at least 4 months, at least 5 months, at least 6 months, at least 7 months, at least 8 months, at least 9 months, at least 10 months, at least 11 months, or at least 12 months.

In some embodiments, stable as used herein refers to a pharmaceutical composition having about 10% or less loss of biocidal activity at the end of a given storage period. Biocidal activity is assessed by known testing method. In some embodiments, the stable pharmaceutical composition has about 10%, about 9.5%, about 9%, about 8.5%, about 8%, about 7.5%, about 7%, about 6.5%, about 6%, about 5.5%, about 5%, about 4.5%, about 4%, about 3.5%, about 3%, about 2.5%, about 2%, about 1.5%, about 1%, or about 0.5% loss of biocidal activity at the end of a given storage period. In some embodiments, the stable pharmaceutical composition has zero loss of biocidal activity at the end of a given storage period. In some embodiments, at refrigerated condition, the pharmaceutical compositions described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, at accelerated conditions, the pharmaceutical compositions described herein are stable for at least 1 month, at least 2 months, at least 3 months, at least 4 months, at least 5 months, at least 6 months, at least 7 months, at least 8 months, at least 9 months, at least 10 months, at least 11 months, or at least 12 months.

In some embodiments, stable as used herein refers to a pharmaceutical composition having no sign of precipitation at the end of a given storage period. Precipitation is assessed by known testing method. In some embodiments, at refrigerated condition, the pharmaceutical compositions described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, at accelerated conditions, the pharmaceutical compositions described herein are stable for at least 1 month, at least 2 months, at least 3 months, at least 4 months, at least 5 months, at least 6 months, at least 7 months, at least 8 months, at least 9 months, at least 10 months, at least 11 months, or at least 12 months.

Methods of Reducing the Severity and Duration of an Infection

Also disclosed herein are methods of reducing the severity and duration of an infection in a subject in need thereof, the method comprising administering to the subject in need thereof a pharmaceutical composition described herein. In some embodiments of a method of reducing the severity and duration of an infection, the pharmaceutical composition comprises a quaternary ammonium salt. In some embodiments, the quaternary ammonium salt is C10-C16-alkyl(ethylbenzyl)dimethylammonium chloride. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the pharmaceutical composition further comprises ammonium chloride. In some embodiments, the pharmaceutical composition further comprises a chlorite salt.

In some embodiments of a method of reducing the severity and duration of an infection, the infection is a viral infection. In some embodiments of a method of reducing the severity and duration of an infection, the infection is caused by the herpes simplex virus. In some embodiments of a method of reducing the severity and duration of an infection, the herpes simplex virus is herpes simplex virus type 1 (HSV-1). In some embodiments of a method of reducing the severity and duration of an infection, the herpes simplex virus is herpes simplex virus type 2 (HSV-2). In some embodiments of a method of reducing the severity and duration of an infection, the infection caused by the herpes simplex virus is herpes labialis. In some embodiments of a method of reducing the severity and duration of an infection, the infection caused by the herpes simplex virus is genital herpes. In some embodiments of a method of reducing the severity and duration of an infection, the infection caused by the herpes simplex virus is herpetic simplex keratitis.

In some embodiments of a method of reducing the severity and duration of an infection, the infection is caused by the varicella zoster virus (VZV). In some embodiments of a method of reducing the severity and duration of an infection, the varicella zoster virus (VZV) is shingles.

In some embodiments of a method of reducing the severity and duration of an infection, the reduction in severity is assessed by visually inspecting the lesions associated with the infection. In some embodiments of a method of reducing the severity and duration of an infection, the number of lesions is about 2 times to about 10 times smaller as compared to a non-treated infection. In some embodiments of a method of reducing the severity and duration of an infection, the number of lesions is about 2 times smaller as compared to a non-treated infection. In some embodiments of a method of reducing the severity and duration of an infection, the number of lesions is about 3 times smaller as compared to a non-treated infection. In some embodiments of a method of reducing the severity and duration of an infection, the number of lesions is about 4 times smaller as compared to a non-treated infection. In some embodiments of a method of reducing the severity and duration of an infection, the number of lesions is about 5 times smaller as compared to a non-treated infection. In some embodiments of a method of reducing the severity and duration of an infection, the number of lesions is about 6 times smaller as compared to a non-treated infection. In some embodiments of a method of reducing the severity and duration of an infection, the number of lesions is about 7 times smaller as compared to a non-treated infection. In some embodiments of a method of reducing the severity and duration of an infection, the number of lesions is about 8 times smaller as compared to a non-treated infection. In some embodiments of a method of reducing the severity and duration of an infection, the number of lesions is about 9 times smaller as compared to a non-treated infection. In some embodiments of a method of reducing the severity and duration of an infection, the number of lesions is about 10 times smaller as compared to a non-treated infection.

In some embodiments of a method of reducing the severity and duration of an infection, the total lesion area is about 2 times to about 10 times smaller in size as compared to a non-treated infection. In some embodiments of a method of reducing the severity and duration of an infection, the total lesion area is about 2 times smaller in size as compared to a non-treated infection. In some embodiments of a method of reducing the severity and duration of an infection, the total lesion area is about 3 times smaller in size as compared to a non-treated infection. In some embodiments of a method of reducing the severity and duration of an infection, the total lesion area is about 4 times smaller in size as compared to a non-treated infection. In some embodiments of a method of reducing the severity and duration of an infection, the total lesion area is about 5 times smaller in size as compared to a non-treated infection. In some embodiments of a method of reducing the severity and duration of an infection, the total lesion area is about 6 times smaller in size as compared to a non-treated infection. In some embodiments of a method of reducing the severity and duration of an infection, the total lesion area is about 7 times smaller in size as compared to a non-treated infection. In some embodiments of a method of reducing the severity and duration of an infection, the total lesion area is about 8 times smaller in size as compared to a non-treated infection. In some embodiments of a method of reducing the severity and duration of an infection, the total lesion area is about 9 times smaller in size as compared to a non-treated infection. In some embodiments of a method of reducing the severity and duration of an infection, the total lesion area is about 10 times smaller in size as compared to a non-treated infection.

In some embodiments of a method of reducing the severity and duration of an infection, the reduction in severity is assessed by measuring the pain associated with the infection. In some embodiments of a method of reducing the severity and duration of an infection, the pain is about 2 times to about 10 times less as compared to a non-treated infection. In some embodiments of a method of reducing the severity and duration of an infection, the pain is about 2 times less as compared to a non-treated infection. In some embodiments of a method of reducing the severity and duration of an infection, the pain is about 3 times less as compared to a non-treated infection. In some embodiments of a method of reducing the severity and duration of an infection, the pain is about 4 times less as compared to a non-treated infection. In some embodiments of a method of reducing the severity and duration of an infection, the pain is about 5 times less as compared to a non-treated infection. In some embodiments of a method of reducing the severity and duration of an infection, the pain is about 6 times less as compared to a non-treated infection. In some embodiments of a method of reducing the severity and duration of an infection, the pain is about 7 times less as compared to a non-treated infection. In some embodiments of a method of reducing the severity and duration of an infection, the pain is about 8 times less as compared to a non-treated infection. In some embodiments of a method of reducing the severity and duration of an infection, the pain is about 9 times less as compared to a non-treated infection. In some embodiments of a method of reducing the severity and duration of an infection, the pain is about 10 times less as compared to a non-treated infection.

In some embodiments of a method of reducing the severity and duration of an infection, the reduction in duration is assessed by visually inspecting the lesions associated with the infection. In some embodiments of a method of reducing the severity and duration of an infection, the lesions crust about 2 times to about 10 times faster or clear about 2 times to about 10 times faster as compared to a non-treated infection. In some embodiments of a method of reducing the severity and duration of an infection, the lesions crust about 2 times faster as compared to a non-treated infection. In some embodiments of a method of reducing the severity and duration of an infection, the lesions crust about 3 times faster as compared to a non-treated infection. In some embodiments of a method of reducing the severity and duration of an infection, the lesions crust about 4 times faster as compared to a non-treated infection. In some embodiments of a method of reducing the severity and duration of an infection, the lesions crust about 5 times faster as compared to a non-treated infection. In some embodiments of a method of reducing the severity and duration of an infection, the lesions crust about 6 times faster as compared to a non-treated infection. In some embodiments of a method of reducing the severity and duration of an infection, the lesions crust about 7 times faster as compared to a non-treated infection. In some embodiments of a method of reducing the severity and duration of an infection, the lesions crust about 8 times faster as compared to a non-treated infection. In some embodiments of a method of reducing the severity and duration of an infection, the lesions crust about 9 times faster as compared to a non-treated infection. In some embodiments of a method of reducing the severity and duration of an infection, the lesions crust about 10 times faster as compared to a non-treated infection. In some embodiments of a method of reducing the severity and duration of an infection, the lesions clear about 2 times faster as compared to a non-treated infection. In some embodiments of a method of reducing the severity and duration of an infection, the lesions clear about 3 times faster as compared to a non-treated infection. In some embodiments of a method of reducing the severity and duration of an infection, the lesions clear about 4 times faster as compared to a non-treated infection. In some embodiments of a method of reducing the severity and duration of an infection, the lesions clear about 5 times faster as compared to a non-treated infection. In some embodiments of a method of reducing the severity and duration of an infection, the lesions clear about 6 times faster as compared to a non-treated infection. In some embodiments of a method of reducing the severity and duration of an infection, the lesions clear about 7 times faster as compared to a non-treated infection. In some embodiments of a method of reducing the severity and duration of an infection, the lesions clear about 8 times faster as compared to a non-treated infection. In some embodiments of a method of reducing the severity and duration of an infection, the lesions clear about 9 times faster as compared to a non-treated infection. In some embodiments of a method of reducing the severity and duration of an infection, the lesions clear about 10 times faster as compared to a non-treated infection.

In some embodiments of a method of reducing the severity and duration of an infection, the infection is a HSV-1 or HSV-2 infection and the administration provides a viral load percent reduction of at least about 90%, for example about 91%, about 92%, about 93%, about 94%, about 95%, about 96%, about 97%, about 98%, about 99%, or about 100% after 5 minutes exposure. In some embodiments of a method of reducing the severity and duration of an infection, the infection is a HSV-2 infection and the administration provides a viral load percent reduction of at least about 96% after 5 minutes exposure. In some embodiments of a method of reducing the severity and duration of an infection, the infection is a HSV-1 infection and the administration provides a viral load percent reduction of at least about 99% after 5 minutes exposure.

In some embodiments of a method of reducing the severity and duration of an infection, the infection is a HSV-1 or HSV-2 infection and the administration provides a viral load percent reduction of at least about 90%, for example about 91%, about 92%, about 93%, about 94%, about 95%, about 96%, about 97%, about 98%, about 99%, or about 100% after 15 minutes exposure. In some embodiments of a method of reducing the severity and duration of an infection, the infection is a HSV-1 or HSV-2 infection and the administration provides a viral load percent reduction of at least about 99% after 15 minutes exposure.

In some embodiments of a method of reducing the severity and duration of an infection, the infection is a HSV-1 or HSV-2 infection and the administration provides a viral load percent reduction of at least about 90%, for example about 91%, about 92%, about 93%, about 94%, about 95%, about 96%, about 97%, about 98%, about 99%, or about 100% after 60 minutes exposure. In some embodiments of a method of reducing the severity and duration of an infection, the infection is a HSV-1 or HSV-2 infection and the administration provides a viral load percent reduction of at least about 99% after 60 minutes exposure.

In some embodiments of a method of reducing the severity and duration of an infection, the infection is a VZV infection and the administration provides a viral load percent reduction of at least about 90%, for example about 91%, about 92%, about 93%, about 94%, about 95%, about 96%, about 97%, about 98%, about 99%, or about 100% after 5 minutes exposure. In some embodiments of a method of reducing the severity and duration of an infection, the infection is a VZV infection and the administration provides a viral load percent reduction of at least about 99% after 5 minutes exposure.

In some embodiments of a method of reducing the severity and duration of an infection, the infection is a VZV infection and the administration provides a viral load percent reduction of at least about 90%, for example about 91%, about 92%, about 93%, about 94%, about 95%, about 96%, about 97%, about 98%, about 99%, or about 100% after 15 minutes exposure. In some embodiments of a method of reducing the severity and duration of an infection, the infection is a VZV infection and the administration provides a viral load percent reduction of at least about 100% after 15 minutes exposure.

In some embodiments of a method of reducing the severity and duration of an infection, the infection is a VZV infection and the administration provides a viral load percent reduction of at least about 90%, for example about 91%, about 92%, about 93%, about 94%, about 95%, about 96%, about 97%, about 98%, about 99%, or about 100% after 60 minutes exposure. In some embodiments of a method of reducing the severity and duration of an infection, the infection is a VZV infection and the administration provides a viral load percent reduction of at least about 100% after 60 minutes exposure.

In some embodiments of a method of reducing the severity and duration of an infection, the subject in need thereof is immuno-compromised. In some embodiments of a method of reducing the severity and duration of an infection, the subject in need thereof is HIV positive. In some embodiments of a method of reducing the severity and duration of an infection, the subject in need thereof has AIDS.

Methods of Preventing the Spread of an Infection

Also disclosed herein are methods of preventing the spread of an infection in a subject in need thereof, the method comprising administering to the subject in need thereof a pharmaceutical composition described herein. In some embodiments of a method of preventing the spread of an infection, the pharmaceutical composition comprises a quaternary ammonium salt. In some embodiments, the quaternary ammonium salt is C10-C16-alkyl(ethylbenzyl)dimethylammonium chloride. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the pharmaceutical composition further comprises ammonium chloride. In some embodiments, the pharmaceutical composition further comprises a chlorite salt. In some embodiments of a method of preventing the spread of an infection, the infection is a viral infection. In some embodiments of a method of preventing the spread of an infection, the viral infection is a sexually transmitted viral infection. In some embodiments of a method of preventing the spread of an infection, the infection is caused by the herpes simplex virus, the human immunodeficiency virus (HIV), the hepatitis B virus, the hepatitis C virus, the human papillomavirus (HPV), or any combination thereof. In some embodiments of a method of preventing the spread of an infection, the infection is caused by the herpes simplex virus. In some embodiments of a method of preventing the spread of an infection, the herpes simplex virus is herpes simplex virus type 1 (HSV-1). In some embodiments of a method of preventing the spread of an infection, the herpes simplex virus is herpes simplex virus type 2 (HSV-2). In some embodiments of a method of preventing the spread of an infection, the infection is caused by the human immunodeficiency virus (HIV). In some embodiments of a method of preventing the spread of an infection, the infection is caused by the hepatitis B virus or the hepatitis C virus. In some embodiments of a method of preventing the spread of an infection, the infection is caused by the human papillomavirus (HPV). In some embodiments of a method of preventing the spread of an infection, the infection is transmitted by contact with infected bodily fluids. In some embodiments of a method of preventing the spread of an infection, the bodily fluid is semen, blood, saliva, sweat, or any combinations thereof. In some embodiments of a method of preventing the spread of an infection, the infected bodily fluid comes in contact with the skin or a mucous membrane. In some embodiments of a method of preventing the spread of an infection, the mucous membrane comprises the lips, the nostrils, the urethra, the vagina, the foreskin, or the anus. In some embodiments of a method of preventing the spread of an infection, the mucous membrane is the vagina.

In some embodiments of a method of preventing the spread of an infection, the infection is caused by the ebolavirus. In some embodiments of a method of preventing the spread of an infection, the infection is caused by the adenovirus.

In some embodiments of a method of preventing the spread of an infection, the infection is a HIV infection and the administration provides a viral load percent reduction of at least about 90%, for example about 91%, about 92%, about 93%, about 94%, about 95%, about 96%, about 97%, about 98%, about 99%, or about 100% after 5 minutes exposure.

In some embodiments of a method of preventing the spread of an infection, the infection is a HIV infection and the administration provides a viral load percent reduction of at least about 90%, for example about 91%, about 92%, about 93%, about 94%, about 95%, about 96%, about 97%, about 98%, about 99%, or about 100% after 15 minutes exposure.

In some embodiments of a method of preventing the spread of an infection, the infection is a HIV infection the administration provides a viral load percent reduction of at least about 90%, for example about 91%, about 92%, about 93%, about 94%, about 95%, about 96%, about 97%, about 98%, about 99%, or about 100% after 60 minutes exposure.

In some embodiments of a method of preventing the spread of an infection, the subject in need thereof is immuno-compromised. In some embodiments of a method of preventing the spread of an infection, the subject in need thereof is HIV positive. In some embodiments of a method of preventing the spread of an infection, the subject in need thereof has AIDS.

Method of Treating an Infection

Also disclosed herein are methods of treating an infection in a subject in need thereof, the method comprising administering to the subject in need thereof a pharmaceutical composition described herein. In some embodiments of a method of treating an infection, the pharmaceutical composition comprises a quaternary ammonium salt. In some embodiments, the quaternary ammonium salt is C10-C16-alkyl(ethylbenzyl)dimethylammonium chloride. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the pharmaceutical composition further comprises ammonium chloride. In some embodiments, the pharmaceutical composition further comprises a chlorite salt.

In some embodiments of a method of treating an infection, the infection is a viral infection. In some embodiments, the infection is caused by the adenovirus. In some embodiments of a method of treating an infection, the adenovirus is selected from Ad 3, Ad 4, Ad 5, Ad 8, Ad 19, and Ad 37. In some embodiments of a method of treating an infection, the adenovirus is selected from Ad 3, Ad 4, Ad 19, and Ad 37. In some embodiments of a method of treating an infection, the adenovirus is selected from Ad 8, Ad 19, and Ad 37. In some embodiments of a method of treating an infection, the adenovirus is selected from Ad 53, Ad 54, and Ad 56. In some embodiments of a method of treating an infection, the human adenovirus is selected from Ad 2, Ad 3, Ad 4, Ad 5, Ad 7, Ad 9, Ad 10, Ad 11, Ad 14, Ad 16, Ad 21, and Ad 29.

In some embodiments of a method of treating an infection, the infection is epidemic keratoconjunctivitis (EKC).

In some embodiments of a method of treating an infection, the infection is caused by Ad 3 and the administration provides a viral load percent reduction of at least about 40%, or about 41%, about 42%, about 43%, about 44%, about 45%, about 46%, about 47%, about 48%, about 49%, or about 50% after 5 minutes exposure. In some embodiments of a method of treating an infection, the infection is caused by Ad 3 and the administration provides a viral load percent reduction of at least about 43% after 5 minutes exposure.

In some embodiments of a method of treating an infection, the infection is caused by Ad 3 and the administration provides a viral load percent reduction of at least about 90%, or about 91%, about 92%, about 93%, about 94%, about 95%, about 96%, about 97%, about 98%, about 99%, or about 100% after 15 minutes exposure. In some embodiments of a method of treating an infection, the infection is caused by Ad 3 and the administration provides a viral load percent reduction of at least about 96% after 15 minutes exposure.

In some embodiments of a method of treating an infection, the infection is caused by Ad 3 and the administration provides a viral load percent reduction of of at least about 90%, or about 91%, about 92%, about 93%, about 94%, about 95%, about 96%, about 97%, about 98%, about 99%, or about 100% after 60 minutes exposure. In some embodiments of a method of treating an infection, the infection is caused by Ad 3 and the administration provides a viral load percent reduction of at least about 99% after 60 minutes exposure.

In some embodiments of a method of treating an infection, the infection is caused by Ad 4 and the administration provides a viral load percent reduction of at least about 60%, or about 61%, about 62%, about 63%, about 64%, about 65%, about 66%, about 67%, about 68%, about 69%, or about 70% after 5 minutes exposure. In some embodiments of a method of treating an infection, the infection is caused by Ad 4 and the administration provides a viral load percent reduction of at least about 68% after 5 minutes exposure.

In some embodiments of a method of treating an infection, the infection is caused by Ad 4 and the administration provides a viral load percent reduction of at least about 80%, or about 81%, about 82%, about 83%, about 84%, about 85%, about 86%, about 87%, about 88%, about 89%, or about 90% after 15 minutes exposure. In some embodiments of a method of treating an infection, the infection is caused by Ad 4 and the administration provides a viral load percent reduction of at least about 82% after 15 minutes exposure.

In some embodiments of a method of treating an infection, the infection is caused by Ad 4 and wherein the administration provides a viral load percent reduction of at least about 90%, or about 91%, about 92%, about 93%, about 94%, about 95%, about 96%, about 97%, about 98%, about 99%, or about 100% after 60 minutes exposure. In some embodiments of a method of treating an infection, the infection is caused by Ad 4 and wherein the administration provides a viral load percent reduction of at least about 94% after 60 minutes exposure.

In some embodiments of a method of treating an infection, the infection is caused by Ad 5 and the administration provides a viral load percent reduction of at least about 60%, or about 61%, about 62%, about 63%, about 64%, about 65%, about 66%, about 67%, about 68%, about 69%, or about 70% after 5 minutes exposure. In some embodiments of a method of treating an infection, the infection is caused by Ad 5 and the administration provides a viral load percent reduction of at least about 68% after 5 minutes exposure.

In some embodiments of a method of treating an infection, the infection is caused by Ad 5 and the administration provides a viral load percent reduction of at least about 90%, or about 91%, about 92%, about 93%, about 94%, about 95%, about 96%, about 97%, about 98%, about 99%, or about 100% after 15 minutes exposure. In some embodiments of a method of treating an infection, the infection is caused by Ad 5 and the administration provides a viral load percent reduction of at least about 94% after 15 minutes exposure.

In some embodiments of a method of treating an infection, the infection is caused by Ad 5 and the administration provides a viral load percent reduction of at least about 90%, or about 91%, about 92%, about 93%, about 94%, about 95%, about 96%, about 97%, about 98%, about 99%, or about 100% after 60 minutes exposure. In some embodiments of a method of treating an infection, the infection is caused by Ad 5 and the administration provides a viral load percent reduction of at least about 99% after 60 minutes exposure.

In some embodiments of a method of treating an infection, the subject in need thereof is immuno-compromised. In some embodiments of a method of treating an infection, the subject in need thereof is HIV positive. In some embodiments of a method of treating an infection, the subject in need thereof has AIDS.

Viral Infections

Enveloped Virus

In some embodiments, the viral infection is caused by an enveloped virus.

An enveloped virus is a virus that has an outer wrapping or envelope. This envelope comes from the infected cell, or host, in a process called "budding off" During the budding process, newly formed virus particles become "enveloped" or wrapped in an outer coat that is made from a small piece of the cell's plasma membrane.

Some viruses (e.g. HIV and many animal viruses) have viral envelopes covering their protective protein capsids. The envelopes are typically derived from portions of the host cell membranes (phospholipids and proteins), but include some viral glycoproteins. They may help viruses avoid the host immune system. Glycoproteins on the surface of the envelope serve to identify and bind to receptor sites on the host's membrane. The viral envelope then fuses with the host's membrane, allowing the capsid and viral genome to enter and infect the host.

The cell from which the virus itself buds will often die or be weakened and shed more viral particles for an extended period. The lipid bilayer envelope of these viruses is relatively sensitive to desiccation, heat, and detergents, therefore these viruses are easier to sterilize than non-enveloped viruses, have limited survival outside host environments, and typically must transfer directly from host to host. Enveloped viruses possess great adaptability and can change in a short time in order to evade the immune system. Enveloped viruses can cause persistent infections.

Herpes Labialis

In some embodiments, the viral infection is caused by the herpes virus. In some embodiments, the herpes virus causes herpes labialis.

Herpes labialis, also known as cold sores, is a type of herpes simplex infection affecting the lips. An outbreak of herpes labialis is caused by infection of the lips by the herpes simplex virus (HSV) and typically causes small blisters or sores on or around the mouth. The sores typically heal within 2-3 weeks, but the herpes simplex virus remains dormant in the facial nerve branches. After infection of the facial nerve, the virus periodically reactivates to create sores in the same area of the mouth or face at the site of the original infection.

Cold sore recurrences range from rare episodes to 12 or more episodes per year. People with the condition typically experience one to three attacks each year. The frequency and severity of outbreaks generally decrease over time.

Herpes infections usually show no symptoms; when symptoms do appear they typically resolve within two weeks. The main symptom of oral infection is inflammation of the mucosa of the cheek and gums—known as acute herpetic gingivostomatitis—which occurs within 5-10 days of infection. Other symptoms may also develop, including headache, nausea, dizziness and painful ulcers—sometimes confused with canker sores—fever, and sore throat.

Primary HSV infection in adolescents frequently manifests as severe pharyngitis with lesions developing on the cheek and gums. Some individuals develop difficulty in swallowing (dysphagia) and swollen lymph nodes (lymphadenopathy). Primary HSV infections in adults often results in pharyngitis similar to that observed in glandular fever (infectious mononucleosis), but gingivostomatitis is less likely.

Recurrent oral infection is more common with HSV-1 infections than with HSV-2. Symptoms typically progress in a series of eight stages:

1. Latent (weeks to months incident-free): The remission period; After initial infection, the viruses move to sensory nerve ganglia (trigeminal ganglion), where they reside as lifelong, latent viruses. Asymptomatic shedding of contagious virus particles can occur during this stage.

2. Prodromal (day 0-1): Symptoms often precede a recurrence. Symptoms typically begin with tingling (itching) and reddening of the skin around the infected site. This stage can last from a few days to a few hours preceding the physical manifestation of an infection and is the best time to start treatment.

3. Inflammation (day 1): Virus begins reproducing and infecting cells at the end of the nerve. The healthy cells react to the invasion with swelling and redness displayed as symptoms of infection.

4. Pre-sore (day 2-3): This stage is defined by the appearance of tiny, hard, inflamed papules and vesicles that may itch and are painfully sensitive to touch. In time, these fluid-filled blisters form a cluster on the lip (labial) tissue, the area between the lip and skin (vermilion border), and can occur on the nose, chin, and cheeks.

5. Open lesion (day 4): This is the most painful and contagious of the stages. All the tiny vesicles break open and merge to create one big, open, weeping ulcer. Fluids are slowly discharged from blood vessels and inflamed tissue. This watery discharge is teeming with active viral particles and is highly contagious. Depending on the severity, one may develop a fever and swollen lymph glands under the jaw.

6. Crusting (day 5-8): A honey/golden crust starts to form from the syrupy exudate. This yellowish or brown crust or scab is not made of active virus but from blood serum containing useful proteins such as immunoglobulins. This appears as the healing process begins. The sore is still painful at this stage, but, more painful, however, is the constant cracking of the scab as one moves or stretches their lips, as in smiling or eating. Virus-filled fluid will still ooze out of the sore through any cracks.

7. Healing (day 9-14): New skin begins to form underneath the scab as the virus retreats into latency. A series of scabs will form over the sore (called Meier Complex), each one smaller than the last. During this phase irritation, itching, and some pain are common.

8. Post-scab (12-14 days): A reddish area may linger at the site of viral infection as the destroyed cells are regenerated. Virus shedding can still occur during this stage.

Rare reinfections occur inside the mouth (intraoral HSV stomatitis) affecting the gums, alveolar ridge, hard palate, and the back of the tongue, possibly accompanied by herpes labialis.

Genital Herpes

In some embodiments, the viral infection is caused by the herpes virus. In some embodiments, the herpes virus causes genital herpes.

Genital herpes is a genital infection caused by the herpes simplex virus (HSV). Most individuals carrying herpes are unaware they have been infected and many will never suffer an outbreak, which involves blisters similar to cold sores. While there is no cure for herpes, over time symptoms are increasingly mild and outbreaks are decreasingly frequent. When symptomatic, the typical manifestation of a primary infection is clusters of genital sores consisting of inflamed papules and vesicles on the outer surface of the genitals, resembling cold sores. These usually appear 4-7 days after sexual exposure to HSV for the first time. Genital HSV-1 infection recurs at rate of about one sixth of that of genital HSV-2. Although genital herpes was previously caused primarily by HSV-2, genital HSV-1 infections are increasing and now cause up to 80% of infections. In 2013 about 1.1 billion people (15.9%) had asymptomatic genital herpes and 47 million new cases of genital herpes occurred. A 1998 study indicated it was the most common sexually transmitted infection by the number of cases.

Shingles

In some embodiments, the viral infection is caused by the varicella zoster virus (VZV).

Shingles, also known as herpes zoster, is a viral disease characterized by a painful skin rash with blisters in a localized area. Typically the rash occurs in a single stripe either on the left or right of the body or face. Two to four days before the rash occurs there may be tingling or local pain in the area. Otherwise there are typically few symptoms. The rash usually heals within two to four weeks; however, some people develop ongoing nerve pain which can last for months or years, a condition called postherpetic neuralgia. In some embodiments, in those with poor immune function the rash occurs widely. In some embodiments, vision loss occurs when the rash involves the eye.

Shingles is due to a reactivation of varicella zoster virus (VZV) within a person's body. Chickenpox is due to an initial infection with VZV. Once chickenpox has resolved, the virus may remain inactive in nerve cells. When it reactivates it travels from the nerve body to the endings in the skin producing blisters. Risk factors for reactivation include old age, poor immune function, and having had chickenpox before 18 months of age. How the virus remains in the body or subsequently re-activates is not well understood. Exposure to the virus in the blisters can cause chickenpox in someone who has not had it before but will not trigger shingles. Diagnosis is typically based on a person's signs and symptoms. Varicella zoster virus is not the same as herpes simplex virus; however, they belong to the same family of viruses.

The shingles vaccine decreases the chance of shingles by about half in those between the ages of 50 and 80. It also decreases rates of postherpetic neuralgia, and if an outbreak occurs, its severity. After 80 the vaccine is still effective, just less so. It contains the same material as the varicella vaccine, just at a higher dose. If shingles develops, antiviral medications such as aciclovir can reduce the severity and duration of disease if started within 72 hours of the appearance of the rash. Evidence does not show a significant effect of antivirals or steroids on rates of postherpetic neuralgia. In some embodiments, acetaminophen, NSAIDs, or opioids are used to help with the acute pain.

It is estimated that about a third of people develop shingles at some point in their life. While more common among older people, children may also get the disease. The number of new cases per year ranges from 1.2-3.4 per 1,000 among healthy individuals to 3.9-11.8 per 1,000 among those older than 65 years of age. About half of those living to age 85 will have at least one attack, and less than 5% will have more than one attack.

The earliest symptoms of shingles, which include headache, fever, and malaise, are nonspecific, and may result in an incorrect diagnosis. These symptoms are commonly followed by sensations of burning pain, itching, hyperesthesia (oversensitivity), or paresthesia ("pins and needles": tingling, pricking, or numbness). Pain can be mild to extreme in the affected dermatome, with sensations that are often described as stinging, tingling, aching, numbing or throbbing, and can be interspersed with quick stabs of agonizing pain.

Shingles in children is often painless, but people are more likely to get shingles as they age, and the disease tends to be more severe.

In most cases after one to two days, but sometimes as long as three weeks, the initial phase is followed by the appearance of the characteristic skin rash. The pain and rash most commonly occurs on the torso, but can appear on the face, eyes or other parts of the body. At first the rash appears similar to the first appearance of hives; however, unlike hives, shingles causes skin changes limited to a dermatome, normally resulting in a stripe or belt-like pattern that is limited to one side of the body and does not cross the midline. Zoster sine herpete ("zoster without herpes") describes a person who has all of the symptoms of shingles except this characteristic rash.

Later the rash becomes vesicular, forming small blisters filled with a serous exudate, as the fever and general malaise continue. The painful vesicles eventually become cloudy or darkened as they fill with blood, and crust over within seven to ten days; usually the crusts fall off and the skin heals, but sometimes, after severe blistering, scarring and discolored skin remain.

Shingles may have additional symptoms, depending on the dermatome involved. The trigeminal nerve is the most commonly involved nerve. The ophthalmic division of the trigeminal nerve is the most commonly involved branch. When the virus is reactivated in this nerve branch it is termed zoster ophthalmicus. The skin of the forehead, upper eyelid and orbit of the eye may be involved. Zoster ophthalmicus occurs in approximately 10% to 25% of cases. In some people, symptoms include conjunctivitis, keratitis, uveitis, and optic nerve palsies that can sometimes cause chronic ocular inflammation, loss of vision, and debilitating pain.

Shingles oticus, also known as Ramsay Hunt syndrome type II, involves the ear. It is thought to result from the virus spreading from the facial nerve to the vestibulocochlear nerve. Symptoms include hearing loss and vertigo (rotational dizziness).

In some embodiments, shingles occur in the mouth if the maxillary or mandibular division of the trigeminal nerve is affected, in which the rash appears on the mucous membrane of the upper jaw (usually the palate, sometimes the gums of the upper teeth) or the lower jaw (tongue or gums of the lower teeth) respectively. Oral involvement may occur alone or in combination with a rash on the skin over the cutaneous distribution of the same trigeminal branch. As with shingles of the skin, the lesions tend to only involve one side, distinguishing it from other oral blistering conditions. In the mouth, shingles appears initially as 1-4 mm opaque blisters (vesicles), which break down quickly to leave ulcers that heal within 10-14 days. The prodromal pain (before the rash) may be confused with toothache. Sometimes this leads to unnecessary dental treatment. Post herpetic neuralgia uncommonly is associated with shingles in the mouth. Unusual complications may occur with intra-oral shingles that are not seen elsewhere. Due to the close relationship of blood vessels to nerves, the virus can spread to involve the blood vessels and compromise the blood supply, sometimes causing ischemic necrosis. Therefore, oral involvement rarely causes complications such as osteonecrosis, tooth loss, periodontitis (gum disease), pulp calcification, pulp necrosis, periapical lesions and tooth developmental anomalies.

Disseminated Shingles

In those with poor immune function, disseminated shingles may occur (wide rash). It is defined as more than twenty skin lesions appearing outside either the primarily affected dermatome or dermatomes directly adjacent to it. Besides the skin, other organs, such as the liver or brain, may also be affected (causing hepatitis or encephalitis respectively), making the condition potentially lethal.

Pathophysiology

Progression of shingles. A cluster of small bumps (1) turns into blisters (2). The blisters fill with lymph, break open (3), crust over (4), and finally disappear. Postherpetic neuralgia can sometimes occur due to nerve damage (5).

The causative agent for shingles is the varicella zoster virus (VZV)—a double-stranded DNA virus related to the Herpes simplex virus. Most individuals are infected with this virus as children which causes an episode of chickenpox. The immune system eventually eliminates the virus from most locations, but it remains dormant (or latent) in the ganglia adjacent to the spinal cord (called the dorsal root ganglion) or the trigeminal ganglion in the base of the skull.

Shingles occurs only in people who have been previously infected with VZV; although it can occur at any age, approximately half of the cases in the United States occur in those aged 50 years or older. Repeated attacks of shingles are rare, and it is extremely rare for a person to have more than three recurrences.

The disease results from virus particles in a single sensory ganglion switching from their latent lysogenic cycles to their active lytic cycles. In contrast to the herpes simplex virus, the latency of VZV is poorly understood. The virus has never been successfully recovered from human nerve cells by cell culture. The complete sequence of the viral genome was published in 1986. Virus-specific proteins continue to be made by the infected cells during the latent period, so true latency, as opposed to chronic, low-level, active infection, has not been proven to occur in VZV infections. Although VZV has been detected in autopsies of nervous tissue, there are no methods to find dormant virus in the ganglia of living people.

Unless the immune system is compromised, it suppresses reactivation of the virus and prevents shingles outbreaks. Why this suppression sometimes fails is poorly understood, but shingles is more likely to occur in people whose immune systems are impaired due to aging, immunosuppressive therapy, psychological stress, or other factors. Upon reactivation, the virus replicates in neuronal cell bodies, and virions are shed from the cells and carried down the axons to the area of skin innervated by that ganglion. In the skin, the virus causes local inflammation and blistering. The short- and long-term pain caused by shingles outbreaks originates from inflammation of affected nerves due to the widespread growth of the virus in those areas.

As with chickenpox and/or other forms of herpes, direct contact with an active rash can spread VZV to a person who has no immunity to the virus. This newly infected individual may then develop chickenpox, but will not immediately develop shingles.

Herpetic Simplex Keratitis

Herpetic simplex keratitis, also known as herpetic keratoconjunctivitis and herpesviral keratitis, is a form of keratitis caused by recurrent herpes simplex virus (HSV) infection in the cornea. Herpetic simplex keratitis begins with infection of epithelial cells on the surface of the eye and retrograde infection of nerves serving the cornea. Primary infection typically presents as swelling of the conjunctiva and eyelids (blepharoconjunctivitis), accompanied by small white itchy lesions on the corneal surface. The effect of the lesions varies, from minor damage to the epithelium (superficial punctate keratitis), to more serious consequences such as the formation of dendritic ulcers. Infection is unilateral, affecting one eye at a time. Additional symptoms include dull pain deep inside the eye, mild to acute dryness, and sinusitis. Subsequent recurrences may be more severe, with infected epithelial cells showing larger dendritic ulceration, and lesions forming white plaques. The epithelial layer is sloughed off as the dendritic ulcer grows, and mild inflammation (iritis) may occur in the underlying stroma of iris. Sensation loss occurs in lesional areas, producing generalized corneal anaesthesia with repeated recurrences. Recurrence can be accompanied by chronic dry eye, low grade intermittent conjunctivitis, or chronic unexplained sinusitis. Following persistent infection the concentration of viral DNA reaches a critical limit. Antibody responses against the viral antigen expression in the stroma can trigger a massive immune response in the eye. The response may result in the destruction of the corneal stroma, resulting in loss of vision due to opacification of the cornea. This is known as immune-mediated stromal keratitis.

Ebolavirus

In some embodiments, the viral infection is caused by the ebola virus.

Ebola virus disease (EVD), also known as Ebola hemorrhagic fever (EHF) or simply Ebola, is a viral hemorrhagic fever of humans and other primates caused by ebolaviruses. Signs and symptoms typically start between two days and three weeks after contracting the virus with a fever, sore throat, muscular pain, and headaches. Vomiting, diarrhea and rash usually follow, along with decreased function of the liver and kidneys. At this time, some people begin to bleed both internally and externally. The disease has a high risk of death, killing between 25 and 90 percent of those infected, with an average of about 50 percent. This is often due to low blood pressure from fluid loss, and typically follows six to sixteen days after symptoms appear.

The virus spreads through direct contact with body fluids, such as blood from infected humans or other animals. Spread may also occur from contact with items recently contaminated with bodily fluids. Spread of the disease through the air between primates, including humans, has not been documented in either laboratory or natural conditions. Semen or breast milk of a person after recovery from EVD may carry the virus for several weeks to months. Fruit bats are believed to be the normal carrier in nature, able to spread the virus without being affected by it. Other diseases such as malaria, cholera, typhoid fever, meningitis and other viral hemorrhagic fevers may resemble EVD. Blood samples are tested for viral RNA, viral antibodies or for the virus itself to confirm the diagnosis.

Epidemic Keratoconjunctivitis (EKC).

Epidemic keratoconjunctivitis (EKC) is characterized by typical symptoms of conjunctivitis such as acute onset of watering redness, foreign body sensation and severe pain. Symptoms further include inflammation in the conjunctiva (conjunctivitis) and in the cornea (keratitis), associated pain, edema, diminished eyesight, tearing, sensitivity to light, feeling or sensation as if a foreign body were present in the eye, and the development of pseudo membranes. During the acute phase, which persists for approximately two to three weeks, viruses are present and are replicating. In the typical case, first one eye gets infected after which the infection spreads to the other eye within two to three days. Both eyes are affected in 60% of cases. The infection in the first eye is typically more serious. In approximately 20-50% of patients, corneal opacities are developed that result in deteriorating vision that remains for weeks and months, and in rare cases even years. Since the disease is often epidemic in nature, it is called epidemic keratoconjunctivitis (EKC).

Epidemic keratoconjunctivitis is caused by adenoviruses. The family Adenoviridae comprises more than 130 different serotypes and includes viruses that can infect human beings, other mammals, birds, reptiles, and amphibians. This broad spectrum of hosts seems to imply that the adenoviruses are descended from a common precursor virus that existed 350 to 400 million years ago. The 54 types of adenovirus now known to be pathogenic in man are classified in seven groups, which are labeled A through G.

Adenoviruses are double-stranded DNA viruses roughly 80 to 110 nm in size. They are surrounded by an icosahedral capsid bearing group- and type-specific antigens; they have no outer lipid bilayer. They are highly resistant to environmental influences and can survive contact with many of the usual commercially available types of disinfectant. They remain infectious for weeks when kept at room temperature and thus have a high aptitude for causing nosocomial infections.

Adenoviruses are found all over the world and are transmitted through droplets and smears of infected bodily fluids that enter the human body through the nose, throat, and conjunctiva. The viral incubation time is 2 to 12 days. The disease is probably contagious even before symptoms arise, and it certainly remains so as long as the virus can still be demonstrated in bodily fluids; this period (for tear fluid) usually lasts two to three weeks from the date of transmission of the virus.

The disease can be transmitted on the hands as well as on objects such as tissues and handkerchiefs, doorknobs, etc. Nosocomial EKC contracted in eye clinics and doctors' offices is usually due to contaminated instruments (e.g., tonometers) and eyedrops.

Adenoviruses cause a wide variety of diseases—not just ocular infections, but also respiratory and gastrointestinal ones. Individual serotypes typically cause specific types of disease; thus, EKC is usually due to serotypes 8, 19, and 37, follicular conjunctivitis to serotypes 3, 4 and 7, and pharyngeal-conjunctival fever to serotypes 3, 7, and (rarely) 14. Respiratory infections such as pneumonia, tonsillitis, and pharyngitis are caused by serotypes 1-5, 7, 14, and 21, while serotypes 1, 2, 5, 31, 40 and 41 cause gastroenteritis. Serotypes 1, 2, and 5 can produce sepsis-like manifestations, particularly in severely immunocompromised patients.

Adenoviruses

In some embodiments, the viral infection is caused by an adenovirus.

Adenoviruses (members of the family Adenoviridae) are medium-sized (90-100 nm), nonenveloped (without an outer lipid bilayer) viruses with an icosahedral nucleocapsid containing a double stranded DNA genome. Their name derives from their initial isolation from human adenoids in 1953.

They have a broad range of vertebrate hosts; in humans, more than 50 distinct adenoviral serotypes have been found to cause a wide range of illnesses, from mild respiratory infections in young children (known as the common cold) to life-threatening multi-organ disease in people with a weakened immune system.

Adenoviruses represent the largest known nonenveloped viruses. They are able to be transported through the endosome (i.e., envelope fusion is not necessary). The virion also has a unique "spike" or fiber associated with each penton base of the capsid that aids in attachment to the host cell via the receptor on the surface of the host cell.

Different types/serotypes are associated with different conditions: respiratory disease (mainly species HAdV-B and C); conjunctivitis (HAdV-B and D); gastroenteritis (HAdV—F types 40, 41, HAdV-G type 52); obesity or adipogenesis (HAdV-A type 31, HAdV—C type 5, HAdV-D types 9, 36, 37).

Influenza virus.

In some embodiments, the viral infection is caused by the influenza virus.

Influenza, commonly known as the flu, is an infectious disease caused by an influenza virus. Symptoms can be mild to severe. The most common symptoms include: high fever, runny nose, sore throat, muscle pains, headache, coughing, sneezing, and feeling tired. These symptoms typically begin two days after exposure to the virus and most last less than a week. The cough, however, may last for more than two weeks. In children, there may be diarrhea and vomiting, but these are not common in adults. Diarrhea and vomiting occur more commonly in gastroenteritis, which is an unrelated disease and sometimes inaccurately referred to as "stomach flu" or the "24-hour flu". Complications of influenza may include viral pneumonia, secondary bacterial pneumonia, sinus infections, and worsening of previous health problems such as asthma or heart failure.

Three of the four types of influenza viruses affect humans: Type A, Type B, and Type C. Type D has not been known to infect humans, but is believed to have the potential to do so. Usually, the virus is spread through the air from coughs or sneezes. This is believed to occur mostly over relatively short distances. It can also be spread by touching surfaces contaminated by the virus and then touching the mouth or eyes. A person may be infectious to others both before and during the time they are showing symptoms. The infection may be confirmed by testing the throat, sputum, or nose for the virus. A number of rapid tests are available; however, people may still have the infection even if the results are negative. A type of polymerase chain reaction that detects the virus's RNA is more accurate.

Frequent hand washing reduces the risk of viral spread. Wearing a surgical mask is also useful. Yearly vaccinations against influenza are recommended by the World Health Organization for those at high risk. The vaccine is usually effective against three or four types of influenza. It is usually well-tolerated. A vaccine made for one year may not be useful in the following year, since the virus evolves rapidly. Antiviral drugs such as the neuraminidase inhibitor oseltamivir, among others, have been used to treat influenza. The benefit of antiviral drugs in those who are otherwise healthy do not appear to be greater than their risks. No benefit has been found in those with other health problems.

Influenza spreads around the world in yearly outbreaks, resulting in about three to five million cases of severe illness and about 250,000 to 500,000 deaths. About 20% of unvaccinated children and 10% of unvaccinated adults are infected each year. In the northern and southern parts of the world, outbreaks occur mainly in the winter, while around the Equator, outbreaks may occur at any time of the year. Death occurs mostly in the young, the old, and those with other health problems. Larger outbreaks known as pandemics are less frequent. In the 20th century, three influenza pandemics occurred: Spanish influenza in 1918 (~50 million deaths), Asian influenza in 1957 (two million deaths), and Hong Kong influenza in 1968 (one million deaths). The World Health Organization declared an outbreak of a new type of influenza A/H1N1 to be a pandemic in June 2009. Influenza may also affect other animals, including pigs, horses, and birds.

Chickenpox

In some embodiments, the viral infection is caused by the varicella zoster virus which develops into varicella (chickenpox)

Chickenpox, also known as varicella, is a highly contagious disease caused by the initial infection with varicella zoster virus (VZV). The disease results in a characteristic skin rash that forms small, itchy blisters, which eventually scab over. It usually starts on the chest, back, and face then spreads to the rest of the body. Other symptoms may include fever, tiredness, and headaches. Symptoms usually last five to seven days. Complications may occasionally include pneumonia, inflammation of the brain, and bacterial skin infections. The disease is often more severe in adults than in children. Symptoms begin 10 to 21 days after exposure to the virus.

Chickenpox is an airborne disease which spreads easily through the coughs and sneezes of an infected person. It may be spread from one to two days before the rash appears until all lesions have crusted over. It may also spread through contact with the blisters. Those with shingles may spread chickenpox to those who are not immune through contact with the blisters. The disease can usually be diagnosed based on the presenting symptom; however, in unusual cases it may be confirmed by polymerase chain reaction (PCR) testing of the blister fluid or scabs. Testing for antibodies may be done to determine if a person is or is not immune. People usually only get chickenpox once. Although reinfections by the virus occur, these reinfections usually do not cause any symptoms.

The initial symptoms of the disease included fever and vomiting. This was followed by formation of sores in the mouth and a skin rash. Over a number of days the skin rash turned into characteristic fluid filled bumps with a dent in the center. The bumps then scabbed over and fell off leaving scars. The disease used to spread between people or via contaminated objects.

Human Immunodeficiency Viruses (HIV)

In some embodiments, the viral infection is caused by the human immunodeficiency viruses (HIV).

The human immunodeficiency viruses (HIV) are two species of Lentivirus (a subgroup of retrovirus) that causes HIV infection and over time acquired immunodeficiency syndrome (AIDS). AIDS is a condition in humans in which progressive failure of the immune system allows life-threatening opportunistic infections and cancers to thrive. Without treatment, average survival time after infection with HIV is estimated to be 9 to 11 years, depending on the HIV subtype. In most cases, HIV is a sexually transmitted infection and occurs by contact with or transfer of blood, pre-ejaculate, semen, and vaginal fluids. Non-sexual transmission can occur from an infected mother to her infant during pregnancy, during childbirth by exposure to her blood or vaginal fluid, and through breast milk. Within these bodily fluids, HIV is present as both free virus particles and virus within infected immune cells.

HIV infects vital cells in the human immune system, such as helper T cells (specifically CD4+ T cells), macrophages, and dendritic cells. HIV infection leads to low levels of CD4+ T cells through a number of mechanisms, including pyroptosis of abortively infected T cells, apoptosis of uninfected bystander cells, direct viral killing of infected cells, and killing of infected CD4+ T cells by CD8+ cytotoxic lymphocytes that recognize infected cells. When CD4+ T cell numbers decline below a critical level, cell-mediated immunity is lost, and the body becomes progressively more susceptible to opportunistic infections, leading to the development of AIDS.

Mode of Administration

In some embodiments, the pharmaceutical composition described herein is applied topically to the skin or a mucous membrane. In some embodiments, the mucous membrane comprises the lips, the nostrils, the urethra, the vagina, the foreskin, or the anus. In some embodiments, the pharmaceutical composition described herein is applied directly to the lesions associated with the infection. In some embodiment, the lesions are located on the lips. In some embodiment, the lesions are located in the nostrils.

In some embodiments, the pharmaceutical composition described herein is applied to the eye as an ophthalmic composition suitable for topical administration. In some embodiments, the pharmaceutical composition described herein is applied as an aerosol to treat an upper respiratory infection.

In some embodiments, the pharmaceutical composition described herein is applied to a body region that might be exposed to a virus. In some embodiments, the pharmaceutical composition described herein is applied to a body region that might be exposed to a virus during sexual intercourse.

In some embodiments, the pharmaceutical composition described herein is applied topically once per day, twice per day, three times per day, four times per day, five times per day or more frequent, every day, once per week, twice per week, three times per week, four times per week, five times per week, six times per week, every other day, every other week, once per month, twice per month, three times per month, continuously over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or more. In some embodiments, the pharmaceutical composition is applied for at least 10 days. In some embodiments, the pharmaceutical composition is applied for at least 9 days. In some embodiments, the pharmaceutical composition is applied for at least 8 days. In some embodiments, the pharmaceutical composition is applied for at least 7 days. In some embodiments, the pharmaceutical composition is applied for at least 6 days. In some embodiments, the pharmaceutical composition is applied for at least 5 days. In some embodiments, the pharmaceutical composition is applied for at least 4 days. In some embodiments, the pharmaceutical composition is applied for at least 3 days.

In some embodiments, the pharmaceutical composition described herein is applied topically prior to intercourse. In some embodiments, the pharmaceutical composition described herein is applied topically to a body region that might be exposed to a virus. In some embodiments, the pharmaceutical composition described herein is applied topically to a body region that might be exposed to a virus during intercourse. In some embodiments, the pharmaceutical composition described herein is applied topically to a body region that might be exposed to HIV. In some embodiments, the pharmaceutical composition described herein is applied topically to a body region that might be exposed to HIV during intercourse.

In some embodiments, the pharmaceutical composition is applied for about 10 days. In some embodiments, the pharmaceutical composition is applied for about 9 days. In some embodiments, the pharmaceutical composition is applied for about 8 days. In some embodiments, the pharmaceutical composition is applied for about 7 days. In some embodiments, the pharmaceutical composition is applied for about 6 days. In some embodiments, the pharmaceutical composition is applied for about 5 days. In some embodiments, the pharmaceutical composition is applied for about 4 days. In some embodiments, the pharmaceutical composition is applied for about 3 days.

In some embodiments, the pharmaceutical composition is applied until the lesions clear the skin. In some embodiments, the pharmaceutical composition is applied until the lesions crust. In some embodiments, the pharmaceutical composition is applied until the infection is no longer contagious.

Combinations

Also described herein are methods of reducing the severity and duration of an infection in a subject in need thereof, comprising administering an additional therapeutic agent. In some embodiments, the additional therapeutic agent is antiviral agent. In some embodiments, the antiviral agent is selected from acyclovir, famciclovir, valacyclovir, penciclovir, ganciclovir, valganciclovir, and any combinations thereof. In some embodiments, the additional therapeutic agent is docosanol. In some embodiments, the additional therapeutic agent is benzocaine. In some embodiments, the additional therapeutic agent a steroid. In some embodiments, the additional therapeutic agent is an anti-inflammatory agent.

Also described herein are methods of preventing the spread of an infection in a subject in need thereof, comprising administering an additional therapeutic agent. In some embodiments, the infection is a sexually transmitted infection. In some embodiments, the infection is caused by the herpes virus, the human immunodeficiency virus (HIV), the hepatitis B virus, the hepatitis C virus, or the human papillomavirus (HPV). In some embodiments, the infection is caused by the ebolavirus. In some embodiments, the additional therapeutic agent is an antiretroviral agent. In some embodiments, the antiretroviral agent is selected from a nucleoside/nucleotide reverse transcriptase inhibitor, also called nucleoside analogs, such as abacavir, emtricitabine, and tenofovir; nonnucleoside reverse transcriptase inhibitors (NNRTIs), such as efavirenz, etravirine, and nevirapine; protease inhibitors (PIs), such as atazanavir, darunavir, and ritonavir; entry inhibitors, such as enfuvirtide and maraviroc; and integrase inhibitors, such as dolutegravir and raltegravir; and any combinations thereof. In some embodiments, the additional therapeutic agent is antiviral agent. In some embodiments, the antiviral agent is selected from acyclovir, famciclovir, valacyclovir, penciclovir, ganciclovir, valganciclovir, and any combinations thereof. In some embodiments, the additional therapeutic agent is docosanol. In some embodiments, the additional therapeutic agent a steroid. In some embodiments, the additional therapeutic agent is an anti-inflammatory agent.

Also described herein are methods of treating an infection in a subject in need thereof, comprising administering an additional therapeutic agent. In some embodiments, the infection is epidemic keratoconjunctivitis (EKC). In some embodiments, the additional therapeutic agent is dexamethasone/povidone-iodine. In some embodiments, the additional therapeutic agent a steroid. In some embodiments, the additional therapeutic agent is an anti-inflammatory agent.

In some embodiments, the pharmaceutical composition described herein is administered at the same time as the additional therapeutic agent. In some embodiments, the pharmaceutical composition described herein is administered after the administration of the additional therapeutic agent. In some embodiments, the pharmaceutical composition described herein is administered before the administration of the additional therapeutic agent. In some embodiments, the pharmaceutical composition described herein is administered every time the additional therapeutic agent is administered. In some embodiments, the pharmaceutical composition described herein is administered in between administrations of the additional therapeutic agent.

In some embodiments, the additional therapeutic agent is administered once a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered twice a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered three times a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered four times a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered five times a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered six times a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered seven times a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered eight times a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered nine times a day and the pharmaceutical composition described herein is administered once a day, twice a day, three times a day, four times a day, five times a day, six times a day, seven times a day, eight times a day, nine times a day, or ten times a day. In some embodiments, the additional therapeutic agent is administered ten times a day and the pharmaceutical composition described herein is administered once a day, twice a day, three times a day, four times a day, five times a day, six times a day, seven times a day, eight times a day, nine times a day, or ten times a day.

In some embodiments, the pharmaceutical composition described herein is administered as a topical formulation and the additional therapeutic agent is administered as an oral formulation. In some embodiments, the pharmaceutical composition described herein is administered as a topical formulation and the additional therapeutic agent is administered as a topical formulation.

In some embodiments, the pharmaceutical composition described herein and the additional therapeutic agent are co-formulated.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include topical pharmaceutical composition described herein comprising a quaternary ammonium salt. In some embodiments, the quaternary ammonium salt is C10-C16-alkyl(ethylbenzyl)dimethylammonium chloride. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the pharmaceutical composition further comprises ammonium chloride. In some embodiments, the pharmaceutical composition further comprises a chlorite salt. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Guinea Pig Maximisation Test

The Guinea pig maximisation test (GPMT) is an in vivo test to screen for substances that cause human skin sensitisation (i.e. allergens). It was first proposed by B. Magnusson and Albert Kligman in 1969 and described in their 1970 book Allergic Contact Dermatitis in the Guinea Pig.

The test animals are exposed intradermally to the test material, along with an adjuvant to enhance the immune reaction of the guinea pig. The guinea pigs are then a short while later exposed to a lower concentration of the test material, and their allergic reaction, if any, measured. 15% of guinea pigs must show a reaction for the test to be considered positive. 20 animals would typically be used to ensure against false negative results.

The test animals are initially exposed to the test substance by intradermal injection and/or epidermal application (induction exposure). Following a rest period of 10 to 14 days (induction period), during which an immune response may develop, the animals are exposed to a challenge dose. The extent and degree of skin reaction to the challenge exposure in the test animals is compared with that demonstrated by control.

Regulatory: The OECD Guidelines for the Testing of Chemicals guideline No. 406 of 1992.

The skin is evaluated following the Magnusson and Kligman grading scale for the evaluation of challenge patch test reactions:

| Observation | Score |
| --- | --- |
| No visible change | 0 |
| Discrete or patchy erythema | 1 |
| Moderate and confluent erythema | 2 |
| Intense erythema and swelling | 3 |

In some embodiments, the topical pharmaceutical composition described herein is not a skin sensitizer. In some embodiments, the topical pharmaceutical composition described herein grading score is less than about 2. In some embodiments, the topical pharmaceutical composition described herein grading score is less than about 1. In some embodiments, the topical pharmaceutical composition described herein grading score is about 0.

Local Lymph Node Assay

The murine local lymph node assay (LLNA) is an in vivo test for skin sensitization. The principle underlying the LLNA is that skin sensitizers induce growth of lymphocytes in the lymph nodes draining the site of application. Lymphocyte proliferation can be measured by radiolabeling (quantifying tritiaded thymidine), bioluminescence (quantifying ATP content in lymphocytes) or immunoassay (ELISA utilizing an antibody specific for BrdU).

The test material is applied to the ears of mice. Optionally, a tracer substance such as 3H-Methyl-thymidine or BrdU is injected intraperitoneally for lymphocyte incorporation. The animals are euthanized and their lymph node cells are removed and analyzed. The ratio of tracer incorporation in lymph nodes from dosed animals is compared to control animals, giving a stimulation index (SI). When the stimulation index exceeds 3 (SI>3), a relevant sensitizing potential is assumed. In contrast to the classical guinea pig tests, the LLNA provides a quantitative measurement of sensitizing potency of a tested chemical.

Regulatory: The OECD Guidelines for the Testing of Chemicals guideline No. 429 of 23 Jul. 2010.

The basic principle underlying the LLNA is that sensitizers induce proliferation of lymphocytes in the lymph nodes draining the site of test substance application. This proliferation is proportional to the dose and to the potency of the applied allergen and provides a simple means of obtaining a quantitative measurement of sensitization. Proliferation is measured by comparing the mean proliferation in each test group to the mean proliferation in the vehicle treated control (VC) group. The ratio of the mean proliferation in each treated group to that in the concurrent VC group, termed the Stimulation Index (SI), is determined, and should be >3 before classification of the test substance as a potential skin sensitizer is warranted. The methods described here are based on the use of in vivo radioactive labelling to measure an increased number of proliferating cells in the draining auricular lymph nodes. However, other endpoints for assessment of the number of proliferating cells may be employed provided the PS requirements are fully met.

The erythema are score as follow:

| Observation | Score |
| --- | --- |
| No erythema | 0 |
| Very slight erythema (barely perceptible) | 1 |
| Well-defined erythema | 2 |
| Moderate to severe erythema | 3 |
| Severe erythema (beet redness) to eschar formation preventing grading of erythema | 4 |

The Stimulation Index (SI) is the value calculated to assess the skin sensitization potential of a test substance. SI is the ratio of the proliferation in treated groups to that in the concurrent vehicle control group.

In some embodiments, the topical pharmaceutical composition described herein has an SI of less than about 3 as measured by the LLNA assay. In some embodiments, the topical pharmaceutical composition described herein has an SI of less than about 2 as measured by the LLNA assay. In some embodiments, the topical pharmaceutical composition described herein has an SI of less than about 1 as measured by the LLNA assay. In some embodiments, the topical pharmaceutical composition described herein has an SI of about 0 as measured by the LLNA assay.

EMBODIMENTS

Embodiment 1

A method of reducing the severity or the duration of the symptoms of an infection in a subject in need thereof, the method comprising administering to the subject in need thereof a pharmaceutical composition comprising C10-C16-alkyl(ethylbenzyl)dimethylammonium chloride.

Embodiment 2

The method of embodiment 1, wherein the infection is a viral infection.

Embodiment 3

The method of embodiment 1 or 2, wherein the infection is caused by the herpes simplex virus.

Embodiment 4

The method of embodiment 3, wherein the herpes simplex virus is herpes simplex virus type 1 (HSV-1).

Embodiment 5

The method of embodiment 3, wherein the herpes simplex virus is herpes simplex virus type 2 (HSV-2).

Embodiment 6

The method of embodiment 1 or 2, wherein the infection is caused by the varicella zoster virus (VZV).

Embodiment 7

The method of any one of embodiments 1-6, wherein the symptoms of the infection are selected from lesions, pain, fever, swollen lymph nodes, and any combinations thereof.

Embodiment 8

The method of any one of embodiments 1-7, wherein the pharmaceutical composition is applied topically to the eye, the skin, a mucous membrane, or any combinations thereof.

Embodiment 9

The method of embodiment 8, wherein the mucous membrane comprises the lips, the nostrils, the urethra, the vagina, the foreskin, or the anus.

Embodiment 10

The method of embodiment 8 or 9, wherein the pharmaceutical composition is applied directly to the lesions associated with the infection.

Embodiment 11

The method of any one of embodiments 1-10, wherein the reduction in severity is assessed by visually inspecting the lesions associated with the infection.

Embodiment 12

The method of embodiment 11, wherein the number of lesions is about 2 times to about 10 times smaller as compared to a non-treated infection.

Embodiment 13

The method of embodiment 11, wherein the total lesion area is about 2 times to about 10 times smaller in size as compared to a non-treated infection.

Embodiment 14

The method of any one of embodiments 1-10, wherein the reduction in severity is assessed by measuring the pain associated with the infection.

Embodiment 15

The method of embodiment 14, wherein the pain is about 2 times to about 10 times less as compared to a non-treated infection.

Embodiment 16

The method of any one of embodiments 1-10, wherein the reduction in duration is assessed by visually inspecting the lesions associated with the infection.

Embodiment 17

The method of embodiment 16, wherein the lesions crust about 2 times to about 10 times faster or clear about 2 times to about 10 times faster as compared to a non-treated infection.

Embodiment 18

The method any one of embodiments 1-17, wherein the administration provides a viral load percent reduction of at least about 96% after 5 minutes exposure.

Embodiment 19

The method any one of embodiments 1-17, wherein the administration provides a viral load percent reduction of at least about 99% after 15 minutes exposure.

Embodiment 20

The method any one of embodiments 1-17, wherein the administration provides a viral load percent reduction of at least about 99% after 60 minutes exposure.

Embodiment 21

A method of preventing the spread of an infection in a subject in need thereof, the method comprising administering to the subject in need thereof a pharmaceutical composition comprising C10-C16-alkyl (ethylbenzyl)dimethylammonium chloride.

Embodiment 22

The method of embodiment 21, wherein the infection is a viral infection.

Embodiment 23

The method of embodiment 21 or 22, wherein the infection is caused by the herpes simplex virus.

Embodiment 24

The method of embodiment 23, wherein the herpes simplex virus is herpes simplex virus type 1 (HSV-1).

Embodiment 25

The method of embodiment 23, wherein the herpes simplex virus is herpes simplex virus type 2 (HSV-2).

Embodiment 26

The method of embodiment 21 or 22, wherein the infection is caused by the human immunodeficiency virus (HIV).

Embodiment 27

The method of embodiment 21 or 22, wherein the infection is caused by the hepatitis B virus or the hepatitis C virus.

Embodiment 28

The method of embodiment 21 or 22, wherein the infection is caused by the human papillomavirus (HPV).

Embodiment 29

The method of embodiment 21 or 22, wherein the infection is caused by the ebolavirus.

Embodiment 30

The method of embodiment 21 or 22, wherein the infection is caused by an adenovirus.

Embodiment 31

The method of any one of embodiments 21-30, wherein the pharmaceutical composition is applied topically to the skin, a mucous membrane, or any combinations thereof.

Embodiment 32

The method of embodiment 34, wherein the mucous membrane comprises the lips, the nostrils, the urethra, the vagina, the foreskin, or the anus.

Embodiment 33

The method of embodiment 34, wherein the mucous membrane comprises the vagina.

Embodiment 34

A method of treating an infection in a subject in need thereof, the method comprising administering to the subject in need thereof a pharmaceutical composition comprising C10-C16-alkyl(ethylbenzyl)dimethylammonium chloride.

Embodiment 35

The method of embodiment 34, wherein the infection is a viral infection.

Embodiment 36

The method of embodiment 34 or 35, wherein the infection is caused by the human adenovirus.

Embodiment 37

The method of embodiment 36, wherein the human adenovirus is selected from Ad 3, Ad 4, Ad 5, Ad 8, Ad 19, and Ad 37.

Embodiment 38

The method of any one of embodiments 34-37, wherein the infection is epidemic keratoconjunctivitis (EKC).

Embodiment 39

The method of any one of embodiments 34-38, wherein the pharmaceutical composition is applied topically to the eye, the skin, a mucous membrane, or any combinations thereof.

Embodiment 40

The method of embodiment 39, wherein the pharmaceutical composition is applied topically to the eye.

Embodiment 41

The method any one of embodiments 34-40, wherein the infection is caused by Ad 3 and wherein the administration provides a viral load percent reduction of at least about 43% after 5 minutes exposure.

Embodiment 42

The method any one of embodiments 34-40, wherein the infection is caused by Ad 3 and wherein the administration provides a viral load percent reduction of at least about 96% after 15 minutes exposure.

Embodiment 43

The method any one of embodiments 34-40, wherein the infection is caused by Ad 3 and wherein the administration provides a viral load percent reduction of at least about 99% after 60 minutes exposure.

Embodiment 44

The method any one of embodiments 34-40, wherein the infection is caused by Ad 4 and wherein the administration provides a viral load percent reduction of at least about 68% after 5 minutes exposure.

Embodiment 45

The method any one of embodiments 34-40, wherein the infection is caused by Ad 4 and wherein the administration provides a viral load percent reduction of at least about 82% after 15 minutes exposure.

Embodiment 46

The method any one of embodiments 34-40, wherein the infection is caused by Ad 4 and wherein the administration provides a viral load percent reduction of at least about 94% after 60 minutes exposure.

Embodiment 47

The method any one of embodiments 34-40, wherein the infection is caused by Ad 5 and wherein the administration provides a viral load percent reduction of at least about 68% after 5 minutes exposure.

Embodiment 48

The method any one of embodiments 34-40, wherein the infection is caused by Ad 5 and wherein the administration provides a viral load percent reduction of at least about 94% after 15 minutes exposure.

Embodiment 49

The method any one of embodiments 34-40, wherein the infection is caused by Ad 5 and wherein the administration provides a viral load percent reduction of at least about 99% after 60 minutes exposure.

Embodiment 50

The method of any one of embodiments 1-49, wherein the method further comprises administering ammonium chloride.

Embodiment 51

The method of any one of embodiments 1-50, wherein the method further comprises administering a chlorite salt.

Embodiment 52

The method of any one of embodiments 1-51, wherein the C10-C16-alkyl(ethylbenzyl)dimethylammonium chloride is present in an amount ranging from about 0.0001% to about 10% w/w.

Embodiment 53

The method of any one of embodiments 1-51, wherein the C10-C16-alkyl(ethylbenzyl)dimethylammonium chloride is present in an amount ranging from about 0.0001% to about 5% w/w.

Embodiment 54

The method of any one of embodiments 1-51, wherein the C10-C16-alkyl(ethylbenzyl)dimethylammonium chloride is present in an amount ranging from about 0.0001% to about 4% w/w.

Embodiment 55

The method of any one of embodiments 1-51, wherein the C10-C16-alkyl(ethylbenzyl)dimethylammonium chloride is present in an amount ranging from about 0.0001% to about 3% w/w.

Embodiment 56

The method of any one of embodiments 1-51, wherein the C10-C16-alkyl(ethylbenzyl)dimethylammonium chloride is present in an amount ranging from about 0.0001% to about 2% w/w.

Embodiment 57

The method of any one of embodiments 1-51, wherein the C10-C16-alkyl(ethylbenzyl)dimethylammonium chloride is present in an amount ranging from about 0.0001% to about 1% w/w.

Embodiment 58

The method of any one of embodiments 1-51, wherein the C10-C16-alkyl(ethylbenzyl)dimethylammonium chloride is present in an amount ranging from about 0.0001% to about 0.1% w/w.

Embodiment 59

The method of any one of embodiments 1-51, wherein the C10-C16-alkyl(ethylbenzyl)dimethylammonium chloride is present in an amount ranging from about 0.0001% to about 0.01% w/w.

Embodiment 60

The method of any one of embodiments 1-51, wherein the C10-C16-alkyl(ethylbenzyl)dimethylammonium chloride is present in an amount ranging from about 0.0001% to about 0.001% w/w.

Embodiment 61

The method of any one of embodiments 1-51, wherein the C10-C16-alkyl(ethylbenzyl)dimethylammonium chloride is present in an amount ranging from about 0.001% to about 1% w/w.

Embodiment 62

The method of any one of embodiments 1-51, wherein the C10-C16-alkyl(ethylbenzyl)dimethylammonium chloride is present in an amount ranging from about 0.01% to about 1% w/w.

Embodiment 63

The method of any one of embodiments 1-51, wherein the C10-C16-alkyl(ethylbenzyl)dimethylammonium chloride is present in an amount ranging from about 0.1% to about 1% w/w.

Embodiment 64

The method of any one of embodiments 1-63, wherein the C10-C16-alkyl(ethylbenzyl)dimethylammonium chloride is C12-C14-alkyl(ethylbenzyl)dimethylammonium chloride.

Embodiment 65

The method of any one of embodiments 1-64, wherein the C10-C16-alkyl(ethylbenzyl)dimethylammonium chloride is C12-alkyl(ethylbenzyl)dimethylammonium chloride.

Embodiment 66

The method of any one of embodiments 1-64, wherein the C10-C16-alkyl(ethylbenzyl)dimethylammonium chloride is C14-alkyl(ethylbenzyl)dimethylammonium chloride.

Embodiment 67

The method of any one of embodiments 50-66, wherein the ammonium chloride is present in an amount ranging from about 0.0001% to about 10% w/w.

Embodiment 68

The method of any one of embodiments 50-66, wherein the ammonium chloride is present in an amount ranging from about 0.0001% to about 5% w/w.

Embodiment 69

The method of any one of embodiments 50-66, wherein the ammonium chloride is present in an amount ranging from about 0.0001% to about 4% w/w.

Embodiment 70

The method of any one of embodiments 50-66, wherein the ammonium chloride is present in an amount ranging from about 0.0001% to about 3% w/w.

Embodiment 71

The method of any one of embodiments 50-66, wherein the ammonium chloride is present in an amount ranging from about 0.0001% to about 2% w/w.

Embodiment 72

The method of any one of embodiments 50-66, wherein the ammonium chloride is present in an amount ranging from about 0.0001% to about 1% w/w.

Embodiment 73

The method of any one of embodiments 50-66, wherein the ammonium chloride is present in an amount ranging from about 0.0001% to about 0.1% w/w.

Embodiment 74

The method of any one of embodiments 50-66, wherein the ammonium chloride is present in an amount ranging from about 0.0001% to about 0.01% w/w.

Embodiment 75

The method of any one of embodiments 50-66, wherein the ammonium chloride is present in an amount ranging from about 0.0001% to about 0.001% w/w.

Embodiment 76

The method of any one of embodiments 50-66, wherein the ammonium chloride is present in an amount ranging from about 0.001% to about 1% w/w.

Embodiment 77

The method of any one of embodiments 50-66, wherein the ammonium chloride salt is present in an amount ranging from about 0.01% to about 1% w/w.

Embodiment 78

The method of any one of embodiments 50-66, wherein the ammonium chloride is present in an amount ranging from about 0.1% to about 1% w/w.

Embodiment 79

The method of any one of embodiments 51-78, wherein the chlorite salt is present in an amount ranging from about 0.0001% to about 10% w/w.

Embodiment 80

The method of any one of embodiments 51-78, wherein the chlorite salt is present in an amount ranging from about 0.0001% to about 5% w/w.

Embodiment 81

The method of any one of embodiments 51-78, wherein the chlorite salt is present in an amount ranging from about 0.0001% to about 4% w/w.

Embodiment 82

The method of any one of embodiments 51-78, wherein the chlorite salt is present in an amount ranging from about 0.0001% to about 3% w/w.

Embodiment 83

The method of any one of embodiments 51-78, wherein the chlorite salt is present in an amount ranging from about 0.0001% to about 2% w/w.

Embodiment 84

The method of any one of embodiments 51-78, wherein the chlorite salt is present in an amount ranging from about 0.0001% to about 1% w/w.

Embodiment 85

The method of any one of embodiments 51-78, wherein the chlorite salt is present in an amount ranging from about 0.0001% to about 0.1% w/w.

Embodiment 86

The method of any one of embodiments 51-78, wherein the chlorite salt is present in an amount ranging from about 0.0001% to about 0.01% w/w.

Embodiment 87

The method of any one of embodiments 51-78, wherein the chlorite salt is present in an amount ranging from about 0.0001% to about 0.001% w/w.

Embodiment 88

The method of any one of embodiments 51-78, wherein the chlorite salt is present in an amount ranging from about 0.001% to about 1% w/w.

Embodiment 89

The method of any one of embodiments 51-78, wherein the chlorite salt is present in an amount ranging from about 0.01% to about 1% w/w.

Embodiment 90

The method of any one of embodiments 51-78, wherein the chlorite salt is present in an amount ranging from about 0.1% to about 1% w/w.

Embodiment 91

The method of any one of embodiments 51-90, wherein the chlorite salt is an alkali metal chlorite salt.

Embodiment 92

The method of embodiment 91, wherein the alkali metal chlorite salt is sodium chlorite.

Embodiment 93

The method of embodiment 92, wherein the sodium chlorite is provided as a stabilized chlorine dioxide solution.

Embodiment 94

The method of embodiment 93, wherein the stabilized chlorine dioxide is present in an amount ranging from about 0.0001% to about 10% w/w.

Embodiment 95

The method of embodiment 93, wherein the stabilized chlorine dioxide is present in an amount ranging from about 0.0001% to about 5% w/w.

Embodiment 96

The method of embodiment 93, wherein the stabilized chlorine dioxide is present in an amount ranging from about 0.0001% to about 4% w/w.

Embodiment 97

The method of embodiment 93, wherein the stabilized chlorine dioxide is present in an amount ranging from about 0.0001% to about 3% w/w.

Embodiment 98

The method of embodiment 93, wherein the stabilized chlorine dioxide is present in an amount ranging from about 0.0001% to about 2% w/w.

Embodiment 99

The method of embodiment 93, wherein the stabilized chlorine dioxide is present in an amount ranging from about 0.0001% to about 1% w/w.

Embodiment 100

The method of embodiment 93, wherein the stabilized chlorine dioxide is present in an amount ranging from about 0.0001% to about 0.1% w/w.

Embodiment 101

The method of embodiment 93, wherein the stabilized chlorine dioxide is present in an amount ranging from about 0.0001% to about 0.01% w/w.

Embodiment 102

The method of embodiment 93, wherein the stabilized chlorine dioxide is present in an amount ranging from about 0.0001% to about 0.001% w/w.

Embodiment 103

The method of embodiment 93, wherein the stabilized chlorine dioxide is present in an amount ranging from about 0.001% to about 1% w/w.

Embodiment 104

The method of embodiment 93, wherein the stabilized chlorine dioxide is present in an amount ranging from about 0.01% to about 1% w/w.

Embodiment 105

The method of embodiment 93, wherein the stabilized chlorine dioxide is present in an amount ranging from about 0.1% to about 1% w/w.

Embodiment 106

The method of any one of embodiments 93-105, wherein the stabilized chlorine dioxide solution comprises chlorine dioxide.

Embodiment 107

The method of any one of embodiments 1-106, wherein the pharmaceutical composition is in the form of a solution, a lotion, a gel, an ointment, a cream, a foam, a paste, or any combinations thereof.

Embodiment 108

The method of any one of embodiments 1-107, wherein the pharmaceutical composition is a gel.

Embodiment 109

The method of any one of embodiments 1-107, wherein the pharmaceutical composition is an ointment.

Embodiment 110

The method of any one of embodiments 1-109, wherein the pharmaceutical composition is an ophthalmic composition suitable for topical administration to the eye.

Embodiment 111

The method of any one of embodiments 1-110, wherein the viscosity of the pharmaceutical composition is between about 500 and about 1,000,000 centipoise.

Embodiment 112

The method of any one of embodiments 1-111, wherein the pharmaceutical composition further comprises a pharmaceutically acceptable excipient.

Embodiment 113

The method of embodiment 112, wherein the pharmaceutically acceptable excipient is selected from buffers, viscosity agents, permeation enhancers, surfactants, stabilizers, emulsifiers, preservatives, thickening agents, and any combinations thereof.

EMBODIMENTS

Embodiment 1'

A method of reducing the severity or the duration of the symptoms of a viral infection in a subject in need thereof, the method comprising administering to the subject in need thereof a pharmaceutical composition comprising C12-C14-alkyl(ethylbenzyl)dimethylammonium chloride.

Embodiment 2'

The method of embodiment 1', wherein the viral infection is caused by the herpes simplex virus.

Embodiment 3'

The method of embodiment 2', wherein the herpes simplex virus is herpes simplex virus type 1 (HSV-1), herpes simplex virus type 2 (HSV-2), or varicella zoster virus (VZV).

Embodiment 4'

The method of any one of embodiment 1'-3', wherein the symptoms of the infection are selected from lesions, pain, fever, swollen lymph nodes, and any combinations thereof.

Embodiment 5'

The method of any one of embodiment 1'-4', wherein the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

Embodiment 6'

The method of any one of embodiment 1'-5', wherein the C12-C14-alkyl(ethylbenzyl)dimethylammonium chloride is C12-alkyl(ethylbenzyl)dimethylammonium chloride.

Embodiment 7'

The method of any one of embodiment 1'-6', wherein the pharmaceutical composition is essentially free of alkyl(ethylbenzyl)dimethyl ammonium salt having an alkyl of less than 12 carbons or more than 14 carbons.

Embodiment 8'

The method of any one of embodiment 1'-7', wherein the pharmaceutical composition is essentially free of benzalkonium chloride.

Embodiment 9'

The method of any one of embodiment 1'-8', wherein the C12-C14-alkyl(ethylbenzyl)dimethylammonium chloride is present in an amount ranging from about 0.0001% to about 10% w/w.

Embodiment 10'

The method of any one of embodiment 1'-9', wherein the C12-C14-alkyl(ethylbenzyl)dimethylammonium chloride is present in an amount ranging from about 0.001% to about 1% w/w.

Embodiment 11'

The method of any one of embodiment 1'-10', wherein the pharmaceutical composition is in the form of an aerosol, a solution, a lotion, a gel, an ointment, a cream, a foam, a paste, or any combinations thereof.

Embodiment 12'

The method of any one of embodiment 1'-11', wherein the subject in need thereof is immuno-compromised.

Embodiment 13'

A method of preventing the spread of a viral infection in a subject in need thereof, the method comprising administering to the subject in need thereof a pharmaceutical composition comprising C12-C14-alkyl(ethylbenzyl)dimethylammonium chloride.

Embodiment 14'

The method of embodiment 13', wherein the viral infection is caused by the influenza virus, the herpes simplex virus, the human immunodeficiency virus (HIV), the hepatitis B virus, the hepatitis C virus, the human papillomavirus (HPV), the ebolavirus, or an adenovirus.

Embodiment 15'

The method of embodiment 13' or embodiment 14', wherein the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

Embodiment 16'

The method of any one of embodiment 13'-15', wherein the C12-C14-alkyl(ethylbenzyl)dimethylammonium chloride is C12-alkyl(ethylbenzyl)dimethylammonium chloride.

Embodiment 17'

The method of any one of embodiment 13'-16', wherein the pharmaceutical composition is essentially free of alkyl (ethylbenzyl)dimethyl ammonium salt having an alkyl of less than 12 carbons or more than 14 carbons.

Embodiment 18'

The method of any one of embodiment 13'-17', wherein the pharmaceutical composition is essentially free of benzalkonium chloride.

Embodiment 19'

The method of any one of embodiment 13'-18', wherein the C12-C14-alkyl(ethylbenzyl)dimethylammonium chloride is present in an amount ranging from about 0.0001% to about 10% w/w.

Embodiment 20'

The method of any one of embodiment 13'-19', wherein the C12-C14-alkyl(ethylbenzyl)dimethylammonium chloride is present in an amount ranging from about 0.001% to about 1% w/w.

Embodiment 21'

The method of any one of embodiment 13'-20', wherein the subject in need thereof is immuno-compromised.

Embodiment 22'

A method of treating an infection in a subject in need thereof, the method comprising administering to the subject in need thereof a pharmaceutical composition comprising C12-C14-alkyl(ethylbenzyl)dimethylammonium chloride.

Embodiment 23'

The method of embodiment 22', wherein the infection is caused by the human adenovirus or epidemic keratoconjunctivitis (EKC).

Embodiment 24'

The method of embodiment 22' or embodiment 23', wherein the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

Embodiment 25'

The method of any one of embodiment 22'-24', wherein the C12-C14-alkyl(ethylbenzyl)dimethylammonium chloride is C12-alkyl(ethylbenzyl)dimethylammonium chloride.

Embodiment 26'

The method of any one of embodiment 22'-25', wherein the pharmaceutical composition is essentially free of alkyl (ethylbenzyl)dimethyl ammonium salt having an alkyl of less than 12 carbons or more than 14 carbons.

Embodiment 27'

The method of any one of embodiment 22'-26', wherein the pharmaceutical composition is essentially free of benzalkonium chloride.

Embodiment 28'

The method of any one of embodiment 22'-27', wherein the C12-C14-alkyl(ethylbenzyl)dimethylammonium chloride is present in an amount ranging from about 0.0001% to about 10% w/w.

Embodiment 29'

The method of any one of embodiment 22'-28', wherein the C12-C14-alkyl(ethylbenzyl)dimethylammonium chloride is present in an amount ranging from about 0.001% to about 1% w/w.

Embodiment 30'

The method of any one of embodiment 22'-29', wherein the subject in need thereof is immuno-compromised.

EXAMPLES

Example 1: STR-325 Formulation

| Ingredient | Concentration % w/w | Function |
| --- | --- | --- |
| C12-C14 Alkyl(ethylbenzyl)dimethylammonium chloride (80%) | 0.001 | Disinfectant |
| Stabilized chloride dioxide* | 0.01 | Disinfectant |
| Ammonium chloride | 0.20 | Disinfectant |
| Sodium phosphate monobasic (monohydrate) | 0.012 | Buffer |
| Sodium phosphate dibasic (heptahydrate) | 0.195 | Buffer |
| Sodium chloride | 0.10 | Tonicity agent |
| Potassium chloride | 0.20 | Tonicity agent |
| EDTA | 0.05 | Chelating agent |
| Tetronic ® 908 | 0.25 | Surfactant |
| Propylene glycol | 0.75 | Tonicity agent |
| Purified water | QS to 100 | Diluent |

*Stabilized chloride dioxide comprises about 3% sodium chlorite

Example 2: Exemplary Borate Based Formulation

| Ingredient | A-2 % w/w | B-2 % w/w | C-2 % w/w | D-2 % w/w | E-2 % w/w | F-2 % w/w |
| --- | --- | --- | --- | --- | --- | --- |
| Boric acid | 0.850 | 0.850 | 0.850 | 0.850 | 0.850 | 0.850 |
| Sodium borate | 0.130 | 0.130 | 0.130 | 0.130 | 0.130 | 0.130 |
| Sodium chloride | 0.250 | 0.250 | 0.250 | 0.250 | 0.250 | 0.250 |
| Potassium chloride | 0.250 | 0.250 | 0.250 | 0.250 | 0.250 | 0.250 |
| Tetronic ® 908 | 0.250 | 0.250 | 0.250 | 0.250 | 0.250 | 0.250 |
| Ammonium Chloride | — | — | — | 0.200 | 0.100 | 0.050 |
| Stabilized chlorine dioxide* | 0.04 | 0.02 | 0.01 | — | — | — |

-continued

| Ingredient | A-2 % w/w | B-2 % w/w | C-2 % w/w | D-2 % w/w | E-2 % w/w | F-2 % w/w |
|---|---|---|---|---|---|---|
| pH | 7.39/7.44 | 7.39/7.44 | 7.39/7.44 | 7.39/7.44 | 7.39/7.44 | 7.39/7.44 |
| Osmolarity | 290 | 290 | 290 | 290 | 290 | 290 |

*Stabilized chloride dioxide comprises about 3% sodium chlorite

Example 3: Exemplary Phosphate Buffer Based Formulation

| Ingredient | A-3 % w/w | B-3 % w/w | C-3 % w/w | D-3 % w/w | E-3 % w/w | F-3 % w/w |
|---|---|---|---|---|---|---|
| Sodium phosphate, heptahydrate, dibasic | 0.165 | 0.165 | 0.165 | 0.165 | 0.165 | 0.165 |
| Sodium phosphate, monohydrate, monobasic | 0.050 | 0.050 | 0.050 | 0.050 | 0.050 | 0.050 |
| Sodium chloride | 0.650 | 0.650 | 0.650 | 0.650 | 0.650 | 0.650 |
| Potassium chloride | 0.250 | 0.250 | 0.250 | 0.250 | 0.250 | 0.250 |
| Tetronic ® 908 | 0.250 | 0.250 | 0.250 | 0.250 | 0.250 | 0.250 |
| Ammonium chloride | — | — | — | 0.200 | 0.100 | 0.050 |
| Stabilized chlorine dioxide* | 0.04 | 0.02 | 0.01 | — | — | — |
| pH | 7.0 | 7.0 | 7.0 | 7.0 | 7.0 | 7.0 |
| Osmolarity | 290 | 290 | 290 | 290 | 290 | 290 |

*Stabilized chloride dioxide comprises about 3% sodium chlorite

Example 4: Exemplary Phosphate Buffer Based Formulation

| Ingredient | A-4 % w/w | B-4 % w/w | C-4 % w/w | D-4 % w/w | E-4 % w/w | F-4 % w/w |
|---|---|---|---|---|---|---|
| Sodium phosphate, heptahydrate, dibasic | 0.165 | 0.165 | 0.165 | 0.165 | 0.165 | 0.165 |
| Sodium phosphate, monohydrate, monobasic | 0.050 | 0.050 | 0.050 | 0.050 | 0.050 | 0.050 |
| Sodium chloride | 0.650 | 0.650 | 0.650 | 0.650 | 0.650 | 0.650 |
| Potassium chloride | 0.250 | 0.250 | 0.250 | 0.250 | 0.250 | 0.250 |
| Tetronic ® 908 | 0.250 | 0.250 | 0.250 | 0.250 | 0.250 | 0.250 |
| Ammonium chloride | — | 0.200 | 0.200 | — | — | — |
| Stabilized chlorine dioxide* | 0.01 | 0.01 | — | — | — | — |
| C12-C14-alkyl (ethylbenzyl) dimethyl-ammonium chloride (80%) | — | — | — | 0.050 | 0.025 | 0.0125 |
| pH | 7.0 | 7.0 | 7.0 | 7.0 | 7.0 | 7.0 |
| Osmolarity | 290 | 290 | 290 | 290 | 290 | 290 |

*Stabilized chloride dioxide comprises about 3% sodium chlorite

Example 5: Exemplary Phosphate Buffer Based Formulation

| Ingredient | A-5 % w/w | B-5 % w/w | C-5 % w/w | D-5 % w/w | E-5 % w/w | F-5 % w/w | G-5 % w/w |
|---|---|---|---|---|---|---|---|
| Sodium phosphate, heptahydrate, dibasic | 0.165 | 0.165 | 0.165 | 0.165 | 0.165 | 0.165 | 0.165 |
| Sodium phosphate, monohydrate, monobasic | 0.050 | 0.050 | 0.050 | 0.050 | 0.050 | 0.050 | 0.050 |
| Sodium chloride | 0.650 | 0.650 | 0.650 | 0.650 | 0.650 | 0.650 | 0.650 |
| Potassium chloride | 0.250 | 0.250 | 0.250 | 0.250 | 0.250 | 0.250 | 0.250 |
| Tetronic 908 | 0.250 | 0.250 | 0.250 | 0.250 | 0.250 | 0.250 | 0.250 |
| Ammonium chloride | — | — | 0.20 | — | 0.20 | 0.20 | 0.20 |
| Stabilized chlorine dioxide* | — | 0.01 | — | 0.01 | — | 0.01 | 0.01 |
| C12-C14-alkyl(ethylbenzyl) dimethylammonium chloride (80%) | 0.0125 | — | — | 0.0125 | 0.0125 | — | 0.125 |
| pH | 7.0 | 7.0 | 7.0 | 7.0 | 7.0 | 7.0 | 7.0 |
| Osmolarity | 290 | 290 | 290 | 290 | 290 | 290 | 290 |

*Stabilized chloride dioxide comprises about 3% sodium chlorite

Example 6: Exemplary Phosphate Buffer Based Formulation

| Ingredient | A-6 % w/w | B-6 % w/w | C-6 % w/w | D-6 % w/w | E-6 % w/w | F-6 % w/w | G-6 % w/w |
|---|---|---|---|---|---|---|---|
| Sodium phosphate, heptahydrate, Dibasic | 0.165 | 0.165 | 0.165 | 0.165 | 0.165 | 0.165 | 0.165 |
| Sodium phosphate, monohydrate, monobasic | 0.050 | 0.050 | 0.050 | 0.050 | 0.050 | 0.050 | 0.050 |
| Sodium chloride | 0.650 | 0.650 | 0.650 | 0.650 | 0.650 | 0.650 | 0.650 |
| Potassium chloride | 0.250 | 0.250 | 0.250 | 0.250 | 0.250 | 0.250 | 0.250 |
| Tetronic ® 908 | 0.250 | 0.250 | 0.250 | 0.250 | 0.250 | 0.250 | 0.250 |
| Ammonium chloride | 0.20 | 0.20 | 0.20 | 0.20 | 0.20 | — | — |
| Stabilized Chlorine Dioxide* | 0.01 | 0.01 | 0.01 | 0.01 | 0.01 | — | — |
| C12-C14-alkyl(ethylbenzyl) dimethylammonium chloride (80%) | 0.0125 | 0.0075 | 0.0030 | 0.0010 | 0.0001 | 0.0075 | 0.0030 |
| pH | 7.0 | 7.0 | 7.0 | 7.0 | 7.0 | 7.0 | 7.0 |
| Osmolarity | 290 | 290 | 290 | 290 | 290 | 290 | 290 |

*Stabilized chloride dioxide comprises about 3% sodium chlorite

Example 7: Exemplary Phosphate/Borate Buffered Formulation (Active Agents Only)

| | A-7 % w/w | B-7 % w/w |
|---|---|---|
| Buffer | borate | Phosphate |
| Stabilized chlorine dioxide* | 0.25 | 0.25 |
| ammonium chloride | 0.2 | 0.2 |
| C12-14-alkyl(ethylbenzyl) dimethylammoninm chloride | 0.001 | 0.001 |

*Stabilized chloride dioxide comprises about 3% sodium chlorite

In some embodiments, formulations A-7 and B-7 further contain pharmaceutically acceptable excipients.

Example 8: Exemplary Formulations (Active Agents Only)

| | A-8 % w/w | B-8 % w/w |
|---|---|---|
| Stabilized chlorine dioxide* | 0.01 | 0.01 |
| ammonium chloride | 0.2 | 0.2 |
| C12-14-alkyl(ethylbenzyl) dimethylammonium chloride (80%) | 0.001 | 0.002 |

*Stabilized chloride dioxide comprises about 3% sodium chlorite

In some embodiments, formulations A-8 and B-8 further contain pharmaceutically acceptable excipients and/or a buffer system.

Example 9: Exemplary Formulations

| ingredient | A-9 % w/w | B-9 % w/w | C-9 % w/w | D-9 % w/w | E-9 % w/w | F-9 % w/w | G-9 % w/w |
|---|---|---|---|---|---|---|---|
| Ammonium chloride | 0.25 | 0.25 | 0 | 0 | 0.25 | 0.25 | 0.00 |
| Stabilized chlorine dioxide | 0.02 | 0 | 0.02 | 0 | 0.030 | 0.040 | 0.00 |
| C12-C14-alkyl(ethylbenzyl) dimethylammonium chloride | 0.015 | 0 | 0 | 0.015 | 0.0200 | 0.0200 | 0.00 |
| Sodium phosphate, heptahydrate, dibasic | 0.195 | 0.195 | 0.195 | 0.195 | 0.195 | 0.195 | 0.195 |
| Sodium phosphate, monohydrate, monobasic | 0.012 | 0.012 | 0.012 | 0.012 | 0.012 | 0.012 | 0.012 |
| Sodium chloride | 0.10 | 0.10 | 0.10 | 0.10 | 0.10 | 0.10 | 0.10 |
| Potassium chloride | 0.20 | 0.20 | 0.20 | 0.20 | 0.20 | 0.20 | 0.20 |
| Tetronic 908 | 0.25 | 0.25 | 0.25 | 0.25 | 0.25 | 0.25 | 0.25 |
| Propylene glycol | 0.75 | 0.75 | 0.75 | 0.75 | 0.75 | 0.75 | 0.75 |
| EDTA | 0.05 | 0.05 | 0.05 | 0.05 | 0.05 | 0.05 | 0.05 |

*Stabilized chloride dioxide comprises about 3% sodium chlorite

Example 10: Evaluation of STR-325 Against Herpes Simplex Virus

The objective of this study was to evaluate the antiviral properties of STR-325 against Herpes simplex virus type-1 (HSV-1) and HSV-2 when exposed (in suspension) for the specified exposure times. This assay is derived from a protocol detailed in Standard Test Method for Efficacy of Antimicrobial Agents Against Viruses in Suspension (ASTM E 1052).

Test System

Viruses: The F(1) of HSV-1 and the G strain of HSV-2 (both obtained from American Type Culture Collection, Manassas, Va.) used for this study. Stock virus was prepared by collecting the supernatant culture fluid from 75-100% infected culture cells. The cells were disrupted and cell debris removed by centrifugation at approximately 2000 RPM for 5 minutes at 4° C. The supernatant was removed, aliquoted, and each high titer stock virus was stored at −70° C. until the day of use. On the day of use an aliquot of each stock virus was removed, thawed and maintained at a refrigerated temperature until used in the assay. The stock virus cultures were adjusted to contain 1% fetal bovine serum (FBS) as the organic soil load. Each of the stock viruses tested demonstrated cytopathic effects (CPE) typical of HSV on Vero cells.

Treatment of Virus Suspension:

A 1.80 mL aliquot of the test substance was dispensed into a sterile tube and mixed with a 200 µl aliquot of either stock virus suspension. The mixture was vortex mixed for 10 seconds and held for the remainder of the specified exposure times at 37° C. The exposure times assayed were 5, 15, or 60 minutes contact time. Immediately following each exposure time, a 100 µl aliquot was removed from the tube and the mixtures were immediately titered by 10-fold serial dilutions (100 µl+0.9 mL test medium) and assayed for the presence of virus.

Treatment of Virus Control:

A 200 µl aliquot of stock virus suspension was exposed to a 1.80 ml aliquot of test medium in lieu of test substance and treated as previously described. Immediately following each exposure time, a 100 µl aliquot was removed from the tube and the mixtures were immediately titered by 10-fold serial dilutions (100 µl+0.9 mL test medium) and assayed for the presence of virus. All controls employed the FBS neutralizer. A virus control was performed for each exposure time. The virus control titer was used as a baseline to compare the percent and log reductions of each test parameter following exposure to the test substance.

Cytotoxicity Control:

A 1.80 mL aliquot of the test substance was mixed with a 200 µl aliquot of test medium containing organic soil load in lieu of virus and treated as previously described. The cytotoxicity control was held for 60 minutes. The cytotoxicity of the cell cultures was scored at the same time as virus-test substance and virus control cultures. Cytotoxicity was graded on the basis of cell viability as determined microscopically. Cellular alterations due to toxicity were graded and reported as toxic if greater than or equal to 50% of the monolayer was affected.

Neutralization Control:

Each cytotoxicity control mixture was challenged with low titer stock virus to determine the dilution(s) of test substance at which virucidal activity, if any, was retained. Dilutions that showed virucidal activity were not considered in determining reduction of the virus by STR-325. Using the cytotoxicity control dilutions, an additional set of indicator cell cultures was inoculated with a 100 µl aliquot of each dilution in quadruplicate. A 100 µl aliquot of low titer stock virus was inoculated into each cell culture well and the indicator cell cultures were incubated along with the test and virus control plates.

Infectivity Assay:

The Vero cell line, which exhibits cytopathic effect (CPE) in the presence of HSV, was used as the indicator cell line in the infectivity assays. Cells in multiwell culture dishes were inoculated in quadruplicate with 100 µl of the dilutions prepared from test and control groups. Uninfected indicator cell cultures (cell controls) were inoculated with test medium alone. The cultures were incubated at 37° C. in a humidified atmosphere of 6% $CO_2$ in sterile disposable cell culture labware. The cultures were scored periodically for 7 days for the absence or presence of CPE, cytotoxicity, and for viability.

Cytotoxicity and Neutralization Controls:

STR-325 cytotoxicity was not observed in the cytotoxicity control at any dilution tested (<1.50 $log_{10}$). The neutralization control demonstrated that the test substance was neutralized at <1.50 $log_{10}$.

Study Results:

Tabular results for viral inhibition are found in Table 1.

HSV-1:

For the 5 minute exposure, a 2.00 $log_{10}$ reduction in viral titer (99.0%) was demonstrated. For the 15 minute exposure, a 4.00 $log_{10}$ reduction in viral titer (99.99%) reduction in viral titer was demonstrated. For the 60 minute exposure, >4.50 $log_{10}$ reduction in viral titer (?99.997%) reduction in viral titer (complete inactivation) was demonstrated.

HSV-2:

For the 5 minute exposure, a 1.50 $log_{10}$ reduction in viral titer (96.84%) was demonstrated. For the 15 minute exposure, a 2.00 $log_{10}$ reduction in viral titer (99.0%) reduction in viral titer was demonstrated. For the 60 minute exposure, 4.00 $log_{10}$ reduction in viral titer (99.99%) reduction in viral titer was demonstrated.

TABLE 1

HSV cogntrols and viral inhibition results for STR-325

|  |  | Exposure time (minutes) | | |
| --- | --- | --- | --- | --- |
|  |  | 5 | 15 | 60 |
| HSV-1 | Control ($TCID_{50}$/100 µl) | 6.00 | 6.25 | 6.00 |
|  | $Log_{10}$ Reduction | 2.00 | 4.00 | ≥4.50 |
|  | Percent Reduction | 98.84 | 99.99 | ≥99.997 |
| HSV-2 | Control ($TCID_{50}$/100 µl) | 6.00 | 5.75 | 6.00 |
|  | $Log_{10}$ Reduction | 1.50 | 2.00 | 4.00 |
|  | Percent Reduction | 96.84 | 99.0 | 99.99 |

HSV-1 and HSV-2 samples were mixed with STR-325 and formulation A-8, respectively, in vitro for distinct time intervals, then a plaque assay was performed to quantify remaining viral particles. 1.8 mL of sterilant was mixed with 200 µL viral stock solution and held at 37° C. for the exposure times of 5, 15, and 60 min. At each exposure time point, 100 µL aliquot was titered 10-fold serial dilutions (100 µL+0.9 mL test medium) with Test Medium (Minimum Essential Medium (MEM)+5% (v/v) heat-inactivated fetal bovine serum (FBS), 10 µg/mL gentamicin, 100 units/mL penicillin and 2.5 µg/mL amphotericin B). Vero cells in multiwell culture were inoculated with 100 µL of each dilution, in quadruplicate. Cell controls were inoculated with Test Medium alone. Cultures were incubated at 37° C. in humidified 6% CO2. Cultures were scored periodically for 7 days for CPE, cytotoxicity, and viability.

Additional tabular results for viral inhibition are found in Table 2 and Table 3.

TABLE 2

HSV-1 controls and viral inhibition results for STR-325

| | HSV-1 + STR-325 | | |
|---|---|---|---|
| Dilution | Exposure Time 5 min | Exposure Time 15 min | Exposure Time 60 min |
| Cell Control | 0000 | 0000 | 0000 |
| $10^{-2}$ | ++++ | 0000 | 0000 |
| $10^{-3}$ | 0+0+ | 0000 | 0000 |
| $10^{-4}$ | 0000 | 0000 | 0000 |
| $10^{-5}$ | 0000 | 0000 | 0000 |
| $10^{-6}$ | 0000 | 0000 | 0000 |
| $10^{-7}$ | 0000 | 0000 | 0000 |
| $10^{-8}$ | 0000 | 0000 | 0000 |
| $TCID_{50}/100\ \mu L$ | $10^{3.00}$ | $\leq 10^{1.50}$ | $\leq 10^{1.50}$ |
| Percent reduction | 99.97% | ≥99.994% | ≥99.98% |

(+) = positive for the presence of test virus
(0) = no test virus and/or no cytotoxicity present

TABLE 3

HSV-2 controls and viral inhibition results for formulation A-8

| | Virus Control | | | HSV-2 + formulation A-8 Exposure Time | | |
|---|---|---|---|---|---|---|
| Dilution | 5 min | 15 min | 60 min | 5 min | 15 min | 60 min |
| Cell Control | 0000 | 0000 | 0000 | 000 | 000 | 000 |
| $10^{-2}$ | ++++ | ++++ | ++++ | ++++ | ++++ | 00++ |
| $10^{-3}$ | ++++ | ++++ | ++++ | ++++ | ++++ | 0000 |
| $10^{-4}$ | ++++ | ++++ | ++++ | ++++ | 000+ | 0000 |
| $10^{-5}$ | ++0+ | ++++ | 0+++ | 0000 | 0000 | 0000 |
| $10^{-6}$ | +00+ | 0+00 | +0++ | 0000 | 0000 | 0000 |
| $10^{-7}$ | 000+ | 0000 | 0000 | 0000 | 0000 | 0000 |
| $10^{-8}$ | 0000 | 0000 | 0000 | 0000 | 0000 | 0000 |
| $TCID_{50}/100\ \mu L$ | $10^{6.00}$ | $10^{5.75}$ | $10^{6.00}$ | $10^{4.50}$ | $10^{3.75}$ | $10^{2.00}$ |
| % reduction | NA | NA | NA | 96.84% | 99% | 99.99% |
| $Log_{10}$ Reduction | NA | NA | NA | $1.50\ log_{10}$ | $2.00\ log_{10}$ | $4.00\ log_{10}$ |

(+) = positive for the presence of test virus
(0) = no test virus and/or no cytotoxicity present
(NA) = Not applicable

Example 11: Evaluation of Formulation A-9 Through G-9 Against Herpes Simplex Virus Experimental Summary For each test pharmaceutical composition, a suspension of virus was exposed to the test substance. At each predetermined exposure time an aliquot was removed, neutralized by serial dilution, and assayed for the presence of virus. The exposure times were 60 minutes and 4 hours. The virus controls, cytotoxicity controls, and neutralization controls were assayed in parallel. Antiviral properties of each test substance were evaluated and compared at the specified concentration and time intervals.

Test Parameters
  Dilution: None
  Vitus: Herpes simplex vines type 1, ATCC VR-733, Strain F(1)
  Exposure Times: 60 minutes and 4 hours
  Exposure Temperature: Room temperature (23.5° C.)
  Organic Soil Load: 1% fetal bovine serum
  Test Medium: Minimum Essential Medium (MEM) supplemented with 5% (v/v) heat-inactivated fetal bovine serum (FBS), 10 μg/ml gentamicin, 100 units/ml penicillin, and 2.5 μg/ml amphotericin B
  Indicator Cell Cultures: Vero cells Results Formulation A-9, B-9, C-9, D-9, E-9, F-9, and G-9 demonstrated the following percent and log reductions in viral titer following 60 minute and 4 hour exposure times at room temperature (23.5° C.) to Herpes simplex virus type 1, as compared to the titer of the corresponding virus (Table 4)

TABLE 4

| Formulation | 60 Minute Exposure | 4 Hour Exposure |
|---|---|---|
| A-9 | ≥99.99% reduction | ≥99.994% reduction |
| | ≥4.00 $log_{10}$ reduction | ≥4.25 $log_{10}$ reduction |
| B-9 | No reduction | 43.8% reduction |
| | | 0.25 $log_{10}$ reduction |
| C-9 | No reduction | 43.8% reduction |
| | | 0.25 $log_{10}$ reduction |
| D-9 | ≥99.99% reduction | ≥99.994% reduction |
| | ≥4.00 $log_{10}$ reduction | ≥4.25 $log_{10}$ reduction |
| E-9 | ≥99.99% reduction | ≥99.994% reduction |
| | ≥4.00 $log_{10}$ reduction | ≥4.25 $log_{10}$ reduction |

TABLE 4-continued

| Formulation | 60 Minute Exposure | 4 Hour Exposure |
|---|---|---|
| F-9 | ≥99.99% reduction | ≥99.994% reduction |
| | ≥4.00 $log_{10}$ reduction | ≥4.25 $log_{10}$ reduction |
| G-9 | No reduction | No reduction |

The individual results are shown in the tables below:

TABLE 5

Virus Control Results

| | Virus Control | |
|---|---|---|
| Dilution | Exposure Time 60 Minutes | Exposure Time 4 Hours |
| Cell Control | 0 0 0 0 | 0 0 0 0 |
| $10^{-2}$ | + + + + | + + + + |
| $10^{-3}$ | + + + + | + + + + |

TABLE 5-continued

Virus Control Results

| Dilution | Virus Control Exposure Time 60 Minutes | Exposure Time 4 Hours |
|---|---|---|
| $10^{-4}$ | + + + + | + + + + |
| $10^{-5}$ | + + + + | + + + + |
| $10^{-6}$ | 0 0 0 0 | + 0 0 0 |
| $10^{-7}$ | 0 0 0 0 | 0 0 0 0 |
| $TCID_{50}/100\ \mu L$ | $10^{5.50}$ | $10^{5.75}$ |

(+) = Positive for the presence of test virus
(0) = No test virus recovered and/or no cytotoxicity present

TABLE 6

Effects of Formulation A-9 Against Herpes Simplex Virus Type 1 in Suspension Following 60 Minute and 4 Hour Exposure Times

| Dilution | Test: Herpes simplex virus type 1 + Formulation A-9 Exposure Time 60 Minutes | Exposure Time 4 Hours | Cytotoxicity Control | Neutralization Control |
|---|---|---|---|---|
| Cell Control | 0 0 0 0 | 0 0 0 0 | 0 0 0 0 | 0 0 0 0 |
| $10^{-2}$ | 0 0 0 0 | 0 0 0 0 | 0 0 0 0 | + + + + |
| $10^{-3}$ | 0 0 0 0 | 0 0 0 0 | 0 0 0 0 | + + + + |
| $10^{-4}$ | 0 0 0 0 | 0 0 0 0 | 0 0 0 0 | + + + + |
| $10^{-5}$ | 0 0 0 0 | 0 0 0 0 | NT | NT |
| $10^{-6}$ | 0 0 0 0 | 0 0 0 0 | NT | NT |
| $10^{-7}$ | 0 0 0 0 | 0 0 0 0 | NT | NT |
| $TCID_{50}/100\ \mu L$ | $\leq 10^{1.50}$ | $\leq 10^{1.50}$ | $*\leq 10^{1.50}$ | Neutralized at a $TCID_{50}/100\ \mu L$ of $\leq 1.50\ Log_{10}$ |
| % Reduction | $\geq 99.99\%$ | $\geq 99.994\%$ | NA | NA |
| Log Reduction | $\geq 4.00\ Log_{10}$ | $\geq 4.25\ Log_{10}$ | NA | NA |

(+) = Positive for the presence of test virus
(0) = No test virus recovered and/or no cytotoxicity present
*= Cytotoxicity control reported as $TCD_{50}/100\ \mu L$
(NA) = Not applicable
(NT) = Not tested

TABLE 7

Effects of Formulation B-9 Against Herpes Simplex Virus Type 1 in Suspension Following 60 Minute and 4 Hour Exposure Times

| Dilution | Test: Herpes simplex virus type 1 + Formulation B-9 Exposure Time 60 Minutes | Exposure Time 4 Hours | Cytotoxicity Control | Neutralization Control |
|---|---|---|---|---|
| Cell Control | 0 0 0 0 | 0 0 0 0 | 0 0 0 0 | 0 0 0 0 |
| $10^{-2}$ | + + + + | + + + + | 0 0 0 0 | + + + + |
| $10^{-3}$ | + + + + | + + + + | 0 0 0 0 | + + + + |
| $10^{-4}$ | + + + + | + + + + | 0 0 0 0 | + + + + |
| $10^{-5}$ | + + + + | + + + + | NT | NT |
| $10^{-6}$ | + + + + | 0 0 0 0 | NT | NT |
| $10^{-7}$ | 0 0 0 0 | 0 0 0 0 | NT | NT |
| $TCID_{50}/100\ \mu L$ | $10^{6.50}$ | $10^{5.50}$ | $*\leq 10^{1.50}$ | Neutralized at a $TCID_{50}/100\ \mu L$ of $\leq 1.50\ Log_{10}$ |
| % Reduction | No Reduction | 43.8% | NA | NA |

TABLE 7-continued

Effects of Formulation B-9 Against Herpes Simplex Virus Type 1 in Suspension Following 60 Minute and 4 Hour Exposure Times

| Dilution | Test: Herpes simplex virus type 1 + Formulation B-9 Exposure Time 60 Minutes | Exposure Time 4 Hours | Cytotoxicity Control | Neutralization Control |
|---|---|---|---|---|
| Log Reduction | No Reduction | $0.25\ Log_{10}$ | NA | NA |

(+) = Positive for the presence of test virus
(0) = No test virus recovered and/or no cytotoxicity present
*= Cytotoxicity control reported as $TCD_{50}/100\ \mu L$
(NA) = Not applicable
(NT) = Not tested

TABLE 8

Effects of Formulation C-9 Against Herpes Simplex Virus Type 1 in Suspension Following 60 Minute and 4 Hour Exposure Times

| Dilution | Test: Herpes simplex virus type 1 + Formulation C-9 Exposure Time 60 Minutes | Exposure Time 4 Hours | Cytotoxicity Control | Neutralization Control |
|---|---|---|---|---|
| Cell Control | 0 0 0 0 | 0 0 0 0 | 0 0 0 0 | 0 0 0 0 |
| $10^{-2}$ | + + + + | + + + + | 0 0 0 0 | + + + + |
| $10^{-3}$ | + + + + | + + + + | 0 0 0 0 | + + + + |
| $10^{-4}$ | + + + + | + + + + | 0 0 0 0 | + + + + |
| $10^{-5}$ | + + + + | + + + + | NT | NT |
| $10^{-6}$ | + 0 0 + | 0 0 0 0 | NT | NT |
| $10^{-7}$ | 0 0 0 0 | 0 0 0 0 | NT | NT |
| $TCID_{50}/100\ \mu L$ | $10^{6.00}$ | $10^{5.50}$ | $*\leq 10^{1.50}$ | Neutralized at a $TCID_{50}/100\ \mu L$ of $\leq 1.50\ Log_{10}$ |
| % Reduction | No Reduction | 43.8% | NA | NA |
| Log Reduction | No Reduction | $0.25\ Log_{10}$ | NA | NA |

(+) = Positive for the presence of test virus
(0) = No test virus recovered and/or no cytotoxicity present
*= Cytotoxicity control reported as $TCD_{50}/100\ \mu L$
(NA) = Not applicable
(NT) = Not tested

TABLE 9

Effects of Formulation D-9 Against Herpes Simplex Virus Type 1 in Suspension Following 60 Minute and 4 Hour Exposure Times

| Dilution | Test: Herpes simplex virus type 1 + Formulation D-9 Exposure Time 60 Minutes | Exposure Time 4 Hours | Cytotoxicity Control | Neutralization Control |
|---|---|---|---|---|
| Cell Control | 0 0 0 0 | 0 0 0 0 | 0 0 0 0 | 0 0 0 0 |
| $10^{-2}$ | 0 0 0 0 | 0 0 0 0 | 0 0 0 0 | + + + + |
| $10^{-3}$ | 0 0 0 0 | 0 0 0 0 | 0 0 0 0 | + + + + |
| $10^{-4}$ | 0 0 0 0 | 0 0 0 0 | 0 0 0 0 | + + + + |
| $10^{-5}$ | 0 0 0 0 | 0 0 0 0 | NT | NT |
| $10^{-6}$ | 0 0 0 0 | 0 0 0 0 | NT | NT |
| $10^{-7}$ | 0 0 0 0 | 0 0 0 0 | NT | NT |
| $TCID_{50}/$ | $\leq 10^{1.50}$ | $\leq 10^{1.50}$ | $*\leq 10^{1.50}$ | Neutralized at a |

TABLE 9-continued

Effects of Formulation D-9 Against Herpes Simplex Virus Type 1 in Suspension Following 60 Minute and 4 Hour Exposure Times

| Dilution | Test: Herpes simplex virus type 1 + Formulation D-9 | | Cytotoxicity Control | Neutralization Control |
|---|---|---|---|---|
| | Exposure Time 60 Minutes | Exposure Time 4 Hours | | |
| 100 μL | | | | $TCID_{50}/100$ μL of $\leq 1.50$ $Log_{10}$ |
| % Reduction | $\geq 99.99\%$ | $\geq 99.994\%$ | NA | NA |
| Log Reduction | $\geq 4.00$ $Log_{10}$ | $\geq 4.25$ $Log_{10}$ | NA | NA |

(+) = Positive for the presence of test virus
(0) = No test virus recovered and/or no cytotoxicity present
*= Cytotoxicity control reported as $TCD_{50}/100$ μL
(NA) = Not applicable
(NT) = Not tested

TABLE 10

Effects of Formulation E-9 Against Herpes Simplex Virus Type 1 in Suspension Following 60 Minute and 4 Hour Exposure Times

| Dilution | Test: Herpes simplex virus type 1 + Formulation E-9 | | Cytotoxicity Control | Neutralization Control |
|---|---|---|---|---|
| | Exposure Time 60 Minutes | Exposure Time 4 Hours | | |
| Cell Control | 0 0 0 0 | 0 0 0 0 | 0 0 0 0 | 0 0 0 0 |
| $10^{-2}$ | 0 0 0 0 | 0 0 0 0 | 0 0 0 0 | + + + + |
| $10^{-3}$ | 0 0 0 0 | 0 0 0 0 | 0 0 0 0 | + + + + |
| $10^{-4}$ | 0 0 0 0 | 0 0 0 0 | 0 0 0 0 | + + + + |
| $10^{-5}$ | 0 0 0 0 | 0 0 0 0 | NT | NT |
| $10^{-6}$ | 0 0 0 0 | 0 0 0 0 | NT | NT |
| $10^{-7}$ | 0 0 0 0 | 0 0 0 0 | NT | NT |
| $TCID_{50}/$ 100 μL | $\leq 10^{1.50}$ | $\leq 10^{1.50}$ | *$\leq 10^{1.50}$ | Neutralized at a $TCID_{50}/100$ μL of $\leq 1.50$ $Log_{10}$ |
| % Reduction | $\geq 99.99\%$ | $\geq 99.994\%$ | NA | NA |
| Log Reduction | $\geq 4.00$ $Log_{10}$ | $\geq 4.25$ $Log_{10}$ | NA | NA |

(+) = Positive for the presence of test virus
(0) = No test virus recovered and/or no cytotoxicity present
*= Cytotoxicity control reported as $TCD_{50}/100$ μL
(NA) = Not applicable
(NT) = Not tested

TABLE 11

Effects of Formulation F-9 Against Herpes Simplex Virus Type 1 in Suspension Following 60 Minute and 4 Hour Exposure Times

| Dilution | Test: Herpes simplex virus type 1 + AS Formulation F-9 | | Cytotoxicity Control | Neutralization Control |
|---|---|---|---|---|
| | Exposure Time 60 Minutes | Exposure Time 4 Hours | | |
| Cell Control | 0 0 0 0 | 0 0 0 0 | 0 0 0 0 | 0 0 0 0 |
| $10^{-2}$ | 0 0 0 0 | 0 0 0 0 | 0 0 0 0 | + + + + |
| $10^{-3}$ | 0 0 0 0 | 0 0 0 0 | 0 0 0 0 | + + + + |
| $10^{-4}$ | 0 0 0 0 | 0 0 0 0 | 0 0 0 0 | + + + + |

TABLE 11-continued

Effects of Formulation F-9 Against Herpes Simplex Virus Type 1 in Suspension Following 60 Minute and 4 Hour Exposure Times

| Dilution | Test: Herpes simplex virus type 1 + AS Formulation F-9 | | Cytotoxicity Control | Neutralization Control |
|---|---|---|---|---|
| | Exposure Time 60 Minutes | Exposure Time 4 Hours | | |
| $10^{-5}$ | 0 0 0 0 | 0 0 0 0 | NT | NT |
| $10^{-6}$ | 0 0 0 0 | 0 0 0 0 | NT | NT |
| $10^{-7}$ | 0 0 0 0 | 0 0 0 0 | NT | NT |
| $TCID_{50}/$ 100 μL | $\leq 10^{1.50}$ | $\leq 10^{1.50}$ | *$\leq 10^{1.50}$ | Neutralized at a $TCID_{50}/100$ μL of $\leq 1.50$ $Log_{10}$ |
| % Reduction | $\geq 99.99\%$ | $\geq 99.994\%$ | NA | NA |
| Log Reduction | $\geq 4.00$ $Log_{10}$ | $\geq 4.25$ $Log_{10}$ | NA | NA |

(+) = Positive for the presence of test virus
(0) = No test virus recovered and/or no cytotoxicity present
*= Cytotoxicity control reported as $TCD_{50}/100$ μL
(NA) = Not applicable
(NT) = Not tested

TABLE 12

Effects of Formulation G-9 Against Herpes Simplex Virus Type 1 in Suspension Following 60 Minute and 4 Hour Exposure Times

| Dilution | Test: Herpes simplex virus type 1 + Formulation G-9 | | Cytotoxicity Control | Neutralization Control |
|---|---|---|---|---|
| | Exposure Time 60 Minutes | Exposure Time 4 Hours | | |
| Cell Control | 0 0 0 0 | 0 0 0 0 | 0 0 0 0 | 0 0 0 0 |
| $10^{-2}$ | + + + + | + + + + | 0 0 0 0 | + + + + |
| $10^{-3}$ | + + + + | + + + + | 0 0 0 0 | + + + + |
| $10^{-4}$ | + + + + | + + + + | 0 0 0 0 | + + + + |
| $10^{-5}$ | + + + + | + + + + | NT | NT |
| $10^{-6}$ | + 0 0 + | 0 0 0 + | NT | NT |
| $10^{-7}$ | 0 0 0 0 | 0 0 0 0 | NT | NT |
| $TCID_{50}/$ 100 μL | $10^{6.00}$ | $10^{5.75}$ | *$\leq 10^{1.50}$ | Neutralized at a $TCID_{50}/100$ μL of $\leq 1.50$ $Log_{10}$ |
| % Reduction | No Reduction | No Reduction | NA | NA |
| Log Reduction | No Reduction | No Reduction | NA | NA |

(+) = Positive for the presence of test virus
(0) = No test virus recovered and/or no cytotoxicity present
*= Cytotoxicity control reported as $TCD_{50}/100$ μL
(NA) = Not applicable
(NT) = Not tested Example 12: In-Vivo Evaluation of Formulation A-8 Against Herpes Simplex Virus (HSV-1)

Figure 1B:
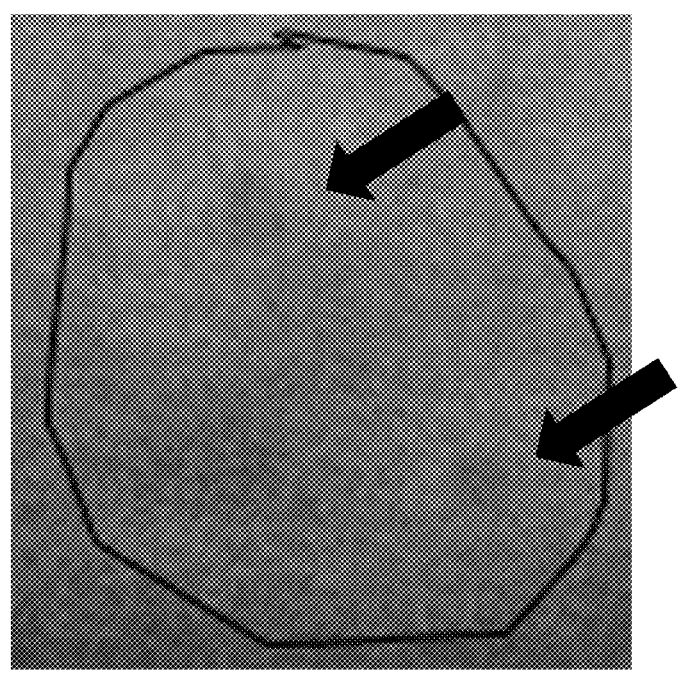
FIG. 1B shows an enlarged view of a mouse topically inoculated with $10^5$ PFU of HSV-1 (control). Arrow: herpetic lesions.
Figure 2A:
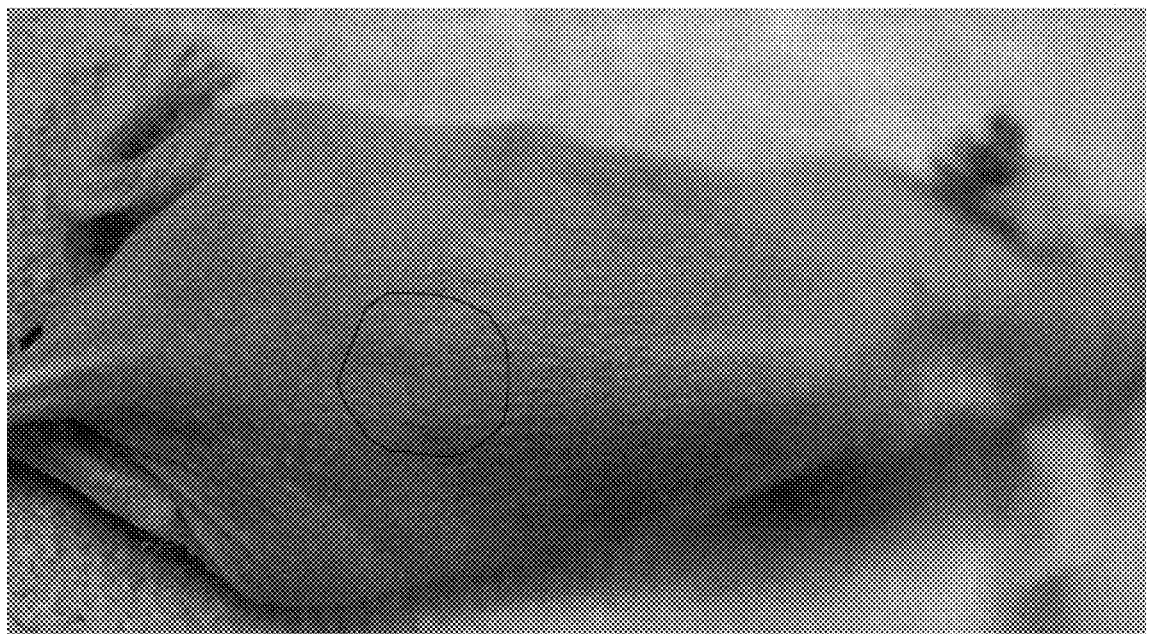
FIG. 2A shows a formulation A-8 treated mouse topically inoculated with $10^5$ PFU of HSV-1 (treatment).
Figure 2B:
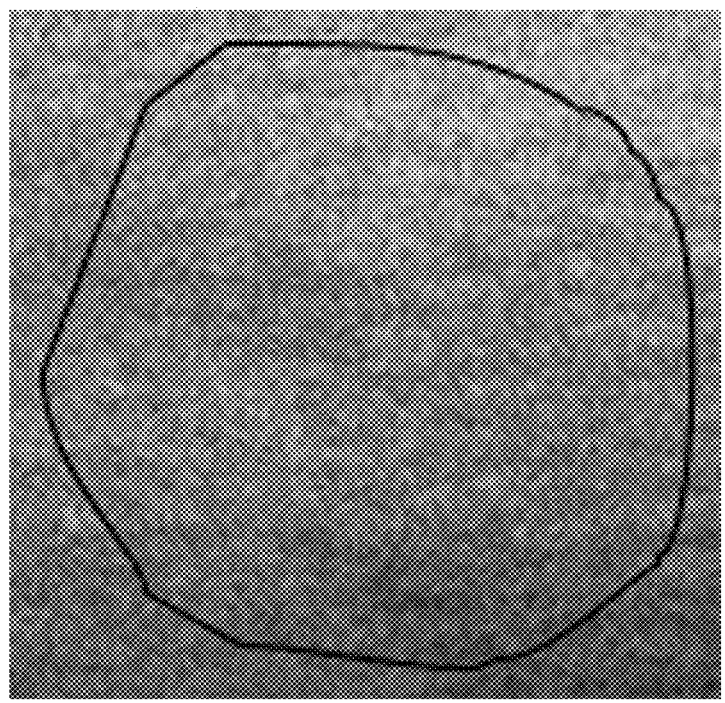
FIG. 2B shows an enlarged view of a formulation A-8 mouse topically inoculated with $10^5$ PFU of HSV-1 (treatment).

Animals were scarified and then topically inoculated with 105 PFU of HSV-1 (McKrae strain). The viral strains used in the inoculations were hypervirulent which shortened normal lesion development. Formulation A-8 inhibits lesion formation in a murine model of HSV-1 infection as can be seen in FIG. 1A and FIG. 1B (control) and FIG. 2A and FIG. 2B (treatment).

Example 13: Evaluation of Formulation B-8 Against Adenoviruses hAd 3, hAd 4, and hAd 5 samples were mixed with formulation B-8 in vitro for distinct time intervals then a plaque assay was performed to quantify remaining viral particles. A viral suspension in test medium (Minimum Essential Medium (MEM)+5% (v/v) heat inactivated fetal bovine serum (FBS)+10 μg/mL gentamicin+100 units/mL penicillin+2.5 μg/mL amphotericin B) was exposed to the sterilant at time intervals of 5, 15, and 60 minutes at 37° C. Viral plaque assay using an indicator cell culture of A-549 human lung carcinoma was used to evaluate viral activity after sterilization.

Tabular results for viral inhibition are found in Table 13, Table 14, and Table 15.

TABLE 13 hAd 3 controls and viral inhibition results for formulation B-8

| | Adenovirus Type 3 + Formulation B-8 | | |
|---|---|---|---|
| Dilution | Exposure Time 5 min | Exposure Time 15 min | Exposure Time 60 min |
| Cell Control | 0000 | 0000 | 0000 |
| $10^{-2}$ | ++++ | ++++ | ++++ |
| $10^{-3}$ | ++++ | ++++ | ++++ |
| $10^{-4}$ | ++++ | ++++ | 0000 |
| $10^{-5}$ | ++++ | ++++ | 0000 |
| $10^{-6}$ | ++++ | +000 | 0000 |
| $10^{-7}$ | 0000 | 0000 | 0000 |
| $10^{-8}$ | 0000 | 0000 | 0000 |
| $TCID_{50}$/100 μL | $10^{5.50}$ | $10^{5.75}$ | $10^{3.50}$ |
| % reduction | 43.8% | 96.8% | 99.94% |
| Log Reduction | 0.25 $log_{10}$ | 1.50 $log_{10}$ | 3.25 $log_{10}$ |

(+) = positive for the presence of test virus
(0) = no test virus and/or no cytotoxicity present

TABLE 14 hAd 4 controls and viral inhibition results for formulation B-8

| | Adenovirus Type 4 + Formulation B-8 | | |
|---|---|---|---|
| Dilution | Exposure Time 5 min | Exposure Time 15 min | Exposure Time 60 min |
| Cell Control | 0000 | 0000 | 0000 |
| $10^{-2}$ | ++++ | ++++ | ++++ |
| $10^{-3}$ | ++++ | ++++ | ++++ |
| $10^{-4}$ | ++++ | ++++ | ++++ |
| $10^{-5}$ | ++++ | ++++ | 0+++ |
| $10^{-6}$ | 0+0+ | +0+0 | 0000 |
| $10^{-7}$ | 0000 | 0000 | 0000 |
| $10^{-8}$ | 0000 | 0000 | 0000 |
| $TCID_{50}$/100 μL | $10^{6.00}$ | $10^{5.00}$ | $10^{5.25}$ |
| % reduction | 68.4% | 82.2% | 94.4% |

(+) = positive for the presence of test virus
(0) = no test virus and/or no cytotoxicity present

TABLE 15 hAd 5 controls and viral inhibition results for formulation B-8

| | Adenovirus Type 5 + Formulation B-8 | | |
|---|---|---|---|
| Dilution | Exposure Time 5 min | Exposure Time 15 min | Exposure Time 60 min |
| Cell Control | 0000 | 0000 | 0000 |
| $10^{-2}$ | ++++ | ++++ | ++++ |
| $10^{-3}$ | ++++ | ++++ | ++++ |
| $10^{-4}$ | ++++ | ++++ | ++++ |
| $10^{-5}$ | ++++ | ++++ | 00++ |
| $10^{-6}$ | ++++ | ++++ | 0000 |
| $10^{-7}$ | +00+ | 000+ | 0000 |
| $10^{-8}$ | 0000 | 0000 | 0000 |
| $TCID_{50}$/100 μL | $10^{7.00}$ | $10^{6.75}$ | $10^{5.00}$ |
| % reduction | 68.4% | 94.4% | 99.9% |

(+) = positive for the presence of test virus
(0) = no test virus and/or no cytotoxicity present

Example 14: Evaluation of Formulation A-8 Against Simian Varicella Virus (SVV)

Results of the SVV exposure to formulation A-8 are presented in Table 16. Exposure time of only 5 minutes eliminated 99.99% of SVV. The longer times were 100% virus free. SVV is a surrogate virus for the human virus VZV.

TABLE 16

SVV controls and viral inhibition results for formulation A-8

| | Virus Control | | | Simian Varicella Virus + formulation A-8 | | |
|---|---|---|---|---|---|---|
| | Exposure Time | | | | | |
| Dilution | 5 min | 15 min | 60 min | 5 min | 15 min | 60 min |
| Cell Control | 000 | 000 | 000 | 000 | 000 | 000 |
| $10^{-2}$ | +++ | +++ | +++ | +00 | 000 | 000 |
| $10^{-3}$ | ++++ | ++++ | ++++ | 0000 | 0000 | 0000 |
| $10^{-4}$ | ++++ | ++++ | ++++ | 0000 | 0000 | 0000 |
| $10^{-5}$ | 0000 | 0000 | 0000 | 0000 | 0000 | 0000 |
| $10^{-6}$ | 0000 | 0000 | 0000 | 0000 | 0000 | 0000 |
| $10^{-7}$ | 0000 | 0000 | 0000 | 0000 | 0000 | 0000 |
| $10^{-8}$ | 0000 | 0000 | 0000 | 0000 | 0000 | 0000 |
| $TCID_{50}$/100 μL | $10^{4.1}$ | $10^{4.2}$ | $10^{4.0}$ | $10^{1.7}$ | 0.00 | 0.00 |
| % reduction | NA | NA | NA | 99.99% | 100% | 100% |
| $Log_{10}$ Reduction | NA | NA | NA | 2.4 $log_{10}$ | 4.1 $log_{10}$ | 4.1 $log_{10}$ |

Example 15: Evaluation of Formulation A-8 Against HIV

Figure 3A:
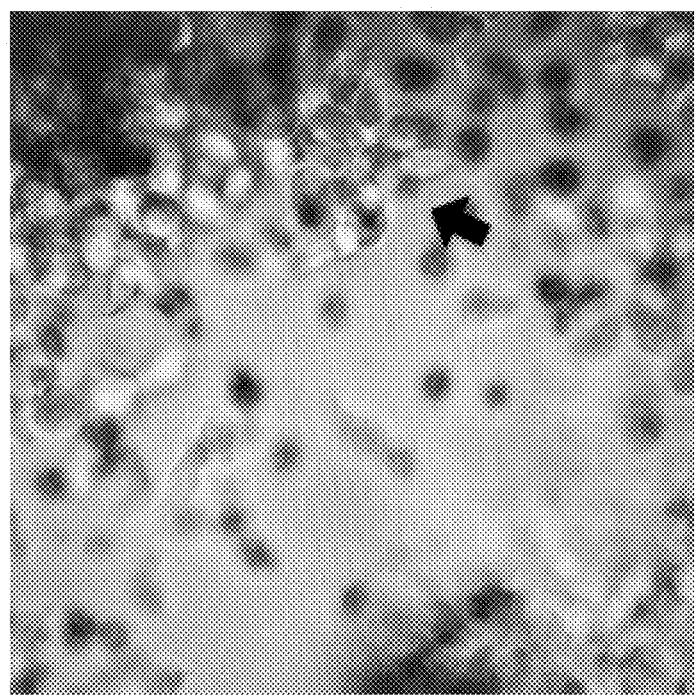
FIG. 3A shows uninfected CEM x174 cells treated with saline. Arrow: normal, healthy clumping cells.
Figure 3B:
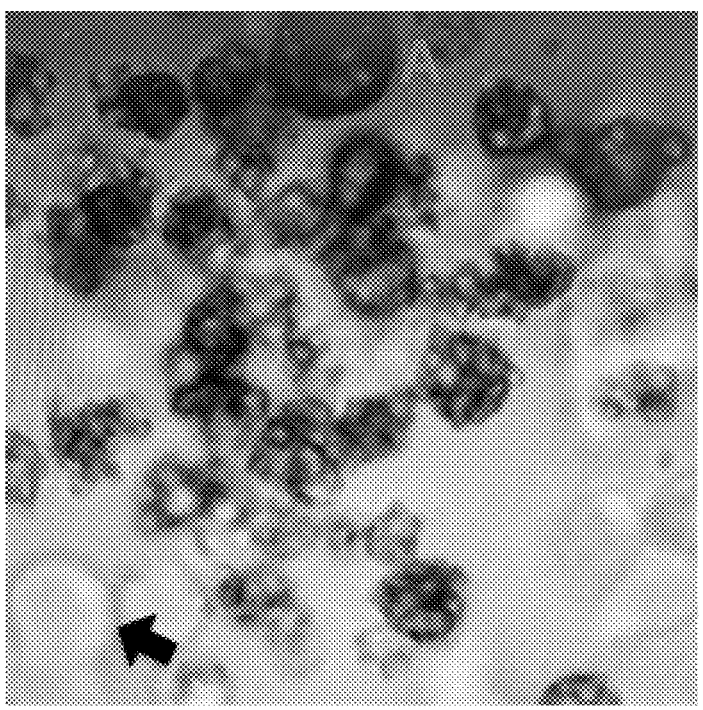
FIG. 3B shows infected CEM x174 cells treated with saline. Arrow: syncytia. A: dead giant cell.
Figure 3C:
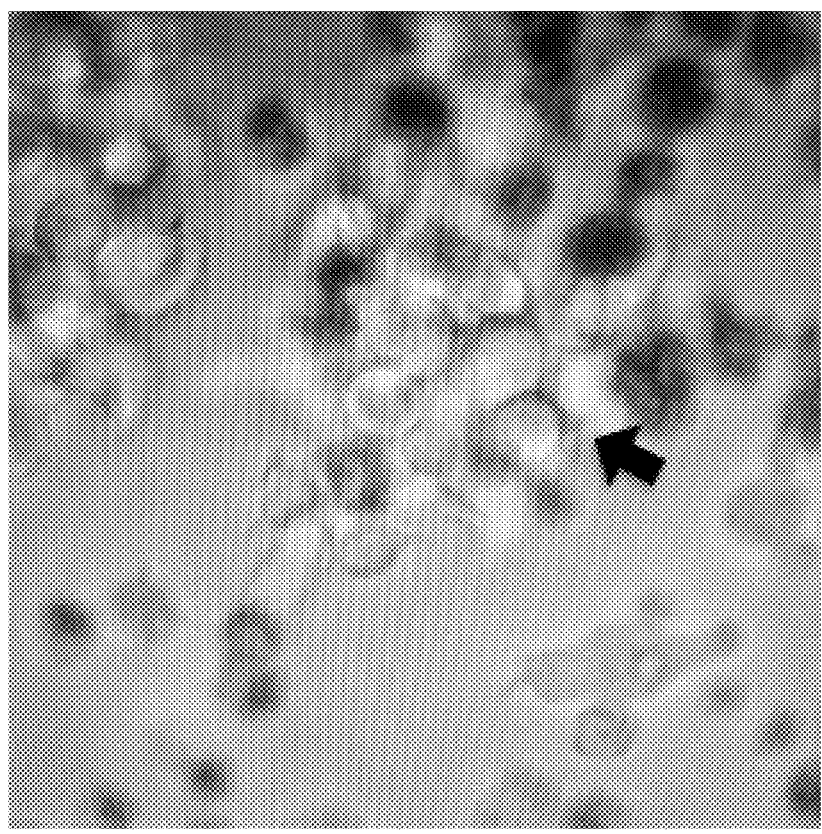
FIG. 3C shows infected CEM x174 cells treated with Formulation A-8 (5 minute contact time). Arrow: normal, healthy clumping cells.

CEMx174 cells and MT-4 cells were cultured in RPMI-1640 media+10% FBS+5% pen/strep+5% L-glutamine at a density of $0.5 \times 10^6$ cells/mL, centrifuged at 1500 rpm for 10 min, and resuspended at $10 \times 10^6$ cells/mL. 200 μL cell suspension per well was aliquoted into a U-bottom 96-well plate, centrifuged at 1500 rpm for 10 min, and washed with PBS. 200 μL Formulation A-8 was added undiluted, 1:10, and 1:100 and incubated at 37° C. for 30 min. Cell viability was assayed via Trypan Blue assay. Results can be seen in FIG. 3A (normal cells), FIG. 3B (syncytia and dead giant cell), and FIG. 3C (treated cells). Syncytia form when cells are infected with certain types of viruses such as HIV. These syncytial formations create distinctive cytopathic effects when seen in permissive cells. Because many cells fuse together, syncytium are also known as multinucleated giant cells or polykaryocytes. During infection, viral fusion proteins used by the virus to enter the cell are transported to the cell surface, where they can cause the host cell membrane to fuse with neighboring cells. Formulation A-8 completely inhibits HIV-2F.

Example 16: Guinea Pig Maximization Test

The purpose of this study is to assess the potential of Formulation A-8 to cause delayed dermal contact sensitization in a guinea pig maximization test (OECD Guidelines for the Testing of Chemicals guideline No. 429 of 23 Jul. 2010).

Methods: Fifteen (15) Dunkin Hartley guinea pigs, weighing between 300-500 g were used in this study. Ten (10) animals were assigned to the test group and five (5) animals were assigned to the control group. On Day 1 (Induction Phase), animals were shaved in the intrascapular region, the area was cleansed with IPA and each animal received 3 rows of paired intradermal injections (0.1 mL) (one on either side of the spine) in an approximately 4 cm×2 cm area as described below:

| Test Group | Control Group |
|---|---|
| 50:50 (v/v) FCA:control | 50:50 (v/v) FCA:control |
| Formulation A-8 (neat) | Control (neat) |
| 1:1 (v/v) of Formulation A-8 in 50:50 (v/v) FCA:control | 1:1 (v/v) of control in 50:50 (v/v) FCA:control |

FCA: Freunds Complete Adjuvant
Control: 0.9% sodium chloride for injection

Day 7 (±1 day): The fur over the area injected was shaved. The area was treated with 10% sodium lauryl sulfate (SLS) in petrolatum to provoke a mild acute inflammation. The 10% SLS was massaged into the skin and the area was left uncovered until the following day.

Induction Phase

Day 8 (±1 day; 24±2 hours after the application of the 10% SLS): No residual 10% SLS was observed therefore gentle removal with a gauze pad was not necessary. A 2 cm×4 cm piece of gel blot paper was saturated with 0.50 mL of the test or control article. The saturated piece of gel blot paper was place over the previously injected sites. The paper was covered with an adhesive bandage and secured firmly by wrapping an adhesive tape around the torso of the animal. The patch remained in place for 48±2 hours. The bandages were checked for placement three times over the 48-hour exposure period.

Day 10 (±1 day [48±2 hours after patching]): The dressing and patches were removed. The exposed site was assessed for irritation between 1 and 8 hours following bandage removal.

Challenge Phase

Day 24 (±1 day [14±1 days after removal of the patch]): Approximately a 5 cm×5 cm area on each flank of the animals was clipped free of fur. A 2 cm×2 cm piece of gel blot paper saturated with the test article (0.25 mL) was placed on the right flank of each animal. The left flank was similarly treated with the control article. The patches were secured in place as described above and remained in place for 24±2 hours.

Day 25 ((±1 day [24±2 hours after patching]): The dressing and patches were removed. At 24±2 hours and 48±2 hours after removal, the skin was evaluated for adverse reaction using the criteria in the table 17. All scored were recorded.

TABLE 17

Magnusson and Kligman grading scale for the evaluation of challenge patch test reactions

| Patch Test Reaction | Grading Score |
|---|---|
| No visible change | 0 |
| Discrete or patchy erythema | 1 |
| Moderate and confluent erythema | 2 |
| Intense erythema and/or swelling | 3 |

The data for Formulation A-8 can be seen in Table 18:

TABLE 18

Study results:

| | | | | 24 Hour Score | | 48 Hour Score | |
|---|---|---|---|---|---|---|---|
| Animal | Sex | Group | St Wt. (g) | Left Side | Right Side | Left Side | Right Side |
| 1 | F | Test | 365.4 | 0 | 0 | 0 | 0 |
| 2 | F | Test | 377.7 | 0 | 0 | 0 | 0 |
| 3 | F | Test | 412.7 | 0 | 0 | 0 | 0 |
| 4 | F | Test | 390.6 | 0 | 0 | 0 | 0 |
| 5 | F | Test | 392.4 | 0 | 0 | 0 | 0 |
| 6 | M | Test | 412.4 | 0 | 0 | 0 | 0 |
| 7 | M | Test | 413.3 | 0 | 0 | 0 | 0 |
| 8 | M | Test | 405.4 | 0 | 0 | 0 | 0 |
| 9 | M | Test | 395.9 | 0 | 0 | 0 | 0 |
| 10 | M | Test | 409.1 | 0 | 0 | 0 | 0 |
| 11 | F | Control | 385.8 | 0 | 0 | 0 | 0 |
| 12 | F | Control | 370.1 | 0 | 0 | 0 | 0 |
| 13 | F | Control | 383.8 | 0 | 0 | 0 | 0 |
| 14 | M | Control | 411.8 | 0 | 0 | 0 | 0 |
| 15 | M | Control | 397.5 | 0 | 0 | 0 | 0 |

Data Assessment and Statistical Analysis

Grades of 1 or greater in any individual animal the test group generally indicates sensitization, provided that grades of less than 1 are seen in the control animals. If grades of 1 or greater are noted in the control animals, then the reactions of the test animals which exceed the most severe reaction in control animals were presumed to be due to sensitization.

Occasionally, test animals may have a greater incidence of skin reactions which are comparable in intensity to controls, without a single animal being more reactive. In these instances, a re-challenge may be necessary to clearly define the response. If necessary a re-challenge shall be carried out approximately 7 to 14 days after the first challenge. The method used shall be as described for the first challenge, using another area (e.g., abdomen) of the animals.

Statistical analysis of the data is not readily applicable to this study design. If necessary, unpaired t-test or a Mann-Whitney Rank Sum Test may be used. In the final analysis of the data, the overall patter, intensity, duration and character of the test article compared to the control article was considered.

Observations:

Mortality/Moribundity: No animals died or underwent unscheduled euthanasia during the course of the study. No abnormal findings were observed. There were no findings considered to be related to the test or control articles.

Body Weights: Weights were recording at study initiation. No evidence of extreme weight loss was identified during daily observations.

Food Consumption: Food consumption was normal during the course of the study.

Sensitization Scores: The test and negative control animals did not exhibit signs of sensitization. All scores were zero.

Conclusion:

There were no signs of sensitization observed in the guinea pigs treated with Formulation A-8. Therefore Formulation A-8 is not considered to elicit delayed dermal contact sensitization under the conditions employed.

Example 17: Evaluation of A-17 and B-17 Against Herpes Simplex Virus

Original stock solutions:

|  |  | Concentration (mg/mL) |
|---|---|---|
| A-17 | C12-C14-alkyl(ethylbenzyl)-dimethylammonium chloride | 1 |
| B-17 | benzalkonium chloride | 10 |

Experimental Summary

A suspension of virus was exposed to the use dilutions of the products. At the each pre-determined exposure time an aliquot was removed, neutralized by serial dilution, and assayed for the presence of virus. The virus controls, cytotoxicity controls, and neutralization controls were assayed in parallel. Antiviral properties of the solutions were evaluated and compared at the specified concentrations and time intervals.

Test Parameters

Dilutions: FS (undiluted) defined as 1 ml test substance+0 ml PBS
  1:10 defined as 1 ml test substance+9 ml PBS
  1:100 defined as 1 ml of the 1:10 dilution+9 ml PBS
Virus: Herpes simplex virus type 1, ATCC VR-733, Strain F(1)
Exposure Time: 15 minutes and 60 minutes
Exposure Temperature: Room temperature (22.0° C.)
Organic Soil Load: 1% fetal bovine serum
Test Medium: Minimum Essential Medium (MEM) supplemented with 5% (v/v) heat-inactivated fetal bovine serum (FBS), 10 µg/ml gentamicin, 100 units/ml penicillin, and 2.5 µg/ml amphotericin B.
Indicator Cell Cultures: Vero Results Solutions A-17 and B-17 demonstrated the following percent and log reductions in viral titer following a 15 and 60 minute exposure time to Herpes simplex virus type 1, as compared to the titer of the corresponding virus (Table 19 and 20)

TABLE 19

| Sol. | Dilution | 15 minutes exposure |
|---|---|---|
| A-17 | FS | ≥99.999% reduction (≥5.00 $\log_{10}$ reduction) |
|  | 1:10 | ≥99.999% reduction (≥5.00 $\log_{10}$ reduction) |
|  | 1:100 | 68.4% reduction (0.5 $\log_{10}$ reduction) |
| B-17 | FS | ≥99.99% reduction (≥4.00 $\log_{10}$ reduction) |
|  | 1:10 | ≥99.999% reduction (≥5.00 $\log_{10}$ reduction) |
|  | 1:100 | 90.0% reduction (1 $\log_{10}$ reduction) |

TABLE 20

| Sol. | Dilution | 60 minutes exposure |
|---|---|---|
| A-17 | FS | ≥99.998% (≥4.75 $\log_{10}$ reduction) |
|  | 1:10 | ≥99.998% (≥4.75 $\log_{10}$ reduction) |
|  | 1:100 | No reduction |

TABLE 20-continued

| Sol. | Dilution | 60 minutes exposure |
|---|---|---|
| B-17 | FS | ≥99.98% (≥3.75 $\log_{10}$ reduction) |
|  | 1:10 | ≥99.998% (≥4.75 $\log_{10}$ reduction) |
|  | 1:100 | 99.7% reduction (2.5 $\log_{10}$ reduction) |

Figure 4B:
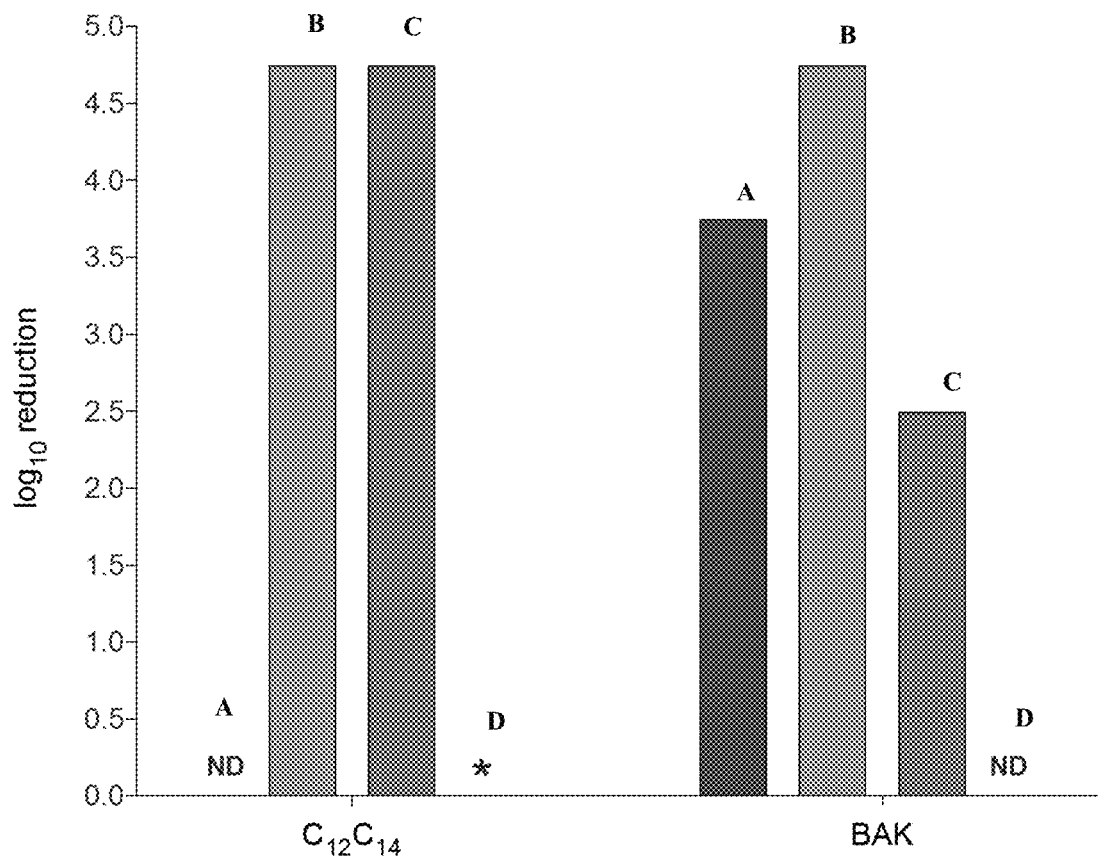
FIG. 4B shows a graphical representation of the antiviral properties against HSV-1 strain of A-17 and B-17 at 60 minutes exposure.

The graphical representations can be seen in FIGS. 4A and 4B.

Example 18: Evaluation of A-18 Through C-18 Against Herpes Simplex Virus

Original stock solutions:

|  |  | Concentration (mg/mL) |
|---|---|---|
| A-18 | C12-alkyl(ethylbenzyl) dimethylammonium chloride | 1 |
| B-18 | C14-alkyl(ethylbenzyl) dimethylammonium chloride | 1 |
| C-18 | benzalkonium chloride | 1 |
| D-18 | C12-C14-alkyl(ethylbenzyl)dimethylammonium chloride | 1 |

Experimental Summary

A suspension of virus was exposed to the use dilutions of the products. At the end of the exposure time, an aliquot was removed, neutralized by serial dilution, and assayed for the presence of virus. The virus controls, cytotoxicity controls, and neutralization controls were assayed in parallel. Antiviral properties of the solutions were evaluated and compared at the specified concentrations and time intervals.

Test Parameters

Dilutions: 1:5 defined as 1 ml test substance+4 parts sterile PBS=0.2 mg/ml
  1:10 defined as 1 ml test substance+9 parts sterile PBS=0.1 mg/ml
  1:15 defined as 1 ml test substance+14 parts sterile PBS=0.07 mg/ml
  1:20 defined as 1 ml test substance+19 parts sterile PBS=0.05 mg/ml
  1:25 defined as 1 ml test substance+24 parts sterile PBS=0.04 mg/ml
Virus: Herpes simplex virus type 1, ATCC VR-733, Strain F(1)
Exposure Time: 30 minutes
Exposure Temperature: Room temperature (22.0° C.)
Organic Soil Load: 1% fetal bovine serum
Test Medium: Minimum Essential Medium (MEM) supplemented with 5% (v/v) heat-inactivated fetal bovine serum (FBS), 10 m/ml gentamicin, 100 units/ml penicillin, and 2.5 µg/ml amphotericin B.
Indicator Cell Cultures: Vero Results Solutions A-18, B-18, C-18, and D-18 demonstrated the following percent and log reductions in viral titer following a 30 minute exposure time to Herpes simplex virus type 1, as compared to the titer of the corresponding virus (Table 21)

TABLE 21

| Solution | Dilution | % Reduction | $\log_{10}$ Reduction |
|---|---|---|---|
| A-18 | 1:5 | ≥99.997% | ≥4.5 |
|  | 1:10 | 99.4% | 2.25 |

TABLE 21-continued

| Solution | Dilution | % Reduction | Log$_{10}$ Reduction |
|---|---|---|---|
|  | 1:15 | 98.2% | 1.75 |
|  | 1:20 | 96.8% | 1.5 |
|  | 1:25 | 90.0% | 1 |
| B-18 | 1:5 | 94.4% | 1.24 |
|  | 1:10 | 43.8% | 0.25 |
|  | 1:15 | No Reduction | No Reduction |
|  | 1:20 | No Reduction | No Reduction |
|  | 1:25 | No Reduction | No Reduction |
| C-18 | 1:5 | 43.8% | 0.25 |
|  | 1:10 | No Reduction | No Reduction |
|  | 1:15 | No Reduction | No Reduction |
|  | 1:20 | No Reduction | No Reduction |
|  | 1:25 | No Reduction | No Reduction |
| D-18 | 1:5 | 99.0% | 2.00 |
|  | 1:10 | 43.8% | 0.25 |
|  | 1:15 | 43.8% | 0.25 |
|  | 1:20 | No Reduction | No Reduction |
|  | 1:25 | No Reduction | No Reduction |

Figure 5:
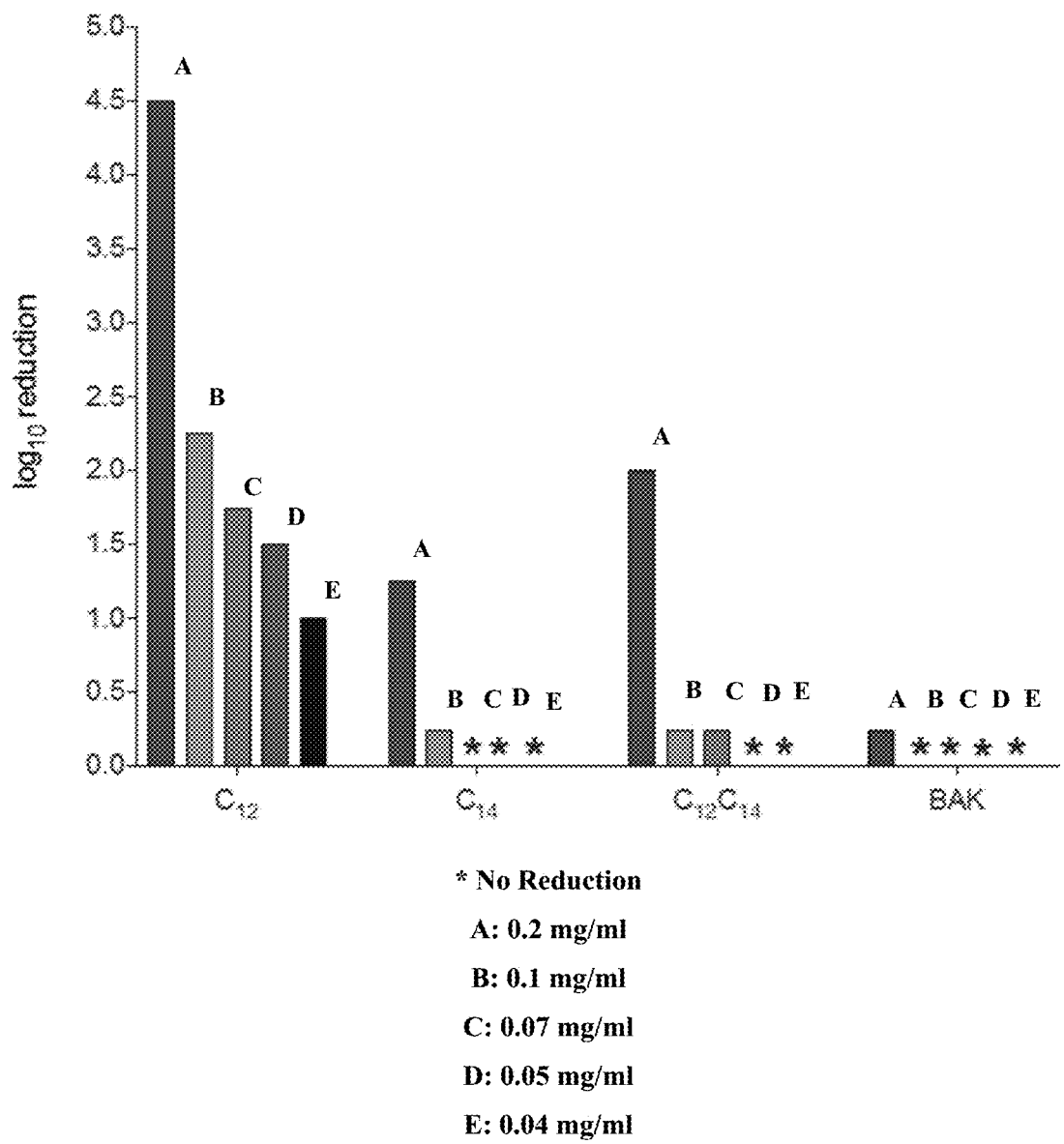
FIG. 5 shows a graphical representation of the antiviral properties against HSV-1 strain of A-18, B-18, C-18, and D-18 at 30 minutes exposure.

The graphical representation can be seen in FIG. 5.

Figure 6:
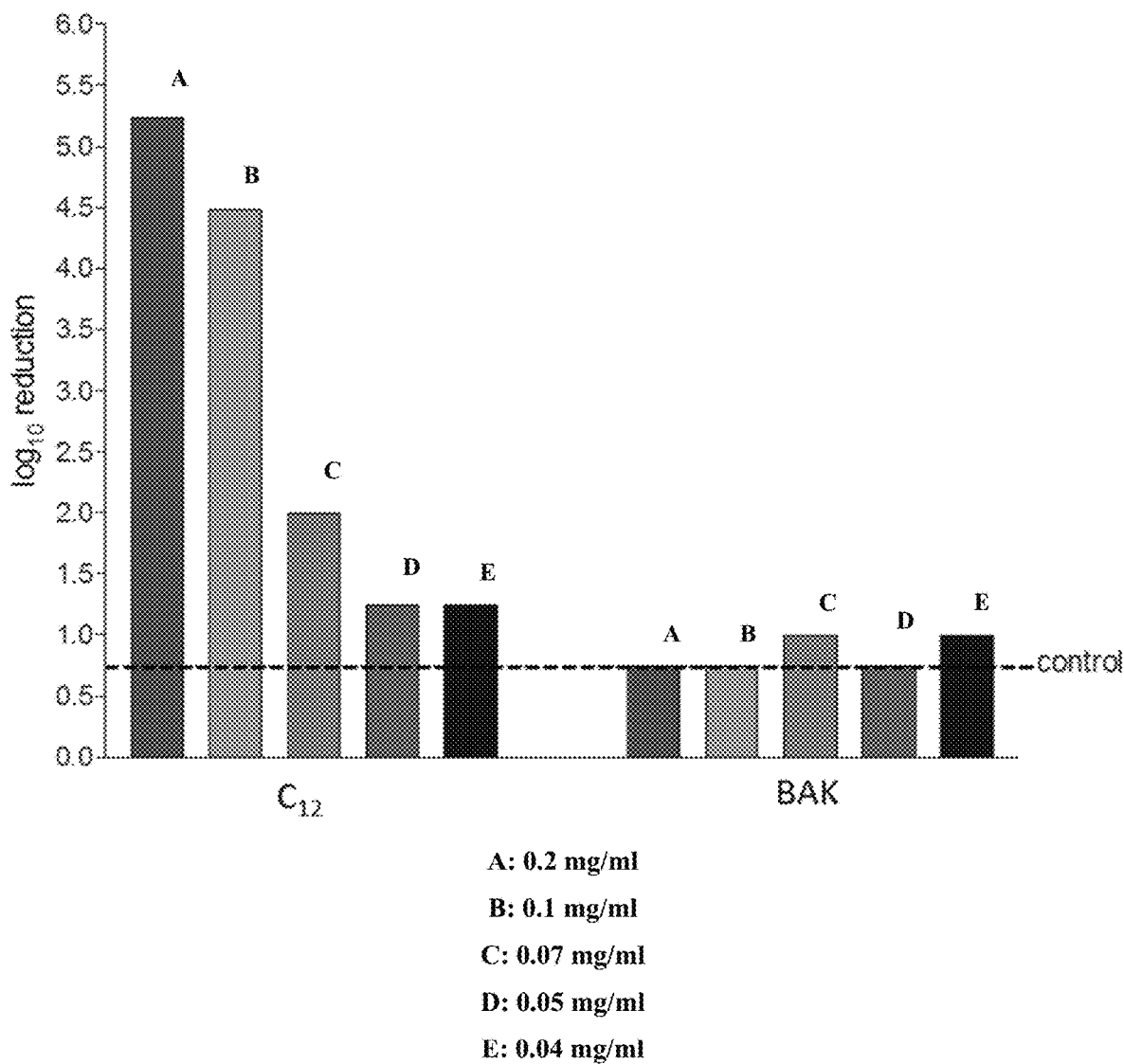
FIG. 6 shows a graphical representation of the antiviral properties against HSV-1 strain of A-18 and C-18 at 15 minutes exposure.

A similar experiment was run with 15 minutes contact time. The graphical representation can be seen in FIG. 6. Solution A-18 shows complete inactivation (99.997%; 6.75 log$_{10}$ reduction) at 15 minutes contact time. Comparator (solution C-18) showed no viral inhibitory effect at comparable concentrations.

Example 19: Hairless Mouse HSV-1 Infection Model (Rash Score)

Figure 7A:
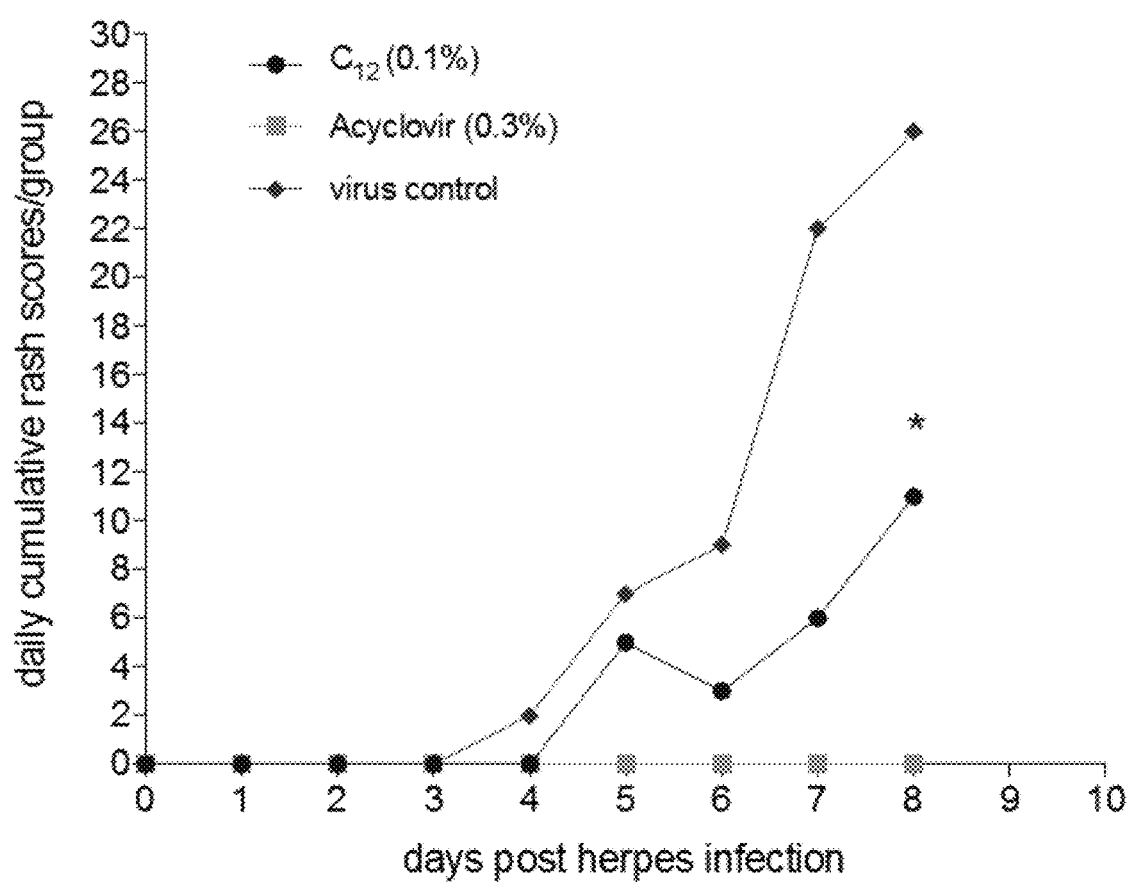
FIG. 7A shows a graphical comparison between C12-alkyl(ethylbenzyl) dimethylammonium chloride, acyclovir and virus control in a hairless mouse HSV-1 infection model (rash score).
Figure 7B:
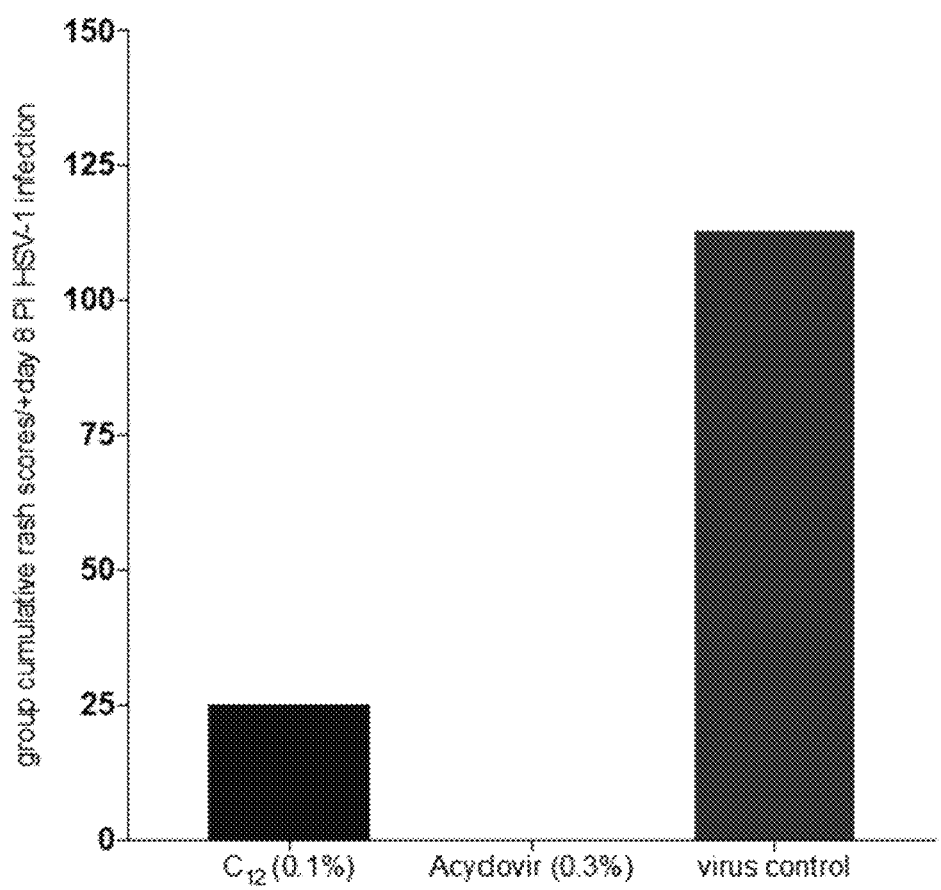
FIG. 7B shows the cumulative rash score comparison between C12-alkyl(ethylbenzyl) dimethylammonium chloride, acyclovir and virus control in a hairless mouse HSV-1 infection model (in bar graph).
Figure 9:
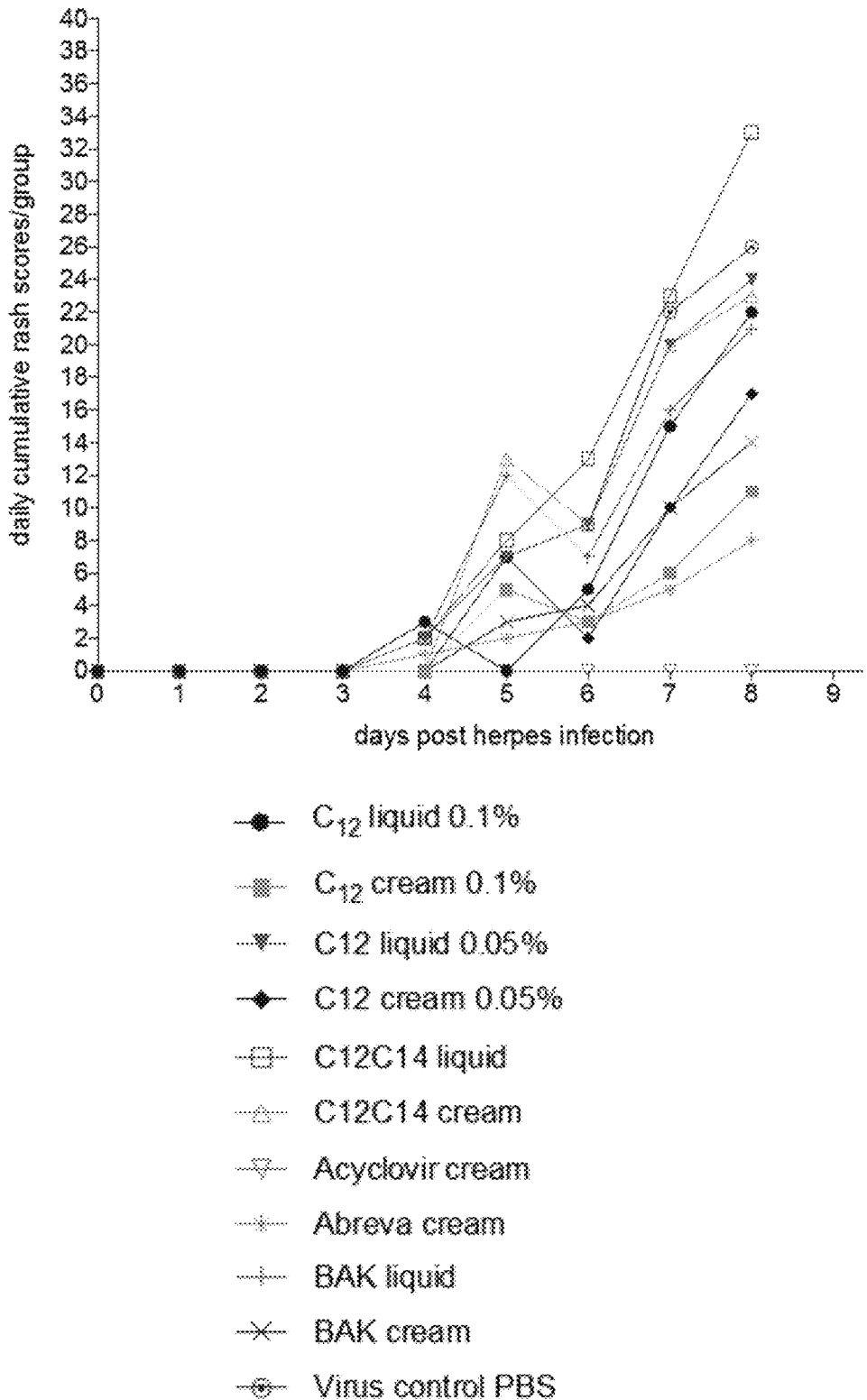
FIG. 9 shows the daily rash scores, +8 d Post-Infection, 0 h initiation of Rx.
Figure 10:
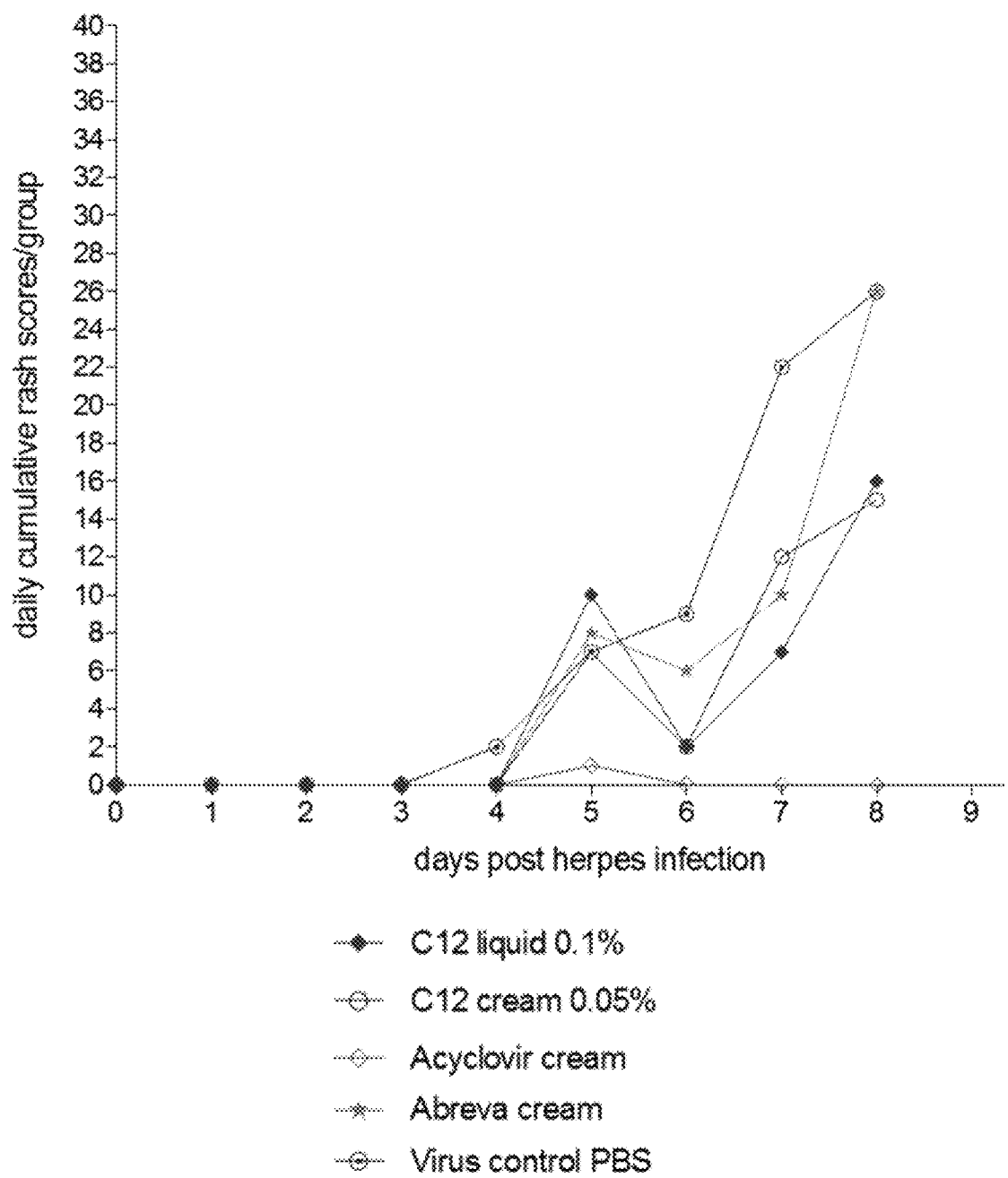
FIG. 10 shows the daily rash scores +8 d Post-Infection, +8 h initiation of Rx.
Figure 11:
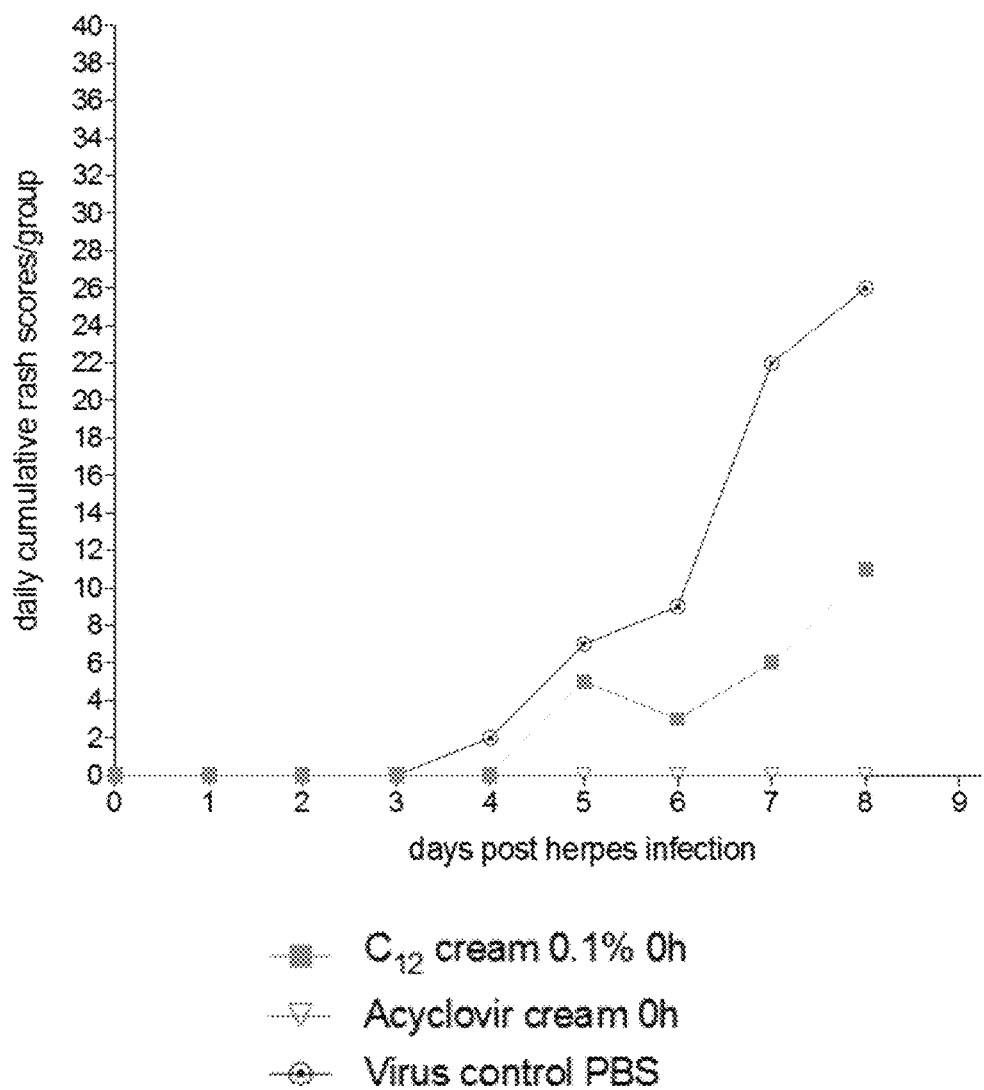
FIG. 11 shows the daily rash scores +8 d Post-Infection, C12-alkyl(ethylbenzyl) dimethylammonium chloride, acyclovir, virus control, 0 h initiation of Rx.
Figure 12:
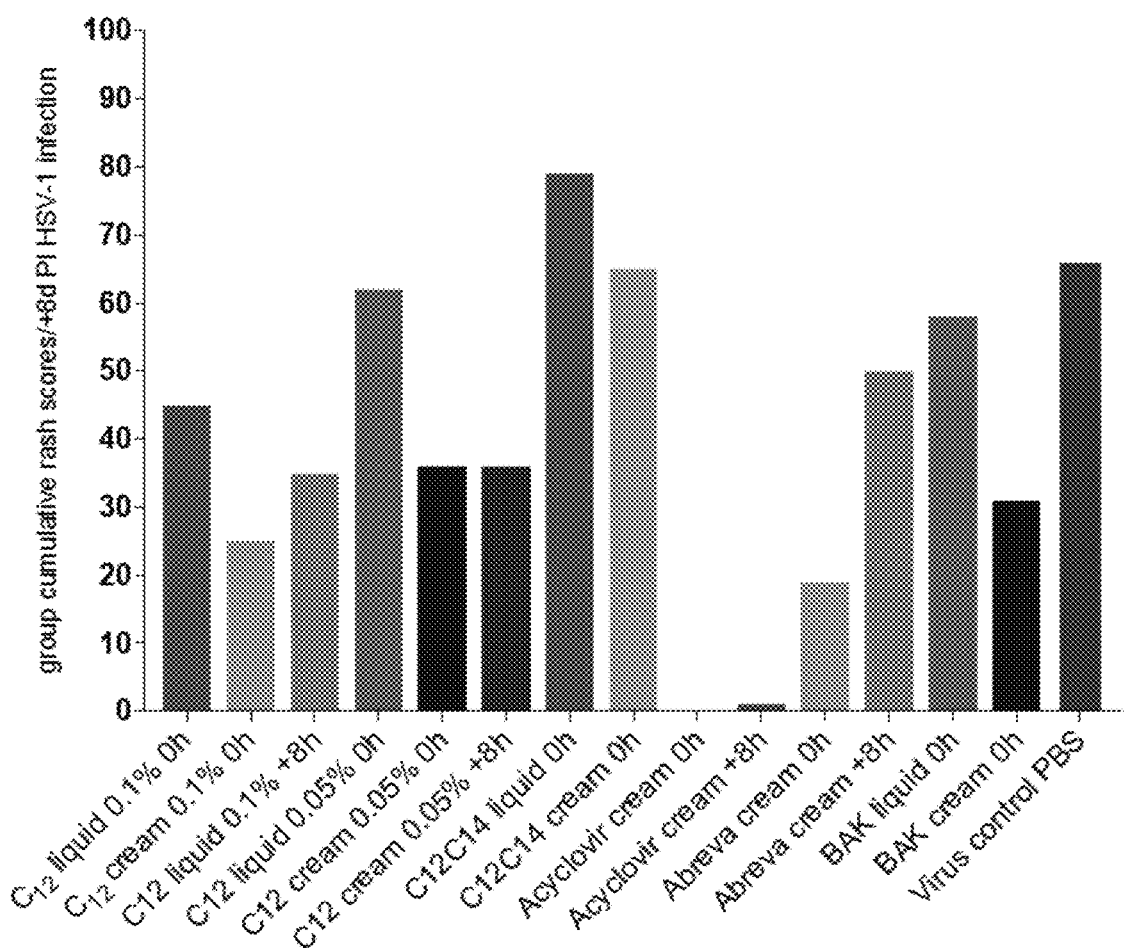
FIG. 12 shows the cumulative rash scores +8 d Post-Infection, all data.
Figure 13:
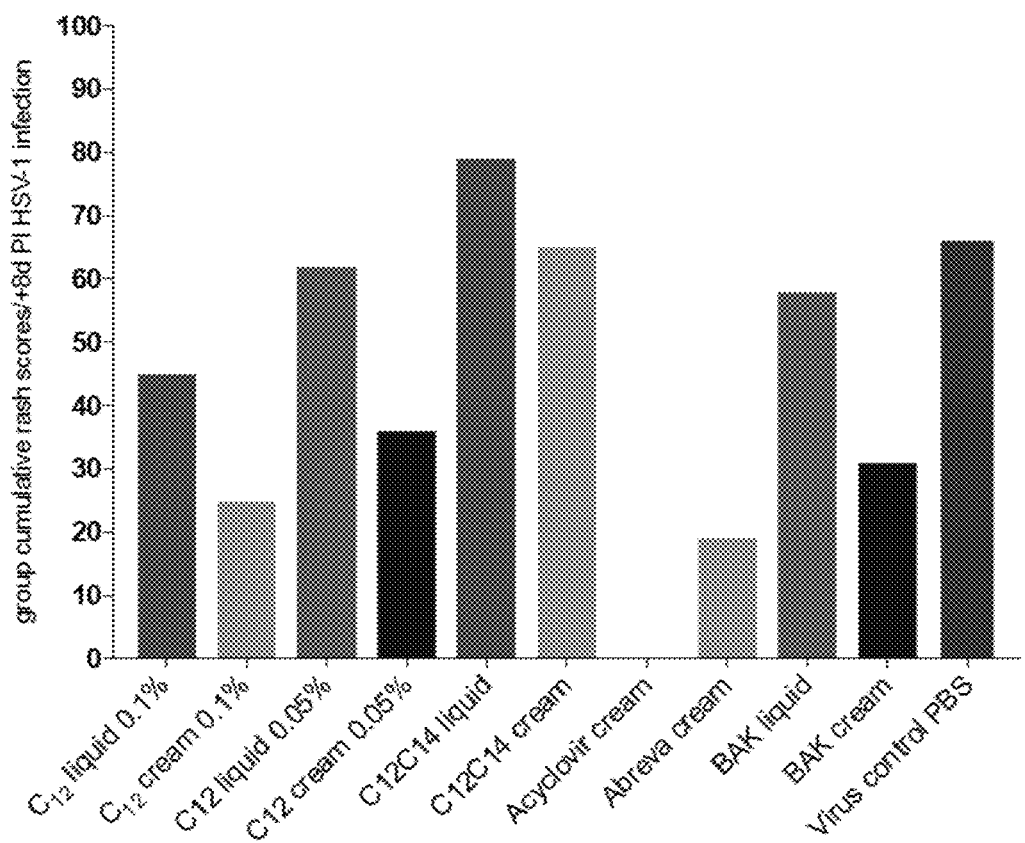
FIG. 13 shows the cumulative rash scores, +8 d Post-Infection, 0 h initiation of Rx.
Figure 14:
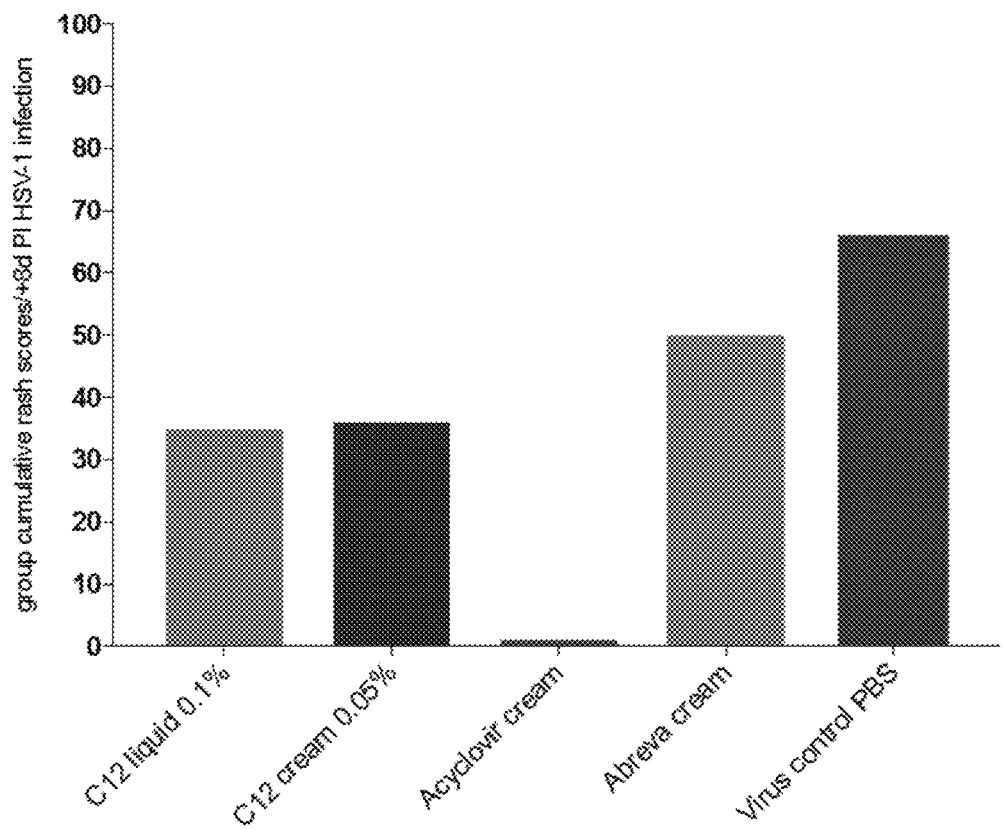
FIG. 14 shows the cumulative rash scores +8 d Post-Infection, +8 h initiation of Rx.
Figure 15:
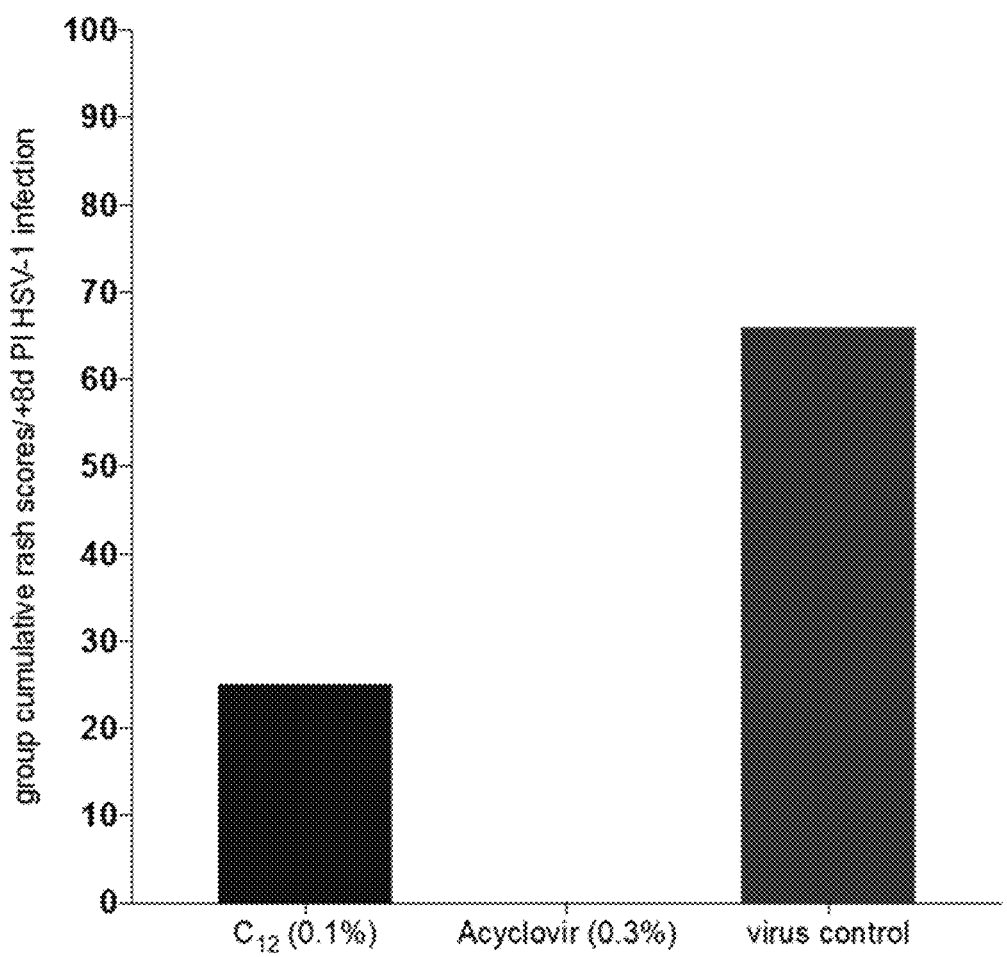
FIG. 15 shows the cumulative rash scores +8 d Post-Infection, C12-alkyl(ethylbenzyl) dimethylammonium chloride, acyclovir, virus control, 0 h initiation of Rx.
Figure 16A:
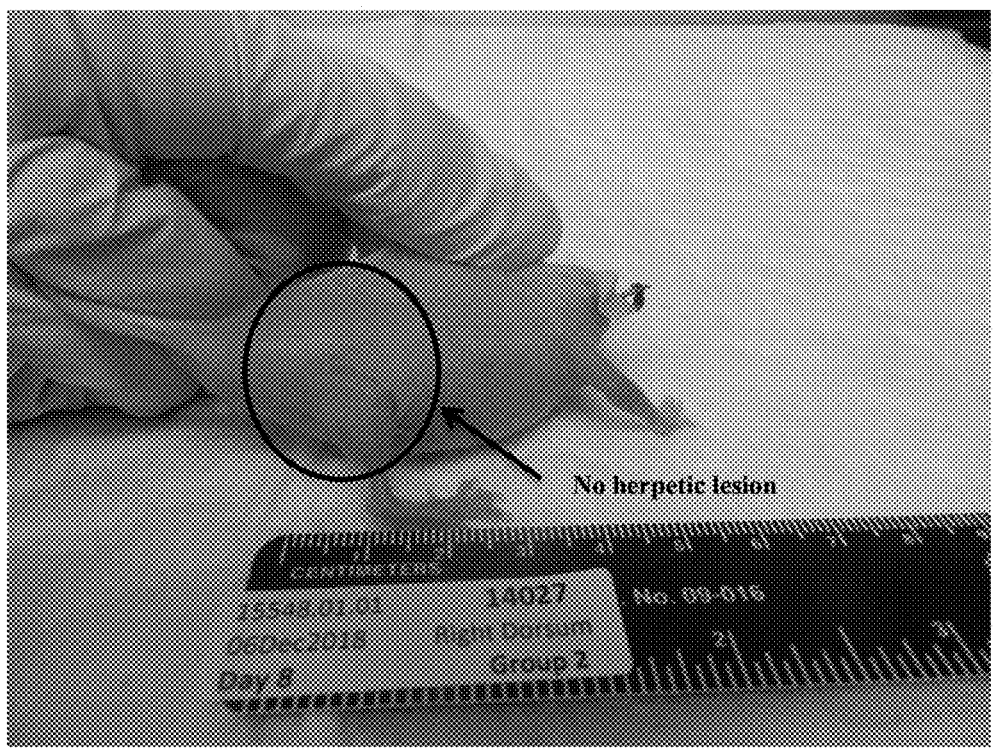
FIG. 16A shows a C12-alkyl(ethylbenzyl) dimethylammonium chloride (0.1% cream) treated mouse +8 d Post-Infection.
Figure 16B:
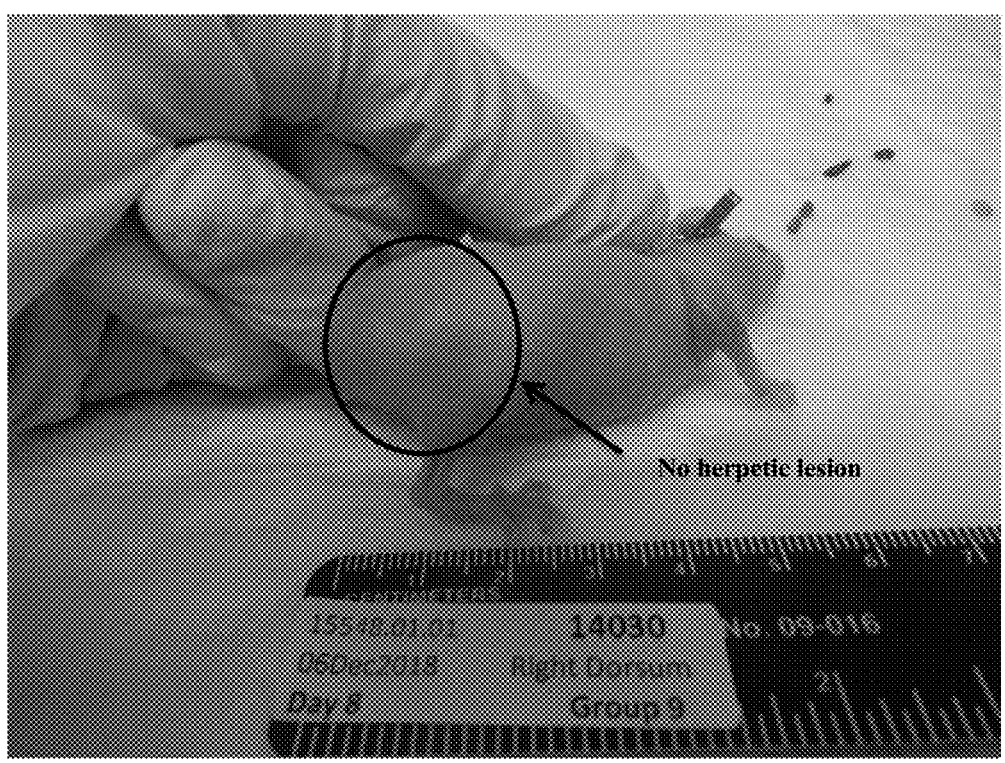
FIG. 16B shows an acyclovir treated mouse +8 d Post-Infection.
Figure 16C:
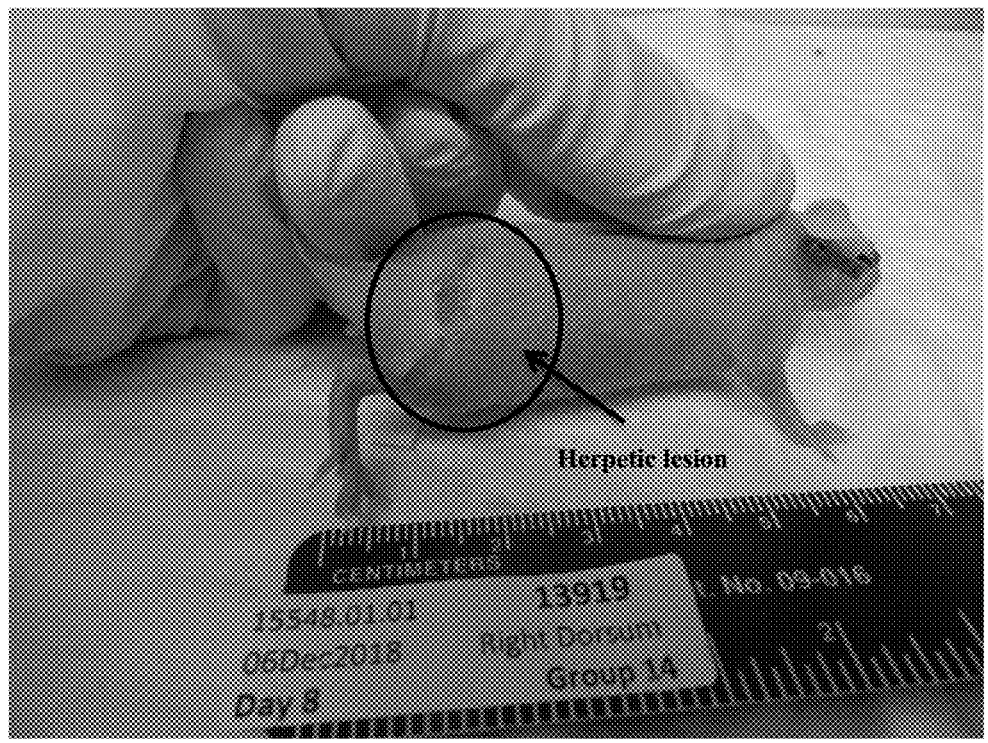
FIG. 16C shows a benzalkonium chloride (BAK) treated mouse +8 d Post-Infection.
Figure 16D:
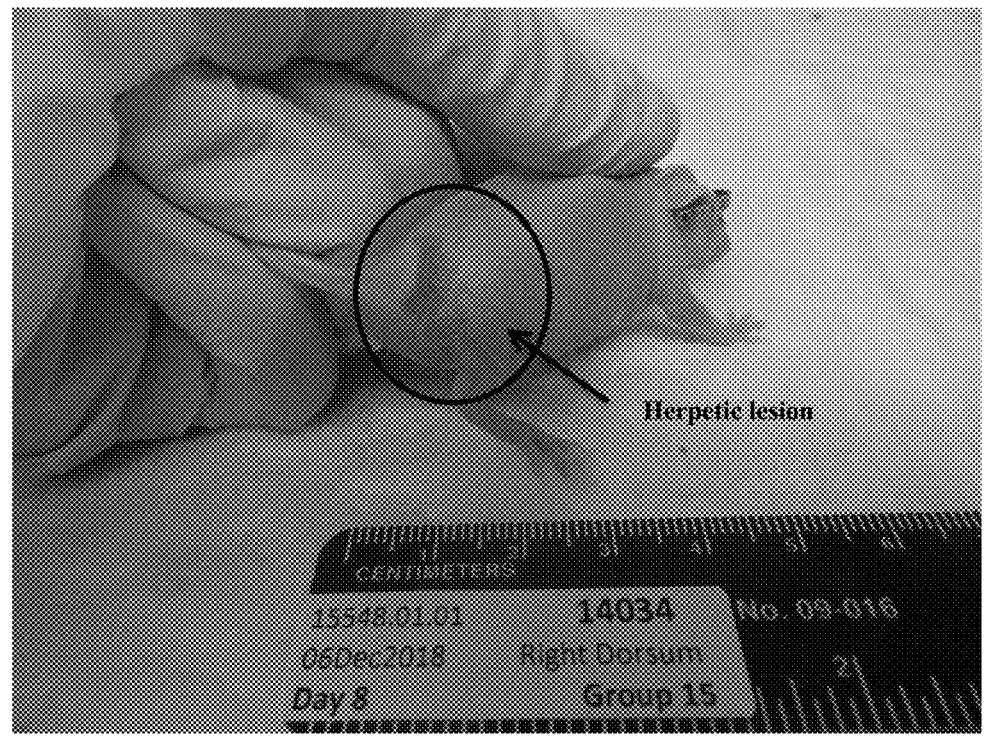
FIG. 16D shows a vehicle treated mouse +8 d Post-Infection.

C12-alkyl(ethylbenzyl) dimethylammonium chloride and acyclovir were applied 5 times a day as creams. The graphical representation can be seen in FIG. 7A and FIG. 7B.

Example 20—Evaluation of Topical Formulation Against Herpes Simplex Virus Type 1 (HSV-1) Infection in the Murine Zosteriform Model The objective of this study was to evaluate the efficacy of an investigational drug on the treatment of HSV-1 infection in the murine zosteriform model. Mice were infected with HSV-1 through dermal scarification and then topically administered the test articles either at 0 hour or 3 hours following infection and applied three times daily for 4 days. Three distinct formulations of different concentrations of this investigational drug were evaluated for efficacy and compared to control animals administered the current FDA approved medication for the treatment of HSV-1 infections in humans, Abreva® (10% Docosanol), which is available over-the-counter.

In this model, virus replication results in a rash or lesion that spreads from the inoculation site. As the infection progresses, the rash becomes necrotic, paralysis of the hind limbs develops, and then mortality. Severity of infection is scored on a scale of zero (no visible infection) to six (confluent rash with necrosis or death). This model allows one to monitor the effects of drugs on both local (skin lesions) and systemic manifestations (cold sores, encephalitis/death) of the disease in a single experiment. In humans, HSV-1 produces similar manifestations (i.e. skin lesions, encephalitis/death) and thus, this model represents an excellent means to evaluate HSV-1 therapeutics.

Primary Endpoint:
Determine the therapeutic efficacy of investigational test articles and dosage required for the effective treatment of HSV-1 in a murine zosteriform model of infection.

Secondary Endpoints:
Assessment of survival following challenge with HSV-1. Comparative analysis was conducted between the different treatment groups.
Assessment of rash severity following challenge with HSV-1. Comparative analysis was conducted between the different treatment groups (i.e. Abreva®, and the investigational formulations).

Test Articles

| Ingredient | A-20 % (w/w) | B-20 % (w/w) | C-20 % (w/w) |
|---|---|---|---|
| sodium phosphate, heptahydrate, dibasic | 0.195 | 0.195 | 0.195 |
| sodium phosphate, monohydrate, monobasic | 0.012 | 0.012 | 0.012 |
| sodium chloride | 0.10 | 0.10 | 0.10 |
| potassium chloride | 0.20 | 0.20 | 0.20 |
| Tetronic 908 | 0.250 | 0.250 | 0.250 |
| ammonium chloride | 0.25 | 0.25 | 0.25 |
| stabilized chlorine dioxide (as sodium chlorite) | 0.02 | 0.03 | 0.04 |
| C12-C14-alkyl(ethylbenzyl)-dimethylammonium chloride | 0.0100 | 0.0150 | 0.0200 |
| propylene glycol | 0.75 | 0.75 | 0.75 |
| EDTA | 0.05 | 0.05 | 0.05 |

Control Articles
Abreva®=10% Docosanol, Cream
Phosphate Buffered Saline (PBS)
HSV-1 Challenge Virus Diluent=DMEM and Fetal Bovine Serum (FBS)
Challenge Virus Article:
HSV-1 Challenge Virus Inoculum
Name: Herpes Simplex Virus Type 1 (HSV-1), Strain F
Lot No.: 010312, Supernatant fraction
Supplier: Southern Research Institute. Propagated using stock of HSV-1, Strain F (Catalog No., VR-733) provided by American Type Culture Collection (Manassas, Va.).
Formulation: The virus challenge inoculum was prepared in challenge virus diluent to yield a challenge dose of 2×10$^7$ PFU/mL (equivalent to 5×10$^5$ PFU/25 μl). The challenge inoculum was stored on wet ice and used on the day of formulation.
Test System
Species & Strain: Hairless Mice, SKH1
Supplier: Charles River Laboratories
Quarantine: 7 days
Age at Study Start: 6-7 weeks
Weight at Study Start: 17.7-23.4 g
Number on Study (Sex): 64 (Female)
Experimental Design—Group Assignment and Treatment
Sixty-four female SKH1 hairless mice were randomly distributed by weight using Provantis (Instem™ LSS Ltd., Staffordshire, UK) and assigned into eight groups as outlined in Table 22. All animals were challenged via scarification with HSV-1 on the lower (caudal) right dorsum. Animals in Groups 1 and 3-8 were administered the topical application as indicated beginning approximately 0 or 3 hours following the challenge. Group 2 remained untreated. The treatment arms of Abreva® and test articles involved three daily applications up through Day 4 post-challenge (administered approximately (±1 hour) every 4 hours).

TABLE 22

Study Design and Treatment Groups

| Group | Size (n) | Description[1] | Initiation of Treatment (hours post infection) | Frequency of application[3] |
|---|---|---|---|---|
| 1 | 8 | Virus control | 0 (sham-PBS) | On day 0, first application initiated at either 0 or 3 hours post-infection On days 0-4 post infection, 3 daily applications, approximately 4 hours apart. |
| 2 | 8 | Virus control | 0 (no treatment) | |
| 3 | 8 | B-20 | 0 | |
| 4 | 8 | B-20 | 3 | |
| 5 | 8 | C-20 | 0 | |
| 6 | 8 | A-20 | 0 | |
| 7 | 8 | Abreva(R) | 0 | |
| 8 | 8 | Abreva(R) | 3 | |

[1]All animals were infected with the F strain of HSV-1 via scarification with $5 \times 10^5$ PFU of the virus challenge inoculum.
[3]The 3 daily applications of Abreva ®, PBS and A-20, B-20 and C-20 were administered every 4 hours (±60 minutes).

In Vivo Procedures
HSV-1 Virus Challenge

On Study Day 0, all mice were infected with 25 µl of HSV-1 (F strain) challenge virus inoculum at 2×107 PFU/ml (equating to 5×105 PFU/25 µl). Animals were anesthetized, and then scarified by abrading the skin 10-30 (target=20) times on the lower (caudal) right dorsum in a crossed-hatch pattern with a 27-gauge retractable needle. The viral suspension was rubbed on the scarified skin area with a polyester-tipped applicator saturated with challenge virus diluent.

Administration of Control and Test Articles

All treatments were initiated at 0 or 3 hours post-challenge and administered three times daily for five days (Study Days 0-4) for test and control articles. The 3 daily applications of test and control articles were administered every 4 hours (+/−1 hour). The entire infection area was treated with 50 µL of test or control articles. Washes were not performed between applications. Mice were fitted with Elizabethan collars to prevent self-grooming and removal of the application. Collars were fitted immediately following or just before the first application of the day and were removed at least one hour after the last application of the day. Removing the collars one hour after the last application of the day ensured the topical was adequately absorbed and allowed the mice to have ample opportunity during the night to nestle unrestricted.

Scoring of Zosteriform Rash

Rash severity was scored once daily from Study Days 0 to 15. Mice were scored daily (those found dead were scored a 6) for signs of disease progression using the following scale from 0 to 6:
0=no visible papule or lesion present
1=Papules or lesions present at the inoculation site or lesions have healed/scarring present.
2=Discrete lesions or papules developing away from the inoculation site or desquamation present with minimal scabbing.
3=Lesions or papules appearing on one or more of the following body regions, leg, genital area, and abdomen, but not confluent. Indication of scabbing may be evident during the healing process.
4=Rash near confluent. Rash not ulcerated.
5=Rash confluent with possible secondary lesions evident. Evidence of sites of ulceration may be present.
6=Rash confluent with complete ulceration and/or necrosis.

In Vitro Test Procedures
HSV-1 Challenge Virus Preparation

The HSV-1 stock virus (Lot No. 010312, supernatant fraction) was thawed in a 37±1° C. water bath and diluted with HSV-1 challenge virus diluent to $2 \times 10^7$ PFU/mL. Two aliquots of the virus formulation were retained and stored at −70±10° C. until the completion of the study. One aliquot was taken and stored on wet ice until used for the back-titration. The titer of the challenge material was confirmed through a back-titration using a standard plaque assay.

Challenge Inoculum Back Titration

An aliquot of challenge inoculum was titrated onto Vero cells (ATCC No. CCL-81) to confirm the challenge dose in accordance with approved procedures.

Data Analysis

Daily cumulative rash scores from the individual mice in the groups over the 15 day period were analyzed. Mean+/SEM was plotted and the 'area under the curve' (AUC) for the rash scores of each mouse was calculated. Differences in the AUC of rash scores from group means as compared to the infected controls was analyzed. Photographs were used as visual aids to the Rash score analysis.

Results and Discussion
Scoring of Zosteriform Rash

Injection sites were observed for 15 days following immunization for redness, rash, swelling. Rash severity was scored once daily from Study Days 0 to 15. Area under the curve (AUC) was calculated for the rash scores. Mean rash scores and mean AUC are summarized in Table 23 below. Animals which were incolulated with virus followed by PBS sham treatment (Group 1) showed higher AUC rash scores (AUC score of 32.6) compared to no treatment (Group 2) (AUC score of 25.4). This may be due to the spreading of inoculated virus by additional rubbing with PBS. Mice treated with the positive control Abreva either at the time of infection (Group 7) or 3 hours after infection (Group 8) showed similar rash scores (AUC of 28.1 and 26.9, respectively) compared to sham controls (AUC scores of 32.6). Abreva's lack of antiviral effect might be due to less frequent topical application (applied only three times a day on Days 0-4) used in this study. For optimal antiviral effect in this mouse model, Abreva probably needs more frequent application and/or prolonged treatment duration (more than 4 days of application).

TABLE 23

Mean Rash scores and Mean AUC (Area Under Curve) in HSV-infected mice treated with different Test articles

| Group | Mean Rash Scores Days post-infection | | | | | | | | | | | | | | | | Mean AUC |
|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | |
| 1 | 0 | 0 | 0 | 1 | 1 | 1 | 2 | 3 | 3 | 3 | 3 | 3 | 4 | 4 | 4 | 4 | 32.6 |
| 2 | 0 | 0 | 0 | 1 | 1 | 2 | 2 | 3 | 3 | 3 | 4 | 4 | 1 | 1 | 1 | 1 | 25.4 |
| 3 | 0 | 0 | 0 | 1 | 1 | 2 | 2 | 3 | 3 | 3 | 3 | 3 | 1 | 1 | 1 | 1 | 21.9 |
| 4 | 0 | 0 | 0 | 1 | 1 | 3 | 3 | 4 | 4 | 4 | 4 | 4 | 3 | 3 | 3 | 3 | 39.0 |
| 5 | 0 | 0 | 0 | 0 | 1 | 1 | 1 | 1 | 1 | 2 | 1 | 1 | 1 | 1 | 0 | 0 | 108 |
| 6 | 0 | 0 | 0 | 1 | 1 | 2 | 2 | 3 | 4 | 4 | 4 | 4 | 3 | 3 | 3 | 3 | 36.2 |
| 7 | 0 | 0 | 0 | 0 | 1 | 1 | 2 | 2 | 3 | 3 | 3 | 3 | 3 | 3 | 3 | 3 | 28.1 |
| 8 | 0 | 0 | 0 | 0 | 1 | 2 | 2 | 2 | 3 | 3 | 3 | 3 | 3 | 3 | 2 | 2 | 26.9 |

Mice treated with the high dose of B-20 at the time of infection (Group 3) showed lower rash scores (AUC score of 21.9) compared to the mice treated with the high dose of B-20 at 3-hours post-infection (Group 4) (AUC score of 39), demonstrating the potential antiviral activity of B-20 probably at the virus infection stage. Mice treated with A-20 at the time of infection (Group 6) showed similar rash scores (AUC score of 36.2) compared to sham treated virus controls (Group 1) (AUC score of 32.6). Interestingly, mice treated with the low dose C-20 (Group 5) showed low rash scores (AUC score of 10.8) compared to either the sham control (Group 1) or any other treatment groups (Groups 3, 4, 6, 7 and 8), including the positive control (Abreva) groups (Groups 7 and 8).

Clinical Observations

Detailed observations were performed at least once daily. Sham treated virus infected mice (Group 1) showed significant mortality with only 37.5% of the mice surviving at the end of the study. In contrast, no mortality was observed in virus infected without treatment (Group 2). Mice treated with high dose of B-20 either at the time of infection (Group 3) or 3 hours post-infection (Group 4) showed moderate survival (87.5% and 62.5% respectively). Similarly, mice treated with the positive control Abreva either at the time of infection (Group 7) or 3 hours post-infection (Group 8) showed moderate survival (62.5%). A-20 treated mice (Group 6) showed low survival (50%). In contrast, mice treated with low dose C-20 (Group 5) showed 100% survival. Overall, there seems to be a positive correlation between rash scores and the mortality observed in various groups of mice.

Mice infected with HSV followed by sham treatment showed significant rashes (as evident by the rash scores and the AUC scores) and low survival. Positive control Abreva did not show an effect on rash scores and had only a slight effect on survival. B-20 showed moderate effect when applied at the time of infection, but lost its antiviral effect when applied 3 hours post-infection. A-20 did not show any antiviral effect. Mice treated with low dose C-20 (Group 5) showed promising antiviral effect (low rash scores) and higher survival (100% survival) compared to sham treated mice (Group 1). Three times a day application only during the first 5 days of infection seems to be a very stringent condition for the evaluation of antivirals in the HSV mouse model used for this study.

Example 21: Evaluation of Topical Formulation Against Herpes Simplex Virus Type 1 (HSV-1) Infection in the Murine Zosteriform Model The objective of this study is to evaluate the efficacy of an investigational drug on the treatment of HSV-1 infection in the murine zosteriform model. Mice will be infected with HSV-1 through dermal scarification and then topically administered the test articles either at 0 hour or 8 hours following infection and applied five times daily for seven (7) days. Two distinct formulations (liquid and cream) of different investigational test articles will be evaluated for efficacy and compared to control animals administered with Zovirax, Abreva® (10% Docosanol) and benzalkonium chloride which are available by prescription or over-the-counter.

In this model, virus replication results in a rash or lesion that spreads from the inoculation site. As the infection progresses, the rash becomes necrotic, paralysis of the hind limbs develops, and then mortality. Severity of infection is scored on a scale of zero (no visible infection) to six (confluent rash with necrosis or death). This model allows one to monitor the effects of drugs on both local (skin lesions) and systemic manifestations (cold sores, encephalitis/death) of the disease in a single experiment. In humans, HSV-1 produces similar manifestations (i.e. skin lesions, encephalitis/death) and thus, this model represents an excellent means to evaluate HSV-1 therapeutics.

The Primary Endpoint for this Study:
  Determine the therapeutic efficacy of investigational test articles and dosage required for the effective treatment of HSV-1 in a murine zosteriform model of infection.

Secondary Endpoints Include:
  Assessment of rash severity following challenge with HSV-1. Comparative analysis will be conducted between the different treatment groups (i.e. Zovirax, Abreva®, and benzalkonium chloride and the investigational formulations).
  Assessment of survival following challenge with HSV-1. Comparative analysis will be conducted between the different treatment groups.

Test Articles

| Active agent | Concentration |
|---|---|
| C12-alkyl(ethylbenzyl)dimethylammonium chloride liquid | 1 mg/ml (Group 1) and 0.5 mg/ml (Group 4) |
| C12-alkyl(ethylbenzyl)dimethylammonium chloride cream | 1 mg/mL (Groups 2/3) and 0.5 mg/mL (Groups 5/6) |
| C12-C14 alkyl(ethylbenzyl)dimethylammonium chloride liquid | 1 mg/mL (Group 7) |
| C12-C14 alkyl(ethylbenzyl)dimethylammonium chloride cream | 1 mg/mL (Group 8) |

Control Articles

| | | |
|---|---|---|
| Abreva ® | 10% Docosanol, Cream | Groups 11/12 |
| Zovirax ® | Acyclovir Cream, 5% | Groups 9/10 |
| Benzalkonium Chloride (BAK, Liquid) | 1 mg/mL | Groups 13/14 |
| Phosphate Buffered Saline (PBS) | | Group 15 |

HSV-1 Challenge Virus Diluent
Constituent: DMEM (without phenol red) and Fetal Bovine Serum (FBS)
Manufacturer: DMEM (Gibco)
FBS (Sigma-Aldrich)
Challenge Virus Article
HSV-1 Challenge Virus Inoculum
Name: Herpes Simplex Virus Type 1 (HSV-1), Strain F
Supplier: Southern Research Institute. Propagated using stock of HSV-1, Strain F (Catalog No., VR-733) provided by American Type Culture Collection (Manassas, Va.).
Formulation: The virus challenge inoculum was prepared in challenge virus diluent to yield a challenge dose of 2×107 PFU/mL (equivalent to 5×105 PFU/25 μl). The challenge inoculum was stored on wet ice and used on the day of formulation.
Test System:
Species & Strain: Hairless Mice, SKH1
Supplier: Charles River Laboratories
Quarantine: Minimum of 5 days
Age at Study Start: 5 to 7 weeks of age
Weight at Study Start: 15 to 25 g
Number on Study: 126
Sex: Females
Experimental Design:
Group Assignment and Treatment:
One hundred and twenty six (126) female SKH1 hairless mice were randomly distributed using Provantis (Instem™ LSS Ltd., Staffordshire, UK) and assigned into sixteen groups as outlined in Table 24. All animals in Groups 1-15 were challenged via scarification with HSV-1 on the lower (caudal) right dorsum. Animals in Groups 1 to 15 were administered the topical application as indicated beginning approximately 0 or +8 hours following the challenge. Group 15 received PBS treatment. Group 16 was an uninfected normal control. The treatment arms of positive controls (Abreva, Zovirax and Benzalkonium Chloride) and test articles involved five daily applications from Day 0 up to Day 6/7 post-challenge (as shown in Table 24) to be administered approximately (±1 hour) every 3 hours.

TABLE 24

Study Design and Treatment Groups[1,2,3]

| Group | size | description | physical form of treatment | Initiation of treatment[4] | Frequency of application |
|---|---|---|---|---|---|
| 1 | 8 | $C_{12}$ homologue | Liquid | 0 | 5X a day; d0-6 |
| 2 | 8 | | Cream | 0 | 5X a day; d0-6 |
| 3 | 8 | | | +8 h | 5X a day; d0-7 |
| 4 | 8 | $C_{12}$ homologue (0.5 dose) | Liquid | 0 | 5X a day; d0-6 |
| 5 | 8 | | Cream | 0 | 5X a day; d0-6 |
| 6 | 8 | | | +8 h | 5X a day; d0-7 |
| 7 | 8 | $C_{12}C_{14}$ | Liquid | 0 | 5X a day; d0-6 |
| 8 | 8 | | Cream | 0 | 5X a day; d0-6 |
| 9 | 8 | acyclovir/Zovirax ® | Cream | 0 | 5X a day; d0-6 |
| 10 | 8 | | | +8 h | 5X a day; d0-7 |
| 11 | 8 | docosanol/Abreva ® | | 0 | 5X a day; d0-6 |
| 12 | 8 | | | +8 h | 5X a day; d0-7 |
| 13 | 8 | benzalkonium chloride | Liquid | 0 | 5X a day; d0-6 |
| 14 | 8 | | Cream | 0 | 5X a day; d0-6 |
| 15 | 8 | virus control (PBS) | Liquid | 0 | 5X a day; d0-6 |
| 16 | 6 | Uninfected Normal controls | N/A | N/A | N/A |

[1]All animals in Groups 1-15 were infected with the F strain of HSV-1 via scarification with $5 \times 10^5$ PFU of the virus challenge inoculum.
[2]Groups 1-15 were topically administered the control (i.e. Abreva ®, Zovirax, benzalkonium chloride or PBS) or test article (i.e. C12 homologue or C12C14) as indicated with the first application to be initiated at either 0 hour or 8 hours post-infection.
[3]The 5 daily applications of positive controls and test articles were administered approximately every 3 hours (± 60 minutes) from morning 6 AM to evening 6 PM (6 AM, 9 AM, 12 noon, 3 PM. 6 PM).
[4]The total times for treatment for the groups initiating at +8 h PI was the same (5x/d * 7 d = 35 Rx) as the groups initiating at 0 h post-infection. The +8 h applications was initiated approx. 8 hours post-infection, therefore only 2 applications took place on Day 0. One additional application for those groups took place on Day 7 for a total of 35 applications.
N/A: Not applicable In Vitro Test Procedures:
HSV-1 Challenge Virus Preparation:
The HSV-1 stock virus was thawed in a 37±1° C. water bath and diluted with HSV-1 challenge virus diluent to $2 \times 10^7$ PFU/mL. An aliquot of the virus formulation was retained and stored at −70° C. or below until the completion of the study. The titer of the challenge material was confirmed through a back-titration using a standard plaque assay.
Challenge Inoculum Back Titration:
An aliquot of challenge inoculum was titrated onto Vero cells (ATCC No. CCL-81) to confirm the challenge dose in accordance with approved procedures.
In Vivo Test Procedures: hSV-1 Virus Challenge:
All mice were infected with 25-75 μl (volume to be determined based on virus titer) of HSV-1 (F strain) challenge virus inoculum at $2 \times 10^7$ PFU/ml (equating to $5 \times 10^5$ PFU/25 μl). Animals were anesthetized, and then scarified by abrading the skin 10-30 (target=20) times on the lower (caudal) right dorsum in a crossed-hatch pattern with a 27-gauge needle. The viral suspension was rubbed on the scarified skin area with a polyester-tipped applicator saturated with challenge virus diluent.
Administration of Control and Test Articles:
All treatments were initiated at 0 or 8 hours post-challenge and administered five times daily for seven days for test and control articles (5×/d*7d=35 Rx). The 5 daily applications of test and control articles were administered every 3 hours (+/−1 hour). The entire infection area was treated with 50 µL of test or control articles. Washes were not performed between applications.

Mice were fitted with Elizabethan collars to prevent the self-grooming and removal of the application. Collars were fitted immediately following or just before the first application of the day and will be removed at least one hour after the last application of the day. Removing the collars one hour after the last application of the day ensures the topical has been adequately absorbed and allows the mice to have ample opportunity during the night to nestle unrestricted.

Scoring of Zosteriform Rash:

Rash severity were scored once daily from Study Days 0 to 15. Mice will be scored daily (those found dead will be scored a 6) for signs of disease progression using the following scale from 0 to 6:

0=no visible papule or lesion present
1=Papules or lesions present at the inoculation site or lesions have healed/scarring present.
2=Discrete lesions or papules developing away from the inoculation site or desquamation present with minimal scabbing.
3=Lesions or papules appearing on one or more of the following body regions, leg, genital area, and abdomen, but not confluent. Indication of scabbing may be evident during the healing process.
4=Rash near confluent. Rash not ulcerated.
5=Rash confluent with possible secondary lesions evident. Evidence of sites of ulceration may be present.
6=Rash confluent with complete ulceration and/or necrosis.

The daily cumulative rash scores can be seen in FIG. 8 to FIG. 15. Pictures of rash development in HSV-1 infected mice are shown in FIG. 16A to FIG. 16D.

Example 22. Ebola Virus Deactivation Studies (BSL-4)

Figure 17:
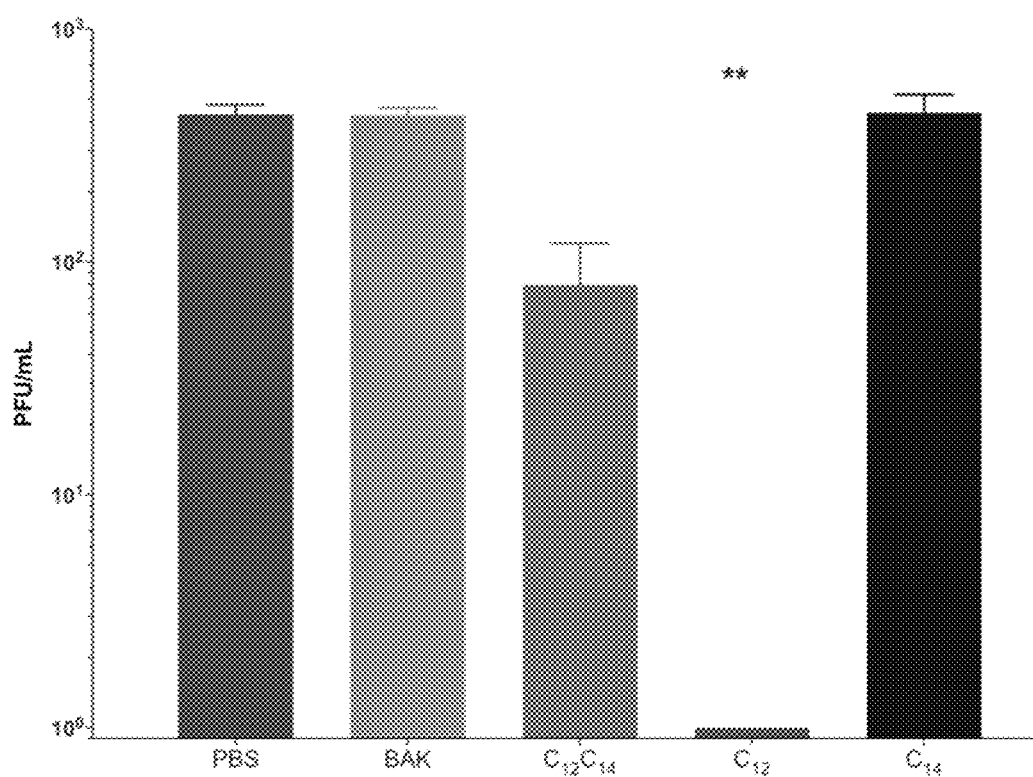
FIG. 17 shows the results from the Ebola virus deactivation study for C12-alkyl(ethylbenzyl) dimethylammonium chloride, C14-alkyl(ethylbenzyl) dimethylammonium chloride, and C12-C14-alkyl(ethylbenzyl) dimethylammonium chloride as compared to benzalkonium chloride (BAK) and PBS.

The test was performed with fully virulent Ebola virus (Zaire 76). The concentration C12-alkyl(ethylbenzyl) dimethylammonium chloride, C14-alkyl(ethylbenzyl) dimethylammonium chloride, and C12-C14-alkyl(ethylbenzyl) dimethylammonium chloride tested were 5 µg/ml. Complete deactivation of Ebola by C12-alkyl(ethylbenzyl) dimethylammonium chloride is seen in FIG. 17.

Example 23: Phase 1 Clinical Trial for the Treatment of Cold Sores

The purpose of this study is to determine if a pharmaceutical composition described herein (Composition 1), is safe and effective in reducing the severity and duration of cold sores.

Subjects who meet the requirements to participate in the study will be put randomly, and equally, into one of two groups: 1) a group receiving Composition 1 to treat their cold sore; or 2) a group receiving a placebo to treat their cold sore. Neither the subject nor the site will know which treatment they will be getting. Once the subject has been assigned to a treatment group, they will be given a kit containing a bottle of the treatment and special swabs to apply the liquid. The subject will be told to take the kit home and wait until they think they are starting to get a cold sore.

Once a subject begins to feel something or see something that they think is the start of a cold sore, they are to immediately call the clinic. Once the clinic confirms that the subject is in fact starting to get a cold sore, the subject will be told to open the kit and begin treatment.

Subjects will need to report daily to the clinic for a minimum of 3 consecutive days, until either the cold sore is completely healed or 14 days from the start of treatment, whichever comes first. At each clinic visit the cold sore will be observed to determine at what stage it is at or if it has healed. The subject will also be asked how they are feeling.

Subjects will also be told to record in a diary the time of each application of Composition 1 or placebo. They will also be asked to record how much pain, if any, related to the cold sore, that they are feeling.

| Condition | Intervention | Phase |
|---|---|---|
| Recurrent Herpes Labialis | Drug: Composition 1 Drug: Placebo | Phase 1 |

Study Type: Interventional
Study Design: Allocation: Randomized
  Intervention Model: Parallel Assignment
  Masking: Double Blind (Participant, Investigator, Outcomes Assessor)
  Primary Purpose: Treatment
Primary Outcome Measures:
Clinician Assessed Duration of Complete Healing of the Herpetic Episode [Time Frame: Days 1-14]

| Arms | Assigned Interventions |
|---|---|
| Experimental: Composition 1 36 applications over a 96 hour period | Drug: Composition 1 |
| Placebo 36 applications over a 96 hour period | Drug: Placebo |

Eligibility
Ages Eligible for Study: 18 Years to 75 Years (Adult, Senior)
Sexes Eligible for Study: All
Accepts Healthy Volunteers: No
Criteria
  Inclusion Criteria:
  Male or female subject 18-75 years of age
  Female subjects must be using a medically acceptable form of birth control during the study.
  Subject must have a history of recurrent herpes labialis and report at least 3 separate recurrences (i.e. multiple herpetic lesions in one outbreak count as only one episode) during the preceding 12 months.
  Subject must have a history of experiencing prodromal symptoms of cold sores (e.g. itching, tingling, or burning) during at least half of their previous cold sore episodes.
  Subject must have a history of at least half of their cold sore episodes producing classical lesions (i.e., episodes that progressed through macule, papule, vesicle, crust, and healed).
  Subject must provide voluntary written informed consent to participate in this study.
  Subject is able to appear for a clinic visit within 24 hours from the time of treating cold sore and is able to return to the clinic for the full 14 day duration of the study if necessary.
  Exclusion Criteria:
  Subjects with evidence of active malignancy or immunodeficiency disease within the last 30 days.

Subjects who have completed therapy and are considered unlikely to relapse or who have had surgery and do not have any evidence of disease, are eligible for the study.

Subject requires chronic use of immunomodifying drugs (e.g. systemic steroids) or topical steroids on or near the face; use of inhaled steroids does not exclude a subject from the study. If a subject is unlikely to get through the Treatment Phase of the protocol without requiring the use of an immunomodifying drug for a chronic condition the subject should be excluded.

Subject requires chronic use of anti-viral medication.

In females of childbearing potential, a positive urine pregnancy test at time of screening.

Nursing mothers.

Subject has abnormal skin conditions (e.g. acne, eczema, rosacea, psoriasis, albinism, or chronic vesiculobullous disorders) that occur in the area ordinarily affected by cold sores or has significant facial hair in the area of the cold sore that might affect the normal course of the cold sore or might impair accurate evaluation of the cold sore lesion.

Subject has had a vaccine for herpes simplex virus type 1 (typically oral herpes) or 2 (typically genital herpes).

Subject is currently enrolled in another clinical trial involving the use of a drug and/or a device.

Subject requires chronic use of analgesics or non-steroidal anti-inflammatory agents (NSAIDs) except for low doses of aspirin (less than 325 mg/day) used for cardiovascular purposes. If a subject is unlikely to get through the Treatment Phase of the protocol without requiring the use of analgesia for a chronic condition, e.g. back pain, recurrent daily headaches, the subject should be excluded.

Example 24: Phase 1 Clinical Trial for the Treatment of Epidemic Keratoconjunctivitis (EKC)

The purpose of this study is to determine if a pharmaceutical composition described herein (Composition 1), is safe and effective for the treatment of acute phase adenovirus-induced EKC.

The aims of the study are to investigate the therapeutic efficacy of Composition 1 as measured by adenoviral load, time to viral eradication, clinical resolution of EKC (objective and subjective assessments), presence of opacities, visual acuity and frequency of second eye infections, and to assess the safety and tolerability of Composition 1 in EKC infected eyes.

Study Type: Interventional
Study Design: Allocation: Randomized
  Intervention Model: Parallel Assignment
  Masking: Triple (Participant, Care Provider, Investigator)
  Primary Purpose: Treatment
Primary Outcome Measures:

The primary objective is to assess the adenoviral load in epidemic keratokonjunctivitis (EKC) infected eyes following topical treatment with Composition 1 compared to placebo. [Time Frame: 14 days]. Viral load in tear liquid from EKC infected eyes, as measured by the area under the curve (AUC) at 3-14 days from start of treatment.

Secondary Outcome Measures:

Assess the time to viral eradication in EKC infected eyes following treatment with Composition 1 compared to placebo. [Time Frame: 14 days]. The time point of viral eradication in tear liquid from EKC infected eyes, defined as the time Point when viral load=0 or below the lower limit of quantification (LLOQ).

Evaluate the effect of Composition 1 on clinical resolution of EKC, as measured by objective and subjective assessment of scaled clinical symptoms, compared to placebo. [Time Frame: 14 days]. Resolution of acute ocular symptoms at each time of assessment, as measured by objective (Investigator-based) assessment of conjunctival discharge and redness.

Evaluate the presence of opacities (quantitatively and qualitatively) following treatment with Composition 1 compared to placebo. [Time Frame: 14 days]. Presence and location of opacities at each time of assessment, as measured by slit lamp examination.

Assess the visual acuity following treatment with Composition 1 compared to placebo. [Time Frame: 28 days]. Visual acuity at each time of assessment by use of the logarithm of the Minimum Angle of Resolution (Log MAR) chart.

Assess the frequency of second eye infections. [Time Frame: 14 days]. Occurrence of second eye infection.

Assess the safety and tolerability of Composition 1. [Time Frame: 14 days]. Safety variables: adverse events (AEs) (nature and incidence), Physical examination, vital signs, laboratory safety assessments (haematology, clinical chemistry and urinalysis)

| Arms | Assigned Interventions |
| --- | --- |
| Active Comparator: Composition 1 | Drug: Composition 1 |
| Placebo Comparator | Placebo |

Eligibility
Ages Eligible for Study: 18 Years and older (Adult, Senior)
Sexes Eligible for Study: All
Accepts Healthy Volunteers: No
Criteria
  Inclusion Criteria:
  The patients have to meet all of the following criteria to be eligible to enter the study:
    Willing and able to provide informed consent.
    Men or women aged 18 years or above with onset of adenoviral EKC symptoms in at least one eye, as clinically diagnosed and with symptoms appearing within less 7 days at the time of giving informed consent.
    Using adequate contraceptive measures
  Exclusion Criteria:
    Known or suspected allergy to any ingredients or placebo.
    Symptoms correlating with EKC since more than 7 days.
    Diagnosis of other significant disease(s) than EKC in the eye.
    Diagnosis of bacterial or fungal ocular infections.
    Use of antibiotics or corticosteroids by any route (except intravitreal corticosteroids) within 14 days prior to inclusion. Ocular antibiotics may, however, be used until 2 hours prior to first dose of IMP, but are thereafter prohibited during the study.
    Use of immunosuppressive medications (including intravitreal corticosteroids) within 6 months prior to inclusion.
    Use of antiviral medications within 7 days prior to inclusion.
    Usage of any medication or herbal medicinal product with documented adverse reactions affecting the eyes.
    Usage of any medication or herbal medicinal product for ocular administration at inclusion.

Female patients: currently pregnant or breast-feeding or intending to become pregnant during the study period.

Known or suspected drug abuse.

Usage of contact lenses during the study.

Participation in any other interventional clinical study within 30 days prior to inclusion

What is claimed is:

1. A method of reducing the severity or the duration of the symptoms of a viral infection selected from herpes simplex virus type 1 (HSV-1), herpes simplex virus type 2 (HSV-2), and varicella zoster virus (VZV), in a subject in need thereof, the method comprising administering to the subject in need thereof a pharmaceutical composition comprising C12-C14-alkyl(ethylbenzyl)dimethylammonium chloride.

2. The method of claim 1, wherein the viral infection is caused by the herpes simplex virus.

3. The method of claim 1, wherein the symptoms of the infection are selected from lesions, pain, fever, swollen lymph nodes, and any combinations thereof.

4. The method of claim 1, wherein the C12-C14-alkyl (ethylbenzyl)dimethylammonium chloride is a mixture of C12-alkyl(ethylbenzyl)dimethylammonium chloride and C14-alkyl(ethylbenzyl)dimethylammonium chloride.

5. The method of claim 1, wherein the C12-C14-alkyl (ethylbenzyl)dimethylammonium chloride is C12-alkyl(ethylbenzyl)dimethylammonium chloride.

6. The method of claim 1, wherein the pharmaceutical composition is essentially free of alkyl(ethylbenzyl)dimethyl ammonium salt having an alkyl of less than 12 carbons or more than 14 carbons.

7. The method of claim 1, wherein the pharmaceutical composition is essentially free of benzalkonium chloride.

8. The method of claim 1, wherein the C12-C14-alkyl (ethylbenzyl)dimethylammonium chloride is present in an amount ranging from about 0.0001% to about 10% w/w.

9. The method of claim 1, wherein the C12-C14-alkyl (ethylbenzyl)dimethylammonium chloride is present in an amount ranging from about 0.001% to about 1% w/w.

10. The method of claim 1, wherein the pharmaceutical composition is in the form of an aerosol, a solution, a lotion, a gel, an ointment, a cream, a foam, a paste, or any combinations thereof.

11. The method of claim 1, wherein the subject in need thereof is immuno-compromised.

12. A method of preventing the spread of a viral infection selected from influenza virus, the herpes simplex virus, the human immunodeficiency virus (HIV), the hepatitis B virus, the hepatitis C virus, the human papillomavirus (HPV), the ebolavirus, and an adenovirus, in a subject in need thereof, the method comprising administering to the subject in need thereof a pharmaceutical composition comprising C12-C14-alkyl(ethylbenzyl)dimethylammonium chloride.

13. The method of claim 12, wherein the C12-C14-alkyl (ethylbenzyl)dimethylammonium chloride is a mixture of C12-alkyl(ethylbenzyl)dimethylammonium chloride and C14-alkyl(ethylbenzyl)dimethylammonium chloride.

14. The method of claim 12, wherein the C12-C14-alkyl (ethylbenzyl)dimethylammonium chloride is C12-alkyl(ethylbenzyl)dimethylammonium chloride.

15. The method of claim 12, wherein the pharmaceutical composition is essentially free of alkyl(ethylbenzyl)dimethyl ammonium salt having an alkyl of less than 12 carbons or more than 14 carbons.

16. The method of claim 12, wherein the pharmaceutical composition is essentially free of benzalkonium chloride.

17. The method of claim 12, wherein the C12-C14-alkyl (ethylbenzyl)dimethylammonium chloride is present in an amount ranging from about 0.0001% to about 10% w/w.

18. The method of claim 12, wherein the C12-C14-alkyl (ethylbenzyl)dimethylammonium chloride is present in an amount ranging from about 0.001% to about 1% w/w.

19. The method of claim 12, wherein the subject in need thereof is immuno-compromised.

* * * * *